US012573045B2

(12) United States Patent
Donovan et al.

(10) Patent No.: US 12,573,045 B2
(45) Date of Patent: Mar. 10, 2026

(54) CANDIDATE DETERMINATION FOR SPINAL NEUROMODULATION

(71) Applicant: Relievant Medsystems, Inc., Edina, MN (US)

(72) Inventors: Brian W. Donovan, San Jose, CA (US); Ray M. Baker, San Clemente, CA (US); Samit Patel, Palo Alto, CA (US)

(73) Assignee: Relievant Medsystems, Inc., Edina, MN (US)

( * ) Notice: Subject to any disclaimer, the term of this patent is extended or adjusted under 35 U.S.C. 154(b) by 328 days.

(21) Appl. No.: 18/339,007

(22) Filed: Jun. 21, 2023

(65) Prior Publication Data

US 2023/0394668 A1 Dec. 7, 2023

Related U.S. Application Data

(63) Continuation of application No. PCT/US2021/072125, filed on Oct. 29, 2021.
(Continued)

(51) Int. Cl.
*G06T 7/00* (2017.01)
*A61B 5/00* (2006.01)
(Continued)

(52) U.S. Cl.
CPC ............ *G06T 7/0014* (2013.01); *A61B 5/004* (2013.01); *A61B 5/055* (2013.01); *A61B 5/4824* (2013.01);
(Continued)

(58) Field of Classification Search
CPC ..... A61B 5/407; A61B 5/4566; A61B 5/4561; A61B 5/004; G06T 7/0012; G06T 2207/30012
See application file for complete search history.

(56) References Cited

U.S. PATENT DOCUMENTS

| | | | |
|---|---|---|---|
| 3,054,881 A | 9/1962 | Metz et al. | |
| 3,062,876 A | 11/1962 | Pons, Jr. et al. | |

(Continued)

FOREIGN PATENT DOCUMENTS

| | | |
|---|---|---|
| AU | 2012244378 B2 | 5/2015 |
| EP | 0040658 | 12/1981 |

(Continued)

OTHER PUBLICATIONS

A Novel Approach for Treating Chronic Lower Back Pain Abstract for Presentation at North American Spine Society 26th Annual Meeting in Chicago IL on Nov. 4, 2011.
(Continued)

*Primary Examiner* — Molly Wilburn
(74) *Attorney, Agent, or Firm* — Nelson Mullins Riley & Scarborough LLP

(57) ABSTRACT

Described herein are various implementations of systems and methods for determining likelihood of a patient favorably responding to a neuromodulation procedure based on a quantitative or objective score or determination based on a plurality of indicators of pain (e.g., chronic low back pain stemming from one or more vertebral bodies or vertebral endplates of a patient). The systems and methods may involve application of artificial intelligence techniques (e.g., trained algorithms, machine learning or deep learning algorithms, and/or trained neural networks).

19 Claims, 8 Drawing Sheets

Related U.S. Application Data

(60) Provisional application No. 63/129,374, filed on Dec. 22, 2020.

(51) Int. Cl.

| | |
|---|---|
| *A61B 5/055* | (2006.01) |
| *G16H 20/30* | (2018.01) |
| *G16H 30/20* | (2018.01) |

(52) U.S. Cl.
CPC ........... *G06T 7/0012* (2013.01); *G16H 20/30* (2018.01); *G16H 30/20* (2018.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/20081* (2013.01); *G06T 2207/20084* (2013.01); *G06T 2207/30012* (2013.01)

(56)                References Cited

U.S. PATENT DOCUMENTS

| | | |
|---|---|---|
| 3,565,062 A | 2/1971 | Kuris |
| 3,822,708 A | 7/1974 | Zilber |
| 3,845,771 A | 11/1974 | Vise |
| 3,920,021 A | 11/1975 | Hiltebrandt |
| 3,938,502 A | 2/1976 | Born |
| 3,997,408 A | 12/1976 | Barba et al. |
| 4,044,774 A | 8/1977 | Corgin et al. |
| 4,116,198 A | 9/1978 | Roos |
| 4,311,154 A | 1/1982 | Sterzer et al. |
| 4,312,364 A | 1/1982 | Convert et al. |
| 4,378,806 A | 4/1983 | Henley-Cohn |
| 4,448,198 A | 5/1984 | Turner |
| 4,449,528 A | 5/1984 | Auth et al. |
| 4,462,408 A | 7/1984 | Silverstein et al. |
| 4,528,979 A | 7/1985 | Marchenko et al. |
| 4,530,360 A | 7/1985 | Durate |
| 4,541,423 A | 9/1985 | Barber |
| 4,569,351 A | 2/1986 | Tang |
| 4,573,448 A | 3/1986 | Kambin |
| 4,586,512 A | 5/1986 | Do-huu |
| 4,601,296 A | 7/1986 | Yerushalmi |
| 4,612,940 A | 9/1986 | Kasevich et al. |
| 4,657,017 A | 4/1987 | Sorochenko |
| 4,662,383 A | 5/1987 | Sogawa et al. |
| 4,671,293 A | 6/1987 | Shalov |
| 4,676,258 A | 6/1987 | Inokuchi et al. |
| 4,679,561 A | 7/1987 | Doss |
| 4,681,122 A | 7/1987 | Winters et al. |
| 4,750,499 A | 6/1988 | Hoffer |
| 4,754,757 A | 7/1988 | Feucht |
| 4,757,820 A | 7/1988 | Itoh |
| 4,774,967 A | 10/1988 | Zanakis et al. |
| 4,800,899 A | 1/1989 | Elliott |
| 4,813,429 A | 3/1989 | Eshel et al. |
| 4,841,977 A | 6/1989 | Griffith et al. |
| 4,907,589 A | 3/1990 | Cosman |
| 4,924,863 A | 5/1990 | Sterzer |
| 4,936,281 A | 6/1990 | Stasz |
| 4,941,466 A | 7/1990 | Romano |
| 4,950,267 A | 8/1990 | Ishihara et al. |
| 4,951,677 A | 8/1990 | Crowley et al. |
| 4,955,377 A | 9/1990 | Lennox et al. |
| 4,959,063 A | 9/1990 | Kojima |
| 4,961,435 A | 10/1990 | Kitagawa et al. |
| 4,963,142 A | 10/1990 | Loertscher |
| 4,966,144 A | 10/1990 | Rochkind et al. |
| 4,967,765 A | 11/1990 | Turner et al. |
| 4,976,711 A | 12/1990 | Parins et al. |
| 4,977,902 A | 12/1990 | Sekino et al. |
| 5,000,185 A | 3/1991 | Yock |
| 5,002,058 A | 3/1991 | Marinelli |
| 5,002,059 A | 3/1991 | Crowley et al. |
| 5,007,437 A | 4/1991 | Sterzer |
| 5,025,778 A | 6/1991 | Silverstein et al. |
| 5,031,618 A | 7/1991 | Mullett |
| 5,061,266 A | 10/1991 | Hakky |
| 5,070,879 A | 12/1991 | Herres |
| RE33,791 E | 1/1992 | Carr |
| 5,078,736 A | 1/1992 | Behl |
| 5,080,660 A | 1/1992 | Buelna |
| 5,084,043 A | 1/1992 | Hertzmann et al. |
| 5,090,414 A | 2/1992 | Takano |
| 5,098,431 A | 3/1992 | Rydell |
| 5,106,376 A | 4/1992 | Mononen et al. |
| 5,108,404 A | 4/1992 | Scholten et al. |
| 5,131,397 A | 7/1992 | Crowley et al. |
| 5,147,355 A | 9/1992 | Friedman et al. |
| 5,156,157 A | 10/1992 | Valenta, Jr. et al. |
| 5,158,536 A | 10/1992 | Sekins et al. |
| 5,161,533 A | 11/1992 | Prass et al. |
| 5,167,231 A | 12/1992 | Matsui |
| 5,186,177 A | 2/1993 | O'Donnell et al. |
| 5,190,540 A | 3/1993 | Lee |
| 5,190,546 A | 3/1993 | Jervis |
| 5,201,729 A | 4/1993 | Hertzmann et al. |
| 5,207,672 A | 5/1993 | Martinelli et al. |
| 5,209,748 A | 5/1993 | Daikuzono |
| 5,222,953 A | 6/1993 | Dowlatsbabi |
| 5,226,430 A | 7/1993 | Spear et al. |
| 5,242,439 A | 9/1993 | Larsen et al. |
| 5,255,679 A | 10/1993 | Imran |
| 5,271,408 A | 12/1993 | Breyer et al. |
| 5,273,026 A | 12/1993 | Will |
| 5,281,213 A | 1/1994 | Milder et al. |
| 5,281,215 A | 1/1994 | Milder et al. |
| 5,282,468 A | 2/1994 | Klepinski |
| 5,292,321 A | 3/1994 | Lee |
| 5,295,484 A | 3/1994 | Marcus et al. |
| 5,300,085 A | 4/1994 | Yock |
| 5,304,214 A | 4/1994 | DeFord et al. |
| 5,305,756 A | 4/1994 | Entrekin et al. |
| 5,314,463 A | 5/1994 | Camps et al. |
| 5,320,617 A | 6/1994 | Leach |
| 5,324,255 A | 6/1994 | Pasafaro et al. |
| 5,325,860 A | 7/1994 | Seward et al. |
| 5,342,292 A | 8/1994 | Nita et al. |
| 5,342,357 A | 8/1994 | Nardella |
| 5,342,409 A | 8/1994 | Mullett |
| 5,344,435 A | 9/1994 | Turner et al. |
| 5,345,940 A | 9/1994 | Seward et al. |
| 5,348,554 A | 9/1994 | Imran et al. |
| 5,350,377 A | 9/1994 | Winston et al. |
| 5,351,691 A | 10/1994 | Brommersma |
| 5,366,443 A | 11/1994 | Eggers et al. |
| 5,366,490 A | 11/1994 | Edwards et al. |
| 5,368,031 A | 11/1994 | Cline et al. |
| 5,368,035 A | 11/1994 | Hamm et al. |
| 5,368,557 A | 11/1994 | Nita et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Crowley et al. |
| 5,374,265 A | 12/1994 | Sand |
| 5,383,876 A | 1/1995 | Nardella |
| 5,385,148 A | 1/1995 | Lesh et al. |
| 5,385,544 A | 1/1995 | Edwards et al. |
| 5,391,197 A | 2/1995 | Burdette et al. |
| 5,391,199 A | 2/1995 | Ben-Haim |
| 5,405,376 A | 4/1995 | Mulier et al. |
| 5,411,527 A | 5/1995 | Alt |
| 5,417,719 A | 5/1995 | Hull et al. |
| 5,419,767 A | 5/1995 | Eggers et al. |
| 5,421,338 A | 6/1995 | Crowley |
| 5,423,811 A | 6/1995 | Imran et al. |
| 5,431,649 A | 7/1995 | Mulier et al. |
| 5,433,739 A | 7/1995 | Sluijter et al. |
| D361,555 S | 8/1995 | Bettin et al. |
| 5,437,661 A | 8/1995 | Rieser |
| 5,441,499 A | 8/1995 | Fritzsch |
| 5,441,527 A | 8/1995 | Erickson et al. |
| 5,443,463 A | 8/1995 | Stern et al. |
| 5,447,509 A | 9/1995 | Millis et al. |

(56)                References Cited

U.S. PATENT DOCUMENTS

| | | |
|---|---|---|
| 5,449,380 A | 9/1995 | Chin |
| 5,454,373 A | 10/1995 | Koger et al. |
| 5,458,596 A | 10/1995 | Lax et al. |
| 5,458,597 A | 10/1995 | Edwards et al. |
| 5,471,988 A | 12/1995 | Fujio et al. |
| 5,472,441 A | 12/1995 | Edwards et al. |
| 5,474,530 A | 12/1995 | Passafaro et al. |
| 5,484,432 A | 1/1996 | Sand |
| 5,486,170 A | 1/1996 | Winston et al. |
| 5,501,703 A | 3/1996 | Holsheimer et al. |
| 5,505,730 A | 4/1996 | Edwards |
| 5,514,130 A | 5/1996 | Baker |
| 5,524,624 A | 6/1996 | Tepper et al. |
| 5,526,815 A | 6/1996 | Granz et al. |
| 5,529,580 A | 6/1996 | Hagino et al. |
| 5,540,679 A | 7/1996 | Fram et al. |
| 5,540,681 A | 7/1996 | Strul et al. |
| 5,540,684 A | 7/1996 | Hassler, Jr. |
| 5,545,161 A | 8/1996 | Imran |
| 5,560,362 A | 10/1996 | Silwa, Jr. et al. |
| 5,565,005 A | 10/1996 | Erickson et al. |
| 5,569,242 A | 10/1996 | Lax et al. |
| 5,571,088 A | 11/1996 | Lennox et al. |
| 5,571,147 A | 11/1996 | Sluijter et al. |
| 5,575,772 A | 11/1996 | Lennox |
| 5,575,788 A | 11/1996 | Baker et al. |
| 5,588,432 A | 12/1996 | Crowley |
| 5,596,988 A | 1/1997 | Markle et al. |
| 5,601,526 A | 2/1997 | Chapelon et al. |
| 5,606,974 A | 3/1997 | Castellano et al. |
| 5,609,151 A | 3/1997 | Mulier et al. |
| 5,620,479 A | 4/1997 | Diederich |
| 5,628,317 A | 5/1997 | Starkebaum et al. |
| 5,630,426 A | 5/1997 | Shmulewitz et al. |
| 5,630,837 A | 5/1997 | Crowley |
| 5,643,319 A | 7/1997 | Green et al. |
| 5,643,330 A | 7/1997 | Holshiemer et al. |
| 5,647,361 A | 7/1997 | Damadian |
| 5,647,871 A | 7/1997 | Levine et al. |
| 5,658,278 A | 8/1997 | Imran et al. |
| 5,672,173 A | 9/1997 | Gough et al. |
| 5,681,282 A | 10/1997 | Eggers et al. |
| 5,683,366 A | 11/1997 | Eggers et al. |
| 5,685,839 A | 11/1997 | Baker et al. |
| 5,687,729 A | 11/1997 | Schaetzle |
| 5,688,267 A | 11/1997 | Panescu |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,718,231 A | 2/1998 | Chen et al. |
| 5,720,286 A | 2/1998 | Chapelon et al. |
| 5,720,287 A | 2/1998 | Chapelon et al. |
| 5,722,403 A | 3/1998 | McGee et al. |
| 5,725,494 A | 3/1998 | Brisken |
| 5,728,062 A | 3/1998 | Brisken |
| 5,730,706 A | 3/1998 | Garnies |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Fleischman et al. |
| 5,735,847 A | 4/1998 | Gough et al. |
| 5,738,680 A | 4/1998 | Mueller et al. |
| 5,741,249 A | 4/1998 | Moss et al. |
| 5,743,904 A | 4/1998 | Edwards |
| 5,746,737 A | 5/1998 | Saadat |
| 5,752,969 A | 5/1998 | Cunci et al. |
| 5,755,663 A | 5/1998 | Johnson et al. |
| 5,762,066 A | 6/1998 | Law et al. |
| 5,762,616 A | 6/1998 | Talish |
| 5,766,153 A | 6/1998 | Eggers et al. |
| 5,766,231 A | 6/1998 | Erickson et al. |
| 5,776,092 A | 7/1998 | Farin et al. |
| 5,785,705 A | 7/1998 | Baker |
| 5,800,378 A | 9/1998 | Edwards et al. |
| 5,800,429 A | 9/1998 | Edwards |
| 5,800,432 A | 9/1998 | Swanson |
| 5,807,237 A | 9/1998 | Tindel |
| 5,807,391 A | 9/1998 | Wijkamp |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,824,021 A | 10/1998 | Rise |
| 5,840,031 A | 11/1998 | Crowley |
| 5,843,019 A | 12/1998 | Eggers et al. |
| 5,843,021 A | 12/1998 | Edwards et al. |
| 5,844,092 A | 12/1998 | Presta et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,865,801 A | 2/1999 | Houser |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,876,398 A | 3/1999 | Mulier et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,902,308 A | 5/1999 | Murphy |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,972,015 A | 10/1999 | Scribner et al. |
| 5,976,105 A | 11/1999 | Marcove et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,014,588 A | 1/2000 | Fitz |
| 6,016,452 A | 1/2000 | Kasevich |
| 6,016,809 A | 1/2000 | Mulier et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Lesh et al. |
| 6,030,374 A | 2/2000 | McDaniel |
| 6,030,402 A | 2/2000 | Thompson et al. |
| 6,032,673 A | 3/2000 | Langberg et al. |
| 6,032,674 A | 3/2000 | Eggers et al. |
| 6,033,411 A | 3/2000 | Preissman et al. |
| 6,035,238 A | 3/2000 | Ingle et al. |
| 6,038,480 A | 3/2000 | Hrdlicka et al. |
| 6,045,532 A | 4/2000 | Eggers et al. |
| 6,046,187 A | 4/2000 | Berde et al. |
| 6,047,214 A | 4/2000 | Mueller et al. |
| 6,050,995 A | 4/2000 | Durgin |
| 6,053,172 A | 4/2000 | Hovda et al. |
| 6,053,909 A | 4/2000 | Shadduck |

(56)                    References Cited

U.S. PATENT DOCUMENTS

| | | | |
|---|---|---|---|
| 6,056,745 A | 5/2000 | Panescu et al. |
| 6,063,078 A | 5/2000 | Wittkampf |
| 6,063,079 A | 5/2000 | Hovda et al. |
| 6,066,134 A | 5/2000 | Eggers et al. |
| 6,066,139 A | 5/2000 | Ryan et al. |
| 6,068,642 A | 5/2000 | Johnson et al. |
| 6,071,279 A | 6/2000 | Whayne et al. |
| 6,073,051 A | 6/2000 | Sharkey et al. |
| 6,074,352 A | 6/2000 | Hynynen et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Ciamacco |
| 6,099,514 A | 8/2000 | Sharkey et al. |
| 6,099,524 A | 8/2000 | Lipson et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,112,122 A | 8/2000 | Schwardt et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,120,502 A | 9/2000 | Michelson |
| 6,122,549 A | 9/2000 | Sharkey et al. |
| 6,126,682 A | 10/2000 | Ashley et al. |
| 6,137,209 A | 10/2000 | Dahlberg et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sharkey et al. |
| 6,169,924 B1 | 1/2001 | Meloy et al. |
| 6,171,239 B1 | 1/2001 | Humphrey |
| 6,176,857 B1 | 1/2001 | Ashley |
| 6,179,824 B1 | 1/2001 | Eggers et al. |
| 6,179,836 B1 | 1/2001 | Eggers et al. |
| 6,179,858 B1 | 1/2001 | Squire et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,216,704 B1 | 4/2001 | Ingle et al. |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,516 B1 | 5/2001 | Keilman et al. |
| 6,231,528 B1 | 5/2001 | Kaufman et al. |
| 6,231,571 B1 | 5/2001 | Ellman et al. |
| 6,231,615 B1 | 5/2001 | Preissman |
| 6,233,488 B1 | 5/2001 | Hess |
| 6,235,020 B1 | 5/2001 | Cheng et al. |
| 6,235,022 B1 | 5/2001 | Hallock et al. |
| 6,235,024 B1 | 5/2001 | Tu |
| 6,237,604 B1 | 5/2001 | Burnside et al. |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,241,734 B1 | 6/2001 | Scribner et al. |
| 6,245,064 B1 | 6/2001 | Lesh et al. |
| 6,246,912 B1 | 6/2001 | Sluijter et al. |
| 6,248,110 B1 | 6/2001 | Reiley et al. |
| 6,248,345 B1 | 6/2001 | Goldenheim et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,270,498 B1 | 8/2001 | Michelson |
| 6,277,112 B1 | 8/2001 | Underwood et al. |
| 6,277,122 B1 | 8/2001 | McGahan et al. |
| 6,280,441 B1 | 8/2001 | Ryan |
| 6,280,456 B1 | 8/2001 | Scribner et al. |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,292,699 B1 | 9/2001 | Simon et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,425 B1 | 11/2001 | Simpson et al. |
| 6,312,426 B1 | 11/2001 | Goldberg et al. |
| 6,319,241 B1 | 11/2001 | King et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,361,531 B1 | 3/2002 | Hissong |
| 6,363,937 B1 | 4/2002 | Hovda et al. |
| 6,368,292 B1 | 4/2002 | Ogden et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,398,782 B1 | 6/2002 | Pecor et al. |
| 6,416,507 B1 | 7/2002 | Eggers et al. |
| 6,416,508 B1 | 7/2002 | Eggers et al. |
| 6,423,057 B1 | 7/2002 | He et al. |
| 6,423,059 B1 | 7/2002 | Hanson et al. |
| 6,425,887 B1 | 7/2002 | McGuckin et al. |
| 6,426,339 B1 | 7/2002 | Berde et al. |
| 6,428,491 B1 | 8/2002 | Weiss |
| 6,432,103 B1 | 8/2002 | Ellsberry et al. |
| 6,436,060 B1 | 8/2002 | Talish |
| 6,436,098 B1 | 8/2002 | Michelson |
| 6,440,138 B1 | 8/2002 | Reiley et al. |
| 6,447,448 B1 | 9/2002 | Ishikawa et al. |
| 6,451,013 B1 | 9/2002 | Bays et al. |
| 6,454,727 B1 | 9/2002 | Bubank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,470,220 B1 | 10/2002 | Kraus et al. |
| 6,478,793 B1 | 11/2002 | Cosman et al. |
| 6,482,201 B1 | 11/2002 | Olsen et al. |
| 6,485,271 B1 | 11/2002 | Tack |
| 6,487,446 B1 | 11/2002 | Hill et al. |
| 6,491,893 B1 | 12/2002 | Babich |
| 6,493,592 B1 | 12/2002 | Leonard et al. |
| 6,494,902 B2 | 12/2002 | Hoey et al. |
| 6,500,173 B2 | 12/2002 | Underwood et al. |
| 6,505,075 B1 | 1/2003 | Weiner |
| 6,508,839 B1 | 1/2003 | Lambrecht et al. |
| 6,524,261 B2 | 2/2003 | Talish et al. |

(56) References Cited

U.S. PATENT DOCUMENTS

| | | |
|---|---|---|
| 6,527,759 B1 | 3/2003 | Tachibana et al. |
| 6,537,306 B1 | 3/2003 | Burdette et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,558,390 B2 | 5/2003 | Cragg |
| 6,560,486 B1 | 5/2003 | Osorio et al. |
| 6,562,033 B2 | 5/2003 | Shah et al. |
| 6,575,919 B1 | 6/2003 | Reiley et al. |
| 6,575,968 B1 | 6/2003 | Eggers et al. |
| 6,575,969 B1 | 6/2003 | Rittman, III et al. |
| 6,575,979 B1 | 6/2003 | Cragg |
| 6,578,579 B2 | 6/2003 | Burnside et al. |
| 6,582,423 B1 | 6/2003 | Thapliyal et al. |
| 6,585,656 B2 | 7/2003 | Masters |
| 6,589,237 B2 | 7/2003 | Woloszko et al. |
| 6,592,559 B1 | 7/2003 | Pakter et al. |
| 6,595,990 B1 | 7/2003 | Weinstein et al. |
| 6,599,288 B2 | 7/2003 | Maguire et al. |
| 6,602,248 B1 | 8/2003 | Sharps et al. |
| 6,604,003 B2 | 8/2003 | Fredricks et al. |
| 6,607,502 B1 | 8/2003 | Maguire et al. |
| 6,607,529 B1 | 8/2003 | Jones et al. |
| 6,608,502 B2 | 8/2003 | Aoki et al. |
| 6,622,731 B2 | 9/2003 | Daniel et al. |
| 6,623,505 B2 | 9/2003 | Scribner et al. |
| 6,632,193 B1 | 10/2003 | Davison et al. |
| 6,632,220 B1 | 10/2003 | Eggers et al. |
| 6,645,202 B1 | 11/2003 | Pless et al. |
| 6,648,883 B2 | 11/2003 | Francischelli et al. |
| 6,651,669 B1 | 11/2003 | Burnside |
| 6,659,106 B1 | 12/2003 | Hovda et al. |
| 6,663,627 B2 | 12/2003 | Francischelli et al. |
| 6,663,647 B2 | 12/2003 | Reiley et al. |
| 6,673,063 B2 | 1/2004 | Brett |
| 6,689,086 B1 | 2/2004 | Nita et al. |
| 6,689,125 B1 | 2/2004 | Keith et al. |
| 6,692,450 B1 | 2/2004 | Coleman |
| 6,699,240 B2 | 3/2004 | Francischelli |
| 6,699,242 B2 | 3/2004 | Heggeness |
| 6,709,432 B2 | 3/2004 | Ferek-Patric |
| 6,718,208 B2 | 4/2004 | Hill et al. |
| 6,719,761 B1 | 4/2004 | Reiley et al. |
| 6,723,087 B2 | 4/2004 | O'Neill et al. |
| 6,723,094 B1 | 4/2004 | Desinger |
| 6,726,684 B1 | 4/2004 | Woloszko et al. |
| 6,736,810 B2 | 5/2004 | Hoey et al. |
| 6,736,835 B2 | 5/2004 | Pelegrino et al. |
| 6,745,079 B2 | 6/2004 | King |
| 6,746,447 B2 | 6/2004 | Davison et al. |
| 6,746,451 B2 | 6/2004 | Middleton et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,795,737 B2 | 9/2004 | Gielen et al. |
| 6,805,697 B1 | 10/2004 | Helm et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Eick et al. |
| 6,960,204 B2 | 11/2005 | Eggers et al. |
| 6,962,589 B2 | 11/2005 | Mulier et al. |
| 6,974,453 B2 | 12/2005 | Woloszko et al. |
| 6,980,849 B2 | 12/2005 | Sasso |
| 6,981,981 B2 | 1/2006 | Reiley et al. |
| 6,989,010 B2 | 1/2006 | Francischelli et al. |
| 6,997,941 B2 | 2/2006 | Sharkey et al. |
| 7,001,383 B2 | 2/2006 | Keidar |
| 7,041,096 B2 | 5/2006 | Malis et al. |
| 7,044,954 B2 | 5/2006 | Reiley et al. |
| 7,048,743 B2 | 5/2006 | Miller et al. |
| 7,065,408 B2 | 6/2006 | Herman et al. |
| 7,081,122 B1 | 7/2006 | Reiley et al. |
| 7,090,672 B2 | 8/2006 | Underwood et al. |
| 7,094,215 B2 | 8/2006 | Davison et al. |
| 7,104,989 B2 | 9/2006 | Skarda |
| 7,118,574 B2 | 10/2006 | Patel et al. |
| 7,131,969 B1 | 11/2006 | Hovda et al. |
| 7,153,307 B2 | 12/2006 | Scribner et al. |
| 7,163,536 B2 | 1/2007 | Godara |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,238,184 B2 | 7/2007 | Megerman et al. |
| 7,241,297 B2 | 7/2007 | Shaolian et al. |
| 7,250,048 B2 | 7/2007 | Francischelli et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,306,598 B2 | 12/2007 | Truckai et al. |
| 7,318,823 B2 | 1/2008 | Sharps et al. |
| 7,318,826 B2 | 1/2008 | Teitelbaum et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,399,306 B2 | 7/2008 | Reiley et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,503,921 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,553,309 B2 | 6/2009 | Buysse et al. |
| 7,555,343 B2 | 6/2009 | Bleich |
| 7,559,932 B2 | 7/2009 | Truckai et al. |
| 7,569,626 B2 | 8/2009 | Truckai |
| 7,574,257 B2 | 8/2009 | Rittman, III |
| 7,585,300 B2 | 9/2009 | Cha |
| 7,593,778 B2 | 9/2009 | Chandran et al. |
| 7,594,913 B2 | 9/2009 | Ormsby et al. |
| 7,604,636 B1 | 10/2009 | Walters et al. |
| 7,621,952 B2 | 11/2009 | Truckai et al. |
| 7,645,277 B2 | 1/2010 | McClurken et al. |
| 7,678,111 B2 | 3/2010 | Mulier et al. |
| 7,678,116 B2 | 3/2010 | Truckai et al. |
| 7,682,378 B2 | 3/2010 | Truckai et al. |
| 7,708,733 B2 | 5/2010 | Sanders et al. |

(56) References Cited

U.S. PATENT DOCUMENTS

| | | | |
|---|---|---|---|
| 7,717,918 B2 | 5/2010 | Truckai et al. |
| 7,722,620 B2 | 5/2010 | Truckai et al. |
| 7,731,720 B2 | 6/2010 | Sand et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,749,220 B2 | 7/2010 | Schmaltz et al. |
| 7,780,733 B2 | 8/2010 | Carver et al. |
| 7,792,588 B2 | 9/2010 | Harding |
| 7,799,021 B2 | 9/2010 | Leung et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,828,804 B2 | 11/2010 | Li et al. |
| 7,846,156 B2 | 12/2010 | Malis et al. |
| 7,850,685 B2 | 12/2010 | Kunis et al. |
| 7,853,326 B2 | 12/2010 | Rittman, III |
| 7,857,813 B2 | 12/2010 | Schmitz et al. |
| 7,879,032 B1 | 2/2011 | Garito et al. |
| 7,887,534 B2 | 2/2011 | Hamel et al. |
| 7,887,543 B2 | 2/2011 | Sand et al. |
| 7,892,235 B2 | 2/2011 | Ellis |
| 7,896,870 B2 | 3/2011 | Arless et al. |
| 7,896,909 B2 | 3/2011 | Sharkey et al. |
| 7,901,403 B2 | 3/2011 | Woloszko et al. |
| 7,909,827 B2 | 3/2011 | Reiley et al. |
| 7,909,873 B2 | 3/2011 | Tan-Malecki et al. |
| 7,914,526 B2 | 3/2011 | Lehmann et al. |
| 7,914,535 B2 | 3/2011 | Assell et al. |
| 7,917,222 B1 | 3/2011 | Osorio et al. |
| 7,918,849 B2 | 4/2011 | Bleich et al. |
| 7,918,874 B2 | 4/2011 | Siegal |
| 7,938,835 B2 | 5/2011 | Boucher et al. |
| 7,945,331 B2 | 5/2011 | Vilims |
| 7,951,140 B2 | 5/2011 | Arless et al. |
| 7,959,634 B2 | 6/2011 | Sennett |
| 7,963,915 B2 | 6/2011 | Bleich |
| 7,967,827 B2 | 6/2011 | Osorio et al. |
| 7,972,340 B2 | 7/2011 | Sand et al. |
| 8,000,785 B2 | 8/2011 | Ritmann, III |
| 8,021,401 B2 | 9/2011 | Carl et al. |
| 8,025,688 B2 | 9/2011 | Diederich et al. |
| 8,034,052 B2 | 10/2011 | Podhajsky |
| 8,034,071 B2 | 10/2011 | Scribner et al. |
| 8,043,287 B2 | 10/2011 | Conquergood et al. |
| 8,048,030 B2 | 11/2011 | McGuckin, Jr. et al. |
| 8,048,071 B2 | 11/2011 | Youssef et al. |
| 8,048,083 B2 | 11/2011 | Shadduck et al. |
| 8,052,661 B2 | 11/2011 | McGuckin, Jr. et al. |
| 8,062,290 B2 | 11/2011 | Buysse et al. |
| 8,066,702 B2 | 11/2011 | Rittman, III et al. |
| 8,066,712 B2 | 11/2011 | Truckai et al. |
| 8,070,753 B2 | 12/2011 | Truckai et al. |
| 8,082,043 B2 | 12/2011 | Sharkey et al. |
| 8,083,736 B2 | 12/2011 | McClurken et al. |
| 8,092,456 B2 | 1/2012 | Bleich et al. |
| 8,096,957 B2 | 1/2012 | Conquergood et al. |
| 8,100,896 B2 | 1/2012 | Podhajsky |
| 8,109,933 B2 | 2/2012 | Truckai et al. |
| 8,123,750 B2 | 2/2012 | Norton et al. |
| 8,123,756 B2 | 2/2012 | Miller et al. |
| 8,128,619 B2 | 3/2012 | Sharkey et al. |
| 8,128,633 B2 | 3/2012 | Linderman et al. |
| 8,162,933 B2 | 4/2012 | Francischelli et al. |
| 8,163,031 B2 | 4/2012 | Truckai et al. |
| 8,172,846 B2 | 5/2012 | Brunnett et al. |
| 8,182,477 B2 | 5/2012 | Orszulak et al. |
| 8,187,268 B2 | 5/2012 | Godara et al. |
| 8,187,312 B2 | 5/2012 | Sharkey et al. |
| 8,192,424 B2 | 6/2012 | Woloszko et al. |
| 8,192,435 B2 | 6/2012 | Bleich et al. |
| 8,192,442 B2 | 6/2012 | Truckai et al. |
| 8,216,223 B2 | 7/2012 | Wham et al. |
| 8,226,697 B2 | 7/2012 | Sharkey et al. |
| 8,231,616 B2 | 7/2012 | McPherson et al. |
| 8,241,335 B2 | 8/2012 | Truckai et al. |
| 8,246,627 B2 | 8/2012 | Vanleeuwen et al. |
| 8,265,747 B2 | 9/2012 | Rittman, III et al. |
| 8,282,628 B2 | 10/2012 | Paul et al. |
| 8,292,882 B2 | 10/2012 | Danek et al. |
| 8,292,887 B2 | 10/2012 | Woloszko et al. |
| 8,323,277 B2 | 12/2012 | Vilims |
| 8,323,279 B2 | 12/2012 | Dahla et al. |
| 8,343,146 B2 | 1/2013 | Godara et al. |
| 8,348,946 B2 | 1/2013 | McClurken et al. |
| 8,348,955 B2 | 1/2013 | Truckai et al. |
| 8,355,799 B2 | 1/2013 | Marion et al. |
| 8,361,063 B2 | 1/2013 | Godara |
| 8,361,067 B2 | 1/2013 | Pellegrino et al. |
| 8,406,886 B2 | 3/2013 | Gaunt et al. |
| 8,409,289 B2 | 4/2013 | Truckai et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,430 B2 | 4/2013 | Pond, Jr. et al. |
| 8,425,507 B2 | 4/2013 | Pellegrino et al. |
| 8,430,881 B2 | 4/2013 | Bleich et al. |
| 8,430,887 B2 | 4/2013 | Truckai et al. |
| 8,444,636 B2 | 5/2013 | Shadduck et al. |
| 8,444,640 B2 | 5/2013 | Demarais et al. |
| 8,454,594 B2 | 6/2013 | Demarais et al. |
| 8,460,382 B2 | 6/2013 | Helm et al. |
| 8,475,449 B2 | 7/2013 | Werneth et al. |
| 8,486,063 B2 | 7/2013 | Werneth et al. |
| 8,487,021 B2 | 7/2013 | Truckai et al. |
| 8,504,147 B2 | 8/2013 | Deem et al. |
| 8,505,545 B2 | 8/2013 | Conquergood et al. |
| 8,518,036 B2 | 8/2013 | Leung et al. |
| 8,523,871 B2 | 9/2013 | Truckai et al. |
| 8,535,309 B2 | 9/2013 | Pellegrino et al. |
| 8,540,723 B2 | 9/2013 | Shadduck et al. |
| 8,556,891 B2 | 10/2013 | Mathur |
| 8,556,910 B2 | 10/2013 | Truckai et al. |
| 8,556,911 B2 | 10/2013 | Mehta et al. |
| 8,560,062 B2 | 10/2013 | Rittman, III et al. |
| 8,562,598 B2 | 10/2013 | Falkenstein et al. |
| 8,562,607 B2 | 10/2013 | Truckai et al. |
| 8,562,620 B2 | 10/2013 | Truckai et al. |
| 8,579,903 B2 | 11/2013 | Carl |
| 8,585,694 B2 | 11/2013 | Amoah et al. |
| 8,591,507 B2 | 11/2013 | Kramer et al. |
| 8,597,301 B2 | 12/2013 | Mitchell |
| 8,603,088 B2 | 12/2013 | Stern et al. |
| 8,613,744 B2 | 12/2013 | Pellegrino et al. |
| 8,617,156 B2 | 12/2013 | Werneth et al. |
| 8,623,014 B2 | 1/2014 | Pellegrino et al. |
| 8,623,025 B2 | 1/2014 | Tan-Malecki et al. |
| 8,628,528 B2 | 1/2014 | Pellegrino et al. |
| 8,636,736 B2 | 1/2014 | Yates et al. |
| 8,644,941 B2 | 2/2014 | Rooney et al. |
| 8,657,814 B2 | 2/2014 | Werneth et al. |
| 8,663,266 B1 | 3/2014 | Obsuth |
| 8,672,934 B2 | 3/2014 | Benamou et al. |
| 8,676,309 B2 | 3/2014 | Deem et al. |
| 8,679,023 B2 | 3/2014 | Kobayashi et al. |
| 8,690,884 B2 | 4/2014 | Linderman et al. |
| 8,696,679 B2 | 4/2014 | Shadduck et al. |
| RE44,883 E | 5/2014 | Cha |
| 8,740,897 B2 | 6/2014 | Leung et al. |
| 8,747,359 B2 | 6/2014 | Pakter et al. |
| 8,747,398 B2 | 6/2014 | Behnke |
| 8,758,349 B2 | 6/2014 | Germain et al. |
| 8,764,761 B2 | 7/2014 | Truckai et al. |
| 8,771,265 B2 | 7/2014 | Truckai |
| 8,771,276 B2 | 7/2014 | Linderman |
| 8,774,913 B2 | 7/2014 | Demarais et al. |
| 8,774,924 B2 | 7/2014 | Weiner |
| 8,777,479 B2 | 7/2014 | Kwan et al. |
| 8,784,411 B2 | 7/2014 | Leuthardt et al. |
| 8,795,270 B2 | 8/2014 | Drake |
| 8,808,161 B2 | 8/2014 | Gregg et al. |
| 8,808,284 B2 | 8/2014 | Pellegrino et al. |

(56) References Cited

U.S. PATENT DOCUMENTS

| | | | |
|---|---|---|---|
| 8,814,873 B2 | 8/2014 | Schaller et al. |
| 8,818,503 B2 | 8/2014 | Rittman, III |
| 8,821,488 B2 | 9/2014 | Stewart et al. |
| 8,828,001 B2 | 9/2014 | Stearns et al. |
| 8,845,631 B2 | 9/2014 | Werneth et al. |
| 8,864,759 B2 | 10/2014 | Godara et al. |
| 8,864,760 B2 | 10/2014 | Kramer et al. |
| 8,864,777 B2 | 10/2014 | Harrison et al. |
| 8,880,189 B2 | 11/2014 | Lipani |
| 8,882,755 B2 | 11/2014 | Leung et al. |
| 8,882,759 B2 | 11/2014 | Manley et al. |
| 8,882,764 B2 | 11/2014 | Pellegrino et al. |
| 8,894,616 B2 | 11/2014 | Harrison et al. |
| 8,894,658 B2 | 11/2014 | Linderman et al. |
| 8,911,497 B2 | 12/2014 | Chavatte et al. |
| 8,915,949 B2 | 12/2014 | Diederich et al. |
| 8,926,620 B2 | 1/2015 | Chasmawala et al. |
| 8,932,300 B2 | 1/2015 | Shadduck et al. |
| 8,939,969 B2 | 1/2015 | Temelli et al. |
| 8,968,288 B2 | 3/2015 | Brannan |
| 8,989,859 B2 | 3/2015 | Deem et al. |
| 8,992,521 B2 | 3/2015 | VanWyk |
| 8,992,522 B2 | 3/2015 | Pellegrino et al. |
| 8,992,523 B2 | 3/2015 | Pellegrino et al. |
| 8,992,524 B1 | 3/2015 | Ellman |
| 9,005,210 B2 | 4/2015 | Truckai et al. |
| 9,008,793 B1 | 4/2015 | Cosman, Sr. et al. |
| 9,017,325 B2 | 4/2015 | Pellegrino et al. |
| 9,023,038 B2 | 5/2015 | Pellegrino et al. |
| 9,028,488 B2 | 5/2015 | Gosbayesbgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,050,109 B2 | 6/2015 | Smith |
| 9,050,112 B2 | 6/2015 | Greenhalgh et al. |
| 9,066,769 B2 | 6/2015 | Truckai et al. |
| 9,078,761 B2 | 7/2015 | Godara et al. |
| 9,095,359 B2 | 8/2015 | Robert et al. |
| 9,113,896 B2 | 8/2015 | Mulier et al. |
| 9,113,911 B2 | 8/2015 | Sherman |
| 9,113,925 B2 | 8/2015 | Smith et al. |
| 9,113,950 B2 | 8/2015 | Schutlz et al. |
| 9,113,974 B2 | 8/2015 | Germain |
| 9,119,623 B2 | 9/2015 | Malis et al. |
| 9,119,639 B2 | 9/2015 | Kuntz |
| 9,119,647 B2 | 9/2015 | Brannan |
| 9,119,650 B2 | 9/2015 | Brannan et al. |
| 9,125,671 B2 | 9/2015 | Germain et al. |
| 9,131,597 B2 | 9/2015 | Taft et al. |
| 9,149,652 B2 | 10/2015 | Wenz et al. |
| 9,151,680 B2 | 10/2015 | Brannan |
| 9,155,895 B2 | 10/2015 | Wacnik et al. |
| 9,161,735 B2 | 10/2015 | Bradford et al. |
| 9,161,797 B2 | 10/2015 | Truckai et al. |
| 9,161,798 B2 | 10/2015 | Truckai et al. |
| 9,161,805 B2 | 10/2015 | Isenberg |
| 9,161,809 B2 | 10/2015 | Germain et al. |
| 9,161,814 B2 | 10/2015 | Brannan et al. |
| 9,168,047 B2 | 10/2015 | To et al. |
| 9,168,054 B2 | 10/2015 | Turner et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,179,972 B2 | 11/2015 | Olson |
| 9,180,416 B2 | 11/2015 | Phan et al. |
| 9,186,197 B2 | 11/2015 | McKay |
| 9,192,308 B2 | 11/2015 | Brannan et al. |
| 9,192,397 B2 | 11/2015 | Sennett et al. |
| 9,198,684 B2 | 12/2015 | Arthur et al. |
| 9,216,053 B2 | 12/2015 | Godara et al. |
| 9,216,195 B2 | 12/2015 | Truckai et al. |
| 9,226,756 B2 | 1/2016 | Teisen et al. |
| 9,232,954 B2 | 1/2016 | Steiner et al. |
| 9,237,916 B2 | 1/2016 | Crainich et al. |
| 9,238,139 B2 | 1/2016 | Degiorgio et al. |
| 9,241,057 B2 | 1/2016 | Van Wyk et al. |
| 9,241,729 B2 | 1/2016 | Juntz et al. |
| 9,241,760 B2 | 1/2016 | Godara et al. |
| 9,247,970 B2 | 2/2016 | Teisen |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,979 B2 | 3/2016 | O'Neil et al. |
| 9,282,988 B2 | 3/2016 | Goshayeshgar |
| 9,283,015 B2 | 3/2016 | Tan-Malecki et al. |
| 9,289,607 B2 | 3/2016 | Su et al. |
| 9,295,479 B2 | 3/2016 | Hibri et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashiach |
| 9,314,618 B2 | 4/2016 | Imran et al. |
| 9,333,033 B2 | 5/2016 | Gliner |
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |
| 9,345,537 B2 | 5/2016 | Harrison et al. |
| 9,345,538 B2 | 5/2016 | Deem et al. |
| 9,351,739 B2 | 5/2016 | Mahoney et al. |
| 9,358,059 B2 | 6/2016 | Linderman et al. |
| 9,358,067 B2 | 6/2016 | Lee et al. |
| 9,358,396 B2 | 6/2016 | Holley |
| 9,364,242 B2 | 6/2016 | Tornier et al. |
| 9,364,286 B2 | 6/2016 | Werneth et al. |
| 9,370,348 B2 | 6/2016 | Tally et al. |
| 9,370,373 B2 | 6/2016 | Smith |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Robert et al. |
| 9,375,279 B2 | 6/2016 | Brannan |
| 9,375,283 B2 | 6/2016 | Arts et al. |
| 9,381,024 B2 | 7/2016 | Globerman et al. |
| 9,381,045 B2 | 7/2016 | Donner et al. |
| 9,381,050 B2 | 7/2016 | Lee et al. |
| 9,381,359 B2 | 7/2016 | Parramon et al. |
| 9,387,094 B2 | 7/2016 | Manrique et al. |
| 9,393,416 B2 | 7/2016 | Rooney et al. |
| 9,398,931 B2 | 7/2016 | Wittenberger et al. |
| 9,399,144 B2 | 7/2016 | Howard |
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,057 B2 | 8/2016 | Germain |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,439,693 B2 | 9/2016 | Childs et al. |
| 9,439,721 B2 | 9/2016 | Werneth et al. |

(56) References Cited

U.S. PATENT DOCUMENTS

| | | | |
|---|---|---|---|
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,565 B2 | 10/2016 | Shikhman et al. |
| 9,474,906 B2 | 10/2016 | Sachs et al. |
| 9,480,485 B2 | 11/2016 | Aho et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |
| 9,492,664 B2 | 11/2016 | Peterson |
| 9,504,372 B2 | 11/2016 | Kim |
| 9,504,481 B2 | 11/2016 | Germain et al. |
| 9,504,506 B2 | 11/2016 | Crainich et al. |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,513,761 B2 | 12/2016 | Shikhman et al. |
| 9,517,077 B2 | 12/2016 | Blain et al. |
| 9,517,200 B2 | 12/2016 | Bleier |
| 9,526,507 B2 | 12/2016 | Germain |
| 9,526,551 B2 | 12/2016 | Linderman |
| 9,526,559 B2 | 12/2016 | Banamou et al. |
| 9,532,828 B2 | 1/2017 | Condie et al. |
| 9,545,283 B2 | 1/2017 | Sack et al. |
| 9,549,772 B2 | 1/2017 | Carl |
| 9,550,041 B2 | 1/2017 | Bedell |
| 9,555,037 B2 | 1/2017 | Podhajsky |
| 9,556,101 B2 | 1/2017 | Robertson et al. |
| 9,556,449 B2 | 1/2017 | Basu et al. |
| 9,566,108 B2 | 2/2017 | Brustad et al. |
| 9,566,449 B2 | 2/2017 | Perryman et al. |
| 9,572,976 B2 | 2/2017 | Howard et al. |
| 9,572,986 B2 | 2/2017 | Moffitt |
| 9,579,127 B2 | 2/2017 | Kostuik et al. |
| 9,579,518 B2 | 2/2017 | Gertner |
| 9,597,091 B2 | 3/2017 | Bromer |
| 9,597,148 B2 | 3/2017 | Olson |
| RE46,356 E | 4/2017 | Pellegrino et al. |
| 9,610,083 B2 | 4/2017 | Kuntz |
| 9,610,117 B2 | 4/2017 | Germain |
| 9,636,175 B2 | 5/2017 | Stern et al. |
| 9,642,629 B2 | 5/2017 | Griffiths et al. |
| 9,649,116 B2 | 5/2017 | Germain |
| 9,675,408 B2 | 6/2017 | Godara et al. |
| 9,681,889 B1 | 6/2017 | Greenhalgh et al. |
| 9,687,255 B2 | 6/2017 | Sennett et al. |
| 9,717,551 B2 | 8/2017 | Krueger et al. |
| 9,724,107 B2 | 8/2017 | Pellegrino et al. |
| 9,724,151 B2 | 8/2017 | Edidin |
| 9,730,707 B2 | 8/2017 | Sasaki et al. |
| 9,743,854 B2 | 8/2017 | Stewart et al. |
| 9,743,938 B2 | 8/2017 | Germain et al. |
| 9,750,560 B2 | 9/2017 | Ballakur et al. |
| 9,750,570 B2 | 9/2017 | Condie et al. |
| 9,757,193 B2 | 9/2017 | Zarins et al. |
| 9,770,280 B2 | 9/2017 | Diederich et al. |
| 9,775,627 B2 | 10/2017 | Patel et al. |
| 9,782,221 B2 | 10/2017 | Srinivasan |
| 9,795,802 B2 | 10/2017 | Mohamed et al. |
| 9,814,514 B2 | 11/2017 | Shelton, IV et al. |
| 9,826,985 B2 | 11/2017 | Slobitker et al. |
| 9,844,406 B2 | 12/2017 | Edwards et al. |
| 9,848,890 B2 | 12/2017 | Yoon et al. |
| 9,848,944 B2 | 12/2017 | Sutton et al. |
| 9,872,687 B2 | 1/2018 | Tornier et al. |
| 9,872,691 B2 | 1/2018 | Griffiths et al. |
| 9,877,707 B2 | 1/2018 | Godara et al. |
| 9,901,392 B2 | 2/2018 | Phan et al. |
| 9,913,675 B2 | 3/2018 | Germain |
| 9,918,786 B2 | 3/2018 | Wang et al. |
| 9,980,771 B2 | 5/2018 | Carter et al. |
| 9,993,285 B2 | 6/2018 | Govari et al. |
| 10,022,140 B2 | 7/2018 | Germain et al. |
| 10,028,753 B2 | 7/2018 | Pellegrino et al. |
| 10,028,784 B2 | 7/2018 | Kramer et al. |
| 10,052,149 B2 | 8/2018 | Germain et al. |
| 10,052,152 B2 | 8/2018 | Tegg et al. |
| 10,052,153 B2 | 8/2018 | Olson |
| 10,058,336 B2 | 8/2018 | Truckai et al. |
| 10,105,175 B2 | 10/2018 | Godara et al. |
| 10,111,674 B2 | 10/2018 | Crainich et al. |
| 10,111,704 B2 | 10/2018 | Pellegrino et al. |
| 10,123,809 B2 | 11/2018 | Germain |
| 10,159,497 B2 | 12/2018 | Kuntz et al. |
| 10,245,092 B2 | 4/2019 | Germain |
| 10,265,099 B2 | 4/2019 | Pellegrino et al. |
| 10,272,271 B2 | 4/2019 | Diederich et al. |
| 10,292,716 B2 | 5/2019 | Aho et al. |
| 10,292,719 B2 | 5/2019 | Burger et al. |
| 10,299,805 B2 | 5/2019 | Germain et al. |
| 10,314,633 B2 | 6/2019 | Linderman et al. |
| 10,327,841 B2 | 6/2019 | Germain |
| 10,357,258 B2 | 7/2019 | Patel et al. |
| 10,357,307 B2 | 7/2019 | Harrison et al. |
| 10,376,271 B2 | 8/2019 | Mehta et al. |
| 10,383,641 B2 | 8/2019 | LeRoy et al. |
| 10,390,877 B2 * | 8/2019 | Heggeness .......... A61B 17/025 |
| 10,441,295 B2 | 10/2019 | Brockman et al. |
| 10,441,354 B2 | 10/2019 | Govari et al. |
| 10,448,995 B2 | 10/2019 | Olson |
| 10,456,187 B2 | 10/2019 | Edidin |
| 10,463,380 B2 | 11/2019 | Purdy et al. |
| 10,463,423 B2 | 11/2019 | Sutton et al. |
| 10,470,781 B2 | 11/2019 | Purdy et al. |
| 10,478,241 B2 | 11/2019 | Purdy et al. |
| 10,478,246 B2 | 11/2019 | Pellegrino et al. |
| 10,493,247 B2 | 12/2019 | Goshayeshgar |
| 10,499,960 B2 | 12/2019 | Sinnott et al. |
| 10,517,611 B2 | 12/2019 | Patel et al. |
| 10,524,805 B2 | 1/2020 | Zilberman et al. |
| 10,582,966 B2 | 3/2020 | Orczy-Timko et al. |
| 10,588,691 B2 | 3/2020 | Pellegino et al. |
| 10,589,131 B2 | 3/2020 | Diederich et al. |
| 10,603,522 B2 | 3/2020 | Diederich et al. |
| 10,624,652 B2 | 4/2020 | Germain et al. |
| 10,660,656 B2 | 5/2020 | Purdy et al. |
| 10,835,234 B2 | 11/2020 | Harari et al. |
| 10,849,613 B2 | 12/2020 | Rosner et al. |
| 10,864,040 B2 | 12/2020 | Dastjerdi et al. |
| 10,898,254 B2 | 1/2021 | Diederich et al. |
| 10,905,440 B2 | 2/2021 | Pellegrino et al. |
| 10,918,363 B2 | 2/2021 | Godara et al. |
| RE48,460 E | 3/2021 | Pellegrino et al. |
| 10,952,771 B2 | 3/2021 | Pellegrino |
| 11,007,010 B2 | 5/2021 | Donovan et al. |
| 11,026,734 B2 | 6/2021 | Truckai et al. |
| 11,026,744 B2 | 6/2021 | Purdy et al. |
| 11,052,267 B2 | 7/2021 | Diederich et al. |
| 11,065,046 B2 | 7/2021 | Edidin |
| 11,116,570 B2 | 9/2021 | Purdy et al. |
| 11,123,103 B2 | 9/2021 | Donovan et al. |
| 11,147,684 B2 | 10/2021 | Neubardt |
| 11,160,503 B2 | 11/2021 | Peesapati et al. |
| 11,160,563 B2 | 11/2021 | Patel et al. |
| 11,166,747 B2 | 11/2021 | Brockman et al. |
| 11,191,575 B2 | 12/2021 | Kidman et al. |
| 11,207,100 B2 | 12/2021 | Donovan et al. |
| 11,224,475 B2 | 1/2022 | Godara et al. |
| 11,234,764 B1 | 2/2022 | Patel et al. |
| 11,259,818 B2 | 3/2022 | Brockman et al. |
| 11,291,502 B2 | 4/2022 | Patel et al. |
| 11,344,350 B2 | 5/2022 | Purdy et al. |
| 11,364,069 B2 | 6/2022 | Heggeness |
| 11,376,021 B2 | 7/2022 | Marino et al. |
| 11,389,181 B2 | 7/2022 | Dutertre et al. |
| 11,419,614 B2 | 8/2022 | Weitzman et al. |

(56) References Cited

U.S. PATENT DOCUMENTS

| | | | |
|---|---|---|---|
| 11,426,199 B2 | 8/2022 | Donovan et al. | |
| 11,471,171 B2 | 10/2022 | Pellegrino et al. | |
| 11,471,210 B2 | 10/2022 | Pellegrino et al. | |
| 11,497,543 B2 | 11/2022 | Sprinkle et al. | |
| 11,510,723 B2 | 11/2022 | Defosset et al. | |
| 11,596,468 B2 | 3/2023 | Pellegrino et al. | |
| 11,690,667 B2 | 7/2023 | Pellegrino et al. | |
| 12,039,731 B2 * | 7/2024 | Donovan | G06T 7/0014 |
| 2001/0001314 A1 | 5/2001 | Davison et al. | |
| 2001/0001811 A1 | 5/2001 | Burney et al. | |
| 2001/0020167 A1 | 9/2001 | Woloszko et al. | |
| 2001/0023348 A1 | 9/2001 | Ashley et al. | |
| 2001/0025176 A1 | 9/2001 | Ellsberry et al. | |
| 2001/0025177 A1 | 9/2001 | Woloszko et al. | |
| 2001/0027295 A1 | 10/2001 | Dulak et al. | |
| 2001/0029370 A1 | 10/2001 | Hovda et al. | |
| 2001/0029373 A1 | 10/2001 | Baker et al. | |
| 2001/0029393 A1 | 10/2001 | Tierney et al. | |
| 2001/0032001 A1 | 10/2001 | Ricart et al. | |
| 2001/0047167 A1 | 11/2001 | Heggeness | |
| 2001/0049522 A1 | 12/2001 | Eggers et al. | |
| 2001/0049527 A1 | 12/2001 | Cragg | |
| 2001/0051802 A1 | 12/2001 | Woloszko et al. | |
| 2001/0053885 A1 | 12/2001 | Gielen et al. | |
| 2001/0056280 A1 | 12/2001 | Underwood et al. | |
| 2002/0016583 A1 | 2/2002 | Cragg | |
| 2002/0016600 A1 | 2/2002 | Cosman | |
| 2002/0019626 A1 | 2/2002 | Sharkey et al. | |
| 2002/0026186 A1 | 2/2002 | Woloszko et al. | |
| 2002/0049438 A1 | 4/2002 | Sharkey et al. | |
| 2002/0052600 A1 | 5/2002 | Davison et al. | |
| 2002/0068930 A1 | 6/2002 | Tasto et al. | |
| 2002/0095144 A1 | 7/2002 | Carl | |
| 2002/0095151 A1 | 7/2002 | Dahla et al. | |
| 2002/0095152 A1 | 7/2002 | Ciarrocca et al. | |
| 2002/0099366 A1 | 7/2002 | Dahla et al. | |
| 2002/0111661 A1 | 8/2002 | Cross et al. | |
| 2002/0115945 A1 | 8/2002 | D'Luzansky et al. | |
| 2002/0120259 A1 | 8/2002 | Lettice et al. | |
| 2002/0133148 A1 | 9/2002 | Daniel et al. | |
| 2002/0147444 A1 | 10/2002 | Shah et al. | |
| 2002/0151885 A1 | 10/2002 | Underwood et al. | |
| 2002/0165532 A1 | 11/2002 | Hill et al. | |
| 2002/0183758 A1 | 12/2002 | Middleton et al. | |
| 2002/0188284 A1 | 12/2002 | To et al. | |
| 2002/0188290 A1 | 12/2002 | Sharkey et al. | |
| 2002/0193708 A1 | 12/2002 | Thompson et al. | |
| 2002/0193789 A1 | 12/2002 | Underwood et al. | |
| 2003/0009164 A1 | 1/2003 | Woloszko et al. | |
| 2003/0014047 A1 | 1/2003 | Woloszko et al. | |
| 2003/0014088 A1 | 1/2003 | Fang et al. | |
| 2003/0028147 A1 | 2/2003 | Aves et al. | |
| 2003/0028189 A1 | 2/2003 | Woloszko et al. | |
| 2003/0040710 A1 | 2/2003 | Polidoro | |
| 2003/0040742 A1 | 2/2003 | Underwood et al. | |
| 2003/0040743 A1 | 2/2003 | Cosman et al. | |
| 2003/0055418 A1 | 3/2003 | Tasto et al. | |
| 2003/0069569 A1 | 4/2003 | Burdette et al. | |
| 2003/0083592 A1 | 5/2003 | Faciszewski | |
| 2003/0084907 A1 | 5/2003 | Pacek et al. | |
| 2003/0097126 A1 | 5/2003 | Woloszko et al. | |
| 2003/0097129 A1 | 5/2003 | Davison et al. | |
| 2003/0130655 A1 | 7/2003 | Woloszko et al. | |
| 2003/0139652 A1 | 7/2003 | Kang et al. | |
| 2003/0158545 A1 | 8/2003 | Hovda et al. | |
| 2003/0181963 A1 | 9/2003 | Pellegrino et al. | |
| 2003/0208194 A1 | 11/2003 | Hovda et al. | |
| 2003/0216725 A1 | 11/2003 | Woloszko et al. | |
| 2003/0216726 A1 | 11/2003 | Eggers et al. | |
| 2003/0225364 A1 | 12/2003 | Kraft | |
| 2004/0006339 A1 | 1/2004 | Underwood et al. | |
| 2004/0015163 A1 | 1/2004 | Buysse et al. | |
| 2004/0024399 A1 | 2/2004 | Sharps et al. | |
| 2004/0054366 A1 | 3/2004 | Davison et al. | |
| 2004/0064023 A1 | 4/2004 | Thomas et al. | |
| 2004/0064136 A1 | 4/2004 | Crombie et al. | |
| 2004/0064137 A1 | 4/2004 | Pellegrino et al. | |
| 2004/0068242 A1 | 4/2004 | McGuckin, Jr. | |
| 2004/0082942 A1 | 4/2004 | Katzman | |
| 2004/0082946 A1 | 4/2004 | Malis et al. | |
| 2004/0087937 A1 | 5/2004 | Eggers et al. | |
| 2004/0111087 A1 | 6/2004 | Stern et al. | |
| 2004/0116922 A1 | 6/2004 | Hovda et al. | |
| 2004/0120668 A1 | 6/2004 | Loeb | |
| 2004/0120891 A1 | 6/2004 | Hill et al. | |
| 2004/0133124 A1 | 7/2004 | Bates et al. | |
| 2004/0162559 A1 | 8/2004 | Arramon | |
| 2004/0186544 A1 | 9/2004 | King | |
| 2004/0193151 A1 | 9/2004 | To et al. | |
| 2004/0193152 A1 | 9/2004 | Sutton | |
| 2004/0220577 A1 | 11/2004 | Cragg et al. | |
| 2004/0225228 A1 | 11/2004 | Ferree | |
| 2004/0230190 A1 | 11/2004 | Dahla et al. | |
| 2004/0267269 A1 | 12/2004 | Middleton et al. | |
| 2005/0004634 A1 | 1/2005 | Ricart et al. | |
| 2005/0010095 A1 | 1/2005 | Stewart et al. | |
| 2005/0010203 A1 | 1/2005 | Edwards et al. | |
| 2005/0010205 A1 | 1/2005 | Hovda et al. | |
| 2005/0043737 A1 | 2/2005 | Reiley et al. | |
| 2005/0055096 A1 | 3/2005 | Serhan et al. | |
| 2005/0124989 A1 | 6/2005 | Suddaby | |
| 2005/0177209 A1 | 8/2005 | Leung et al. | |
| 2005/0177210 A1 | 8/2005 | Leung et al. | |
| 2005/0177211 A1 | 8/2005 | Leung et al. | |
| 2005/0182417 A1 | 8/2005 | Pagano | |
| 2005/0192564 A1 | 9/2005 | Cosman et al. | |
| 2005/0209610 A1 | 9/2005 | Carrison | |
| 2005/0209659 A1 | 9/2005 | Pellegrino et al. | |
| 2005/0216018 A1 | 9/2005 | Sennett | |
| 2005/0234445 A1 | 10/2005 | Conquergood et al. | |
| 2005/0261754 A1 | 11/2005 | Woloszko | |
| 2005/0267552 A1 | 12/2005 | Conquergood et al. | |
| 2005/0278007 A1 | 12/2005 | Godara | |
| 2005/0283148 A1 | 12/2005 | Janssen et al. | |
| 2006/0004369 A1 | 1/2006 | Patel et al. | |
| 2006/0036264 A1 | 2/2006 | Selover et al. | |
| 2006/0052743 A1 | 3/2006 | Reynolds | |
| 2006/0064101 A1 | 3/2006 | Arramon | |
| 2006/0095026 A1 | 5/2006 | Ricart et al. | |
| 2006/0095028 A1 | 5/2006 | Bleich | |
| 2006/0106375 A1 | 5/2006 | Werneth et al. | |
| 2006/0106376 A1 | 5/2006 | Godara et al. | |
| 2006/0122458 A1 | 6/2006 | Bleich | |
| 2006/0129101 A1 | 6/2006 | McGuckin | |
| 2006/0178670 A1 | 8/2006 | Woloszko et al. | |
| 2006/0200121 A1 | 9/2006 | Mowery | |
| 2006/0206128 A1 | 9/2006 | Conquergood et al. | |
| 2006/0206129 A1 | 9/2006 | Conquergood et al. | |
| 2006/0206130 A1 | 9/2006 | Conquergood et al. | |
| 2006/0206132 A1 | 9/2006 | Conquergood et al. | |
| 2006/0206133 A1 | 9/2006 | Conquergood et al. | |
| 2006/0206134 A1 | 9/2006 | Conquergood et al. | |
| 2006/0206166 A1 | 9/2006 | Weiner | |
| 2006/0217736 A1 | 9/2006 | Kaneko et al. | |
| 2006/0229625 A1 | 10/2006 | Truckai et al. | |
| 2006/0247746 A1 | 11/2006 | Danek et al. | |
| 2006/0253117 A1 | 11/2006 | Hovda et al. | |
| 2006/0259026 A1 | 11/2006 | Godara et al. | |
| 2006/0264957 A1 | 11/2006 | Cragg et al. | |
| 2006/0264965 A1 | 11/2006 | Shadduck et al. | |
| 2006/0265014 A1 | 11/2006 | Demarais et al. | |
| 2006/0276749 A1 | 12/2006 | Selmon et al. | |
| 2006/0287649 A1 | 12/2006 | Ormsby et al. | |
| 2007/0021803 A1 | 1/2007 | Deem et al. | |
| 2007/0027449 A1 | 2/2007 | Godara et al. | |
| 2007/0055316 A1 | 3/2007 | Godara et al. | |
| 2007/0066987 A1 | 3/2007 | Scanlan et al. | |
| 2007/0074719 A1 | 4/2007 | Danek et al. | |
| 2007/0118142 A1 | 5/2007 | Krueger et al. | |
| 2007/0129715 A1 | 6/2007 | Eggers et al. | |
| 2007/0142791 A1 | 6/2007 | Yeung et al. | |
| 2007/0142842 A1 | 6/2007 | Krueger et al. | |
| 2007/0149966 A1 | 6/2007 | Dahla et al. | |
| 2007/0179497 A1 | 8/2007 | Eggers et al. | |

(56) References Cited

U.S. PATENT DOCUMENTS

| | | |
|---|---|---|
| 2007/0185231 A1 | 8/2007 | Liu et al. |
| 2007/0213584 A1 | 9/2007 | Kim et al. |
| 2007/0213735 A1 | 9/2007 | Saadat et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0065062 A1 | 3/2008 | Leung et al. |
| 2008/0091207 A1 | 4/2008 | Truckai et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2008/0294167 A1 | 11/2008 | Schumacher et al. |
| 2009/0030308 A1 | 1/2009 | Bradford et al. |
| 2009/0054951 A1 | 2/2009 | Leuthardt et al. |
| 2009/0069807 A1 | 3/2009 | Eggers et al. |
| 2009/0076520 A1 | 3/2009 | Choi |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149846 A1 | 6/2009 | Hoey et al. |
| 2009/0149878 A1 | 6/2009 | Truckai et al. |
| 2009/0204192 A1 | 8/2009 | Carlton et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0179556 A1 | 7/2010 | Scribner et al. |
| 2010/0185082 A1 | 7/2010 | Chandran et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0286487 A1 | 11/2010 | Van Lue |
| 2010/0298737 A1 | 11/2010 | Koehler |
| 2010/0298822 A1 | 11/2010 | Behnke |
| 2010/0298832 A1 | 11/2010 | Lau et al. |
| 2010/0305559 A1 | 12/2010 | Brannan et al. |
| 2010/0324506 A1 | 12/2010 | Pellegrino et al. |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0130751 A1 | 6/2011 | Malis et al. |
| 2011/0144524 A1 | 6/2011 | Fish et al. |
| 2011/0152855 A1 | 6/2011 | Mayse et al. |
| 2011/0196361 A1 | 8/2011 | Vilims |
| 2011/0206260 A1 | 8/2011 | Bergmans et al. |
| 2011/0264098 A1 | 10/2011 | Cobbs |
| 2011/0270238 A1 | 11/2011 | Rizq et al. |
| 2011/0276001 A1 | 11/2011 | Schultz et al. |
| 2011/0295245 A1 | 12/2011 | Willyard et al. |
| 2011/0295261 A1 | 12/2011 | Germain |
| 2011/0319765 A1 | 12/2011 | Gertner et al. |
| 2012/0029420 A1 | 2/2012 | Rittman et al. |
| 2012/0116266 A1 | 5/2012 | House et al. |
| 2012/0136346 A1 | 5/2012 | Condie et al. |
| 2012/0136348 A1 | 5/2012 | Condie et al. |
| 2012/0143090 A1 | 6/2012 | Hay et al. |
| 2012/0143341 A1 | 6/2012 | Zipnick |
| 2012/0172858 A1 | 7/2012 | Harrison et al. |
| 2012/0172859 A1 | 7/2012 | Condie et al. |
| 2012/0191095 A1 | 7/2012 | Burger et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226145 A1 | 9/2012 | Chang et al. |
| 2012/0226273 A1 | 9/2012 | Nguyen et al. |
| 2012/0239049 A1 | 9/2012 | Truckai et al. |
| 2012/0239050 A1 | 9/2012 | Linderman |
| 2012/0265186 A1 | 10/2012 | Burger et al. |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0060244 A1 | 3/2013 | Godara et al. |
| 2013/0079810 A1 | 3/2013 | Isenberg |
| 2013/0103022 A1 | 4/2013 | Sutton et al. |
| 2013/0197508 A1 | 8/2013 | Shikhman et al. |
| 2013/0231654 A1 | 9/2013 | Germain |
| 2013/0237979 A1 | 9/2013 | Shikhman et al. |
| 2013/0261507 A1 | 10/2013 | Diederich et al. |
| 2013/0274784 A1 | 10/2013 | Lenker et al. |
| 2013/0296767 A1 | 11/2013 | Zarins et al. |
| 2013/0324993 A1 | 12/2013 | McCarthy et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0331840 A1 | 12/2013 | Teisen et al. |
| 2013/0345765 A1 | 12/2013 | Brockman et al. |
| 2014/0031715 A1 | 1/2014 | Sherar et al. |
| 2014/0039500 A1 | 2/2014 | Pellegrino et al. |
| 2014/0046245 A1 | 2/2014 | Cornacchia |
| 2014/0046328 A1 | 2/2014 | Schumacher et al. |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0194887 A1 | 7/2014 | Shenoy |
| 2014/0221967 A1 | 8/2014 | Childs et al. |
| 2014/0236137 A1 | 8/2014 | Tran et al. |
| 2014/0236144 A1 | 8/2014 | Krueger et al. |
| 2014/0243823 A1 | 8/2014 | Godara et al. |
| 2014/0243943 A1 | 8/2014 | Rao et al. |
| 2014/0257265 A1 | 9/2014 | Godara et al. |
| 2014/0257296 A1 | 9/2014 | Morgenstern Lopez |
| 2014/0271717 A1 | 9/2014 | Goshayeshgar et al. |
| 2014/0275760 A1 | 9/2014 | Lee et al. |
| 2014/0276713 A1 | 9/2014 | Lee et al. |
| 2014/0276728 A1 | 9/2014 | Goshayeshgar et al. |
| 2014/0276744 A1 | 9/2014 | Arthur et al. |
| 2014/0288544 A1 | 9/2014 | Diederich et al. |
| 2014/0288546 A1 | 9/2014 | Sherman et al. |
| 2014/0296850 A1 | 10/2014 | Condie et al. |
| 2014/0303610 A1 | 10/2014 | McCarthy et al. |
| 2014/0303614 A1 | 10/2014 | McCarthy et al. |
| 2014/0316405 A1 | 10/2014 | Pellegrino et al. |
| 2014/0316413 A1 | 10/2014 | Burger et al. |
| 2014/0324051 A1 | 10/2014 | Pellegrino et al. |
| 2014/0330332 A1 | 11/2014 | Danek et al. |
| 2014/0336630 A1 | 11/2014 | Woloszko et al. |
| 2014/0336667 A1 | 11/2014 | Pellegrino et al. |
| 2014/0364842 A1 | 12/2014 | Werneth et al. |
| 2014/0371740 A1 | 12/2014 | Germain et al. |
| 2015/0005614 A1 | 1/2015 | Heggeness et al. |
| 2015/0005767 A1 | 1/2015 | Werneth et al. |
| 2015/0045783 A1 | 2/2015 | Edidin |
| 2015/0057658 A1 | 2/2015 | Sutton et al. |
| 2015/0065945 A1 | 3/2015 | Zarins et al. |

(56) References Cited

U.S. PATENT DOCUMENTS

| | | |
|---|---|---|
| 2015/0073515 A1 | 3/2015 | Turovskiy et al. |
| 2015/0105701 A1 | 4/2015 | Mayer et al. |
| 2015/0141876 A1 | 5/2015 | Diederich et al. |
| 2015/0157402 A1 | 6/2015 | Kunis et al. |
| 2015/0164546 A1 | 6/2015 | Pellegrino et al. |
| 2015/0196358 A1 | 7/2015 | Gosbayesbgar |
| 2015/0216588 A1 | 8/2015 | Deem et al. |
| 2015/0231417 A1 | 8/2015 | Metcalf et al. |
| 2015/0272655 A1 | 10/2015 | Condie et al. |
| 2015/0273208 A1 | 10/2015 | Hamilton |
| 2015/0297246 A1 | 10/2015 | Patel et al. |
| 2015/0297282 A1 | 10/2015 | Cadouri |
| 2015/0320480 A1 | 11/2015 | Cosman, Jr. et al. |
| 2015/0335349 A1 | 11/2015 | Pellegrino et al. |
| 2015/0335382 A1 | 11/2015 | Pellegrino et al. |
| 2015/0342619 A1 | 12/2015 | Weitzman |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0045207 A1 | 2/2016 | Kovacs et al. |
| 2016/0045256 A1 | 2/2016 | Godara et al. |
| 2016/0051831 A1 | 2/2016 | Lundmark et al. |
| 2016/0059007 A1 | 3/2016 | Koop |
| 2016/0073948 A1* | 3/2016 | Videman ................ A61B 5/004 |
| | | 600/410 |
| 2016/0074068 A1 | 3/2016 | Patwardhan |
| 2016/0074133 A1 | 3/2016 | Shikhman et al. |
| 2016/0074279 A1 | 3/2016 | Shin |
| 2016/0074661 A1 | 3/2016 | Lipani |
| 2016/0081716 A1 | 3/2016 | Boling et al. |
| 2016/0081810 A1 | 3/2016 | Reiley et al. |
| 2016/0095721 A1 | 4/2016 | Schell et al. |
| 2016/0106443 A1 | 4/2016 | Kuntz et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166302 A1 | 6/2016 | Tan-Malecki et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0199117 A1 | 7/2016 | Druma |
| 2016/0213927 A1 | 7/2016 | McGee et al. |
| 2016/0220317 A1 | 8/2016 | Shikhman et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0262904 A1 | 9/2016 | Schaller et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0278861 A1 | 9/2016 | Ko |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0296739 A1 | 10/2016 | Cleveland |
| 2016/0302925 A1 | 10/2016 | Keogh et al. |
| 2016/0302936 A1 | 10/2016 | Billon et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 12/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375259 A1 | 12/2016 | Davis et al. |
| 2017/0000501 A1 | 1/2017 | Aho et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049500 A1 | 2/2017 | Shikhman et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0056028 A1 | 3/2017 | Germain et al. |
| 2017/0065329 A1 | 3/2017 | Benamou et al. |
| 2017/0112507 A1 | 4/2017 | Crainich et al. |
| 2017/0119461 A1 | 5/2017 | Godara et al. |
| 2017/0128080 A1 | 5/2017 | Torrie |
| 2017/0128112 A1 | 5/2017 | Germain |
| 2017/0135742 A1 | 5/2017 | Lee et al. |
| 2017/0164998 A1 | 6/2017 | Klimovitch |
| 2017/0172650 A1 | 6/2017 | Germain |
| 2017/0181788 A1 | 6/2017 | Dastjerdi et al. |
| 2017/0202613 A1 | 7/2017 | Pellegrino et al. |
| 2017/0238943 A1 | 8/2017 | Sennett et al. |
| 2017/0246481 A1 | 8/2017 | Mischelevich |
| 2017/0266419 A1 | 9/2017 | Gosbayesbgar |
| 2017/0303983 A1 | 10/2017 | Linderman et al. |
| 2017/0312007 A1 | 11/2017 | Harlev et al. |
| 2017/0333052 A1 | 11/2017 | Ding et al. |
| 2018/0021048 A1 | 1/2018 | Pellegrino et al. |
| 2018/0042656 A1 | 2/2018 | Edidin |
| 2018/0055539 A1 | 3/2018 | Pellegino |
| 2018/0103964 A1 | 4/2018 | Patel et al. |
| 2018/0140245 A1 | 5/2018 | Videman |
| 2018/0153604 A1 | 6/2018 | Ayvazyan et al. |
| 2018/0161047 A1 | 6/2018 | Purdy et al. |
| 2018/0193088 A1 | 7/2018 | Sutton et al. |
| 2018/0303509 A1 | 10/2018 | Germain et al. |
| 2019/0029698 A1 | 1/2019 | Pellegrino et al. |
| 2019/0038296 A1 | 2/2019 | Pellegrino |
| 2019/0038343 A1 | 2/2019 | Sutton et al. |
| 2019/0038344 A1 | 2/2019 | Pellegrino |
| 2019/0038345 A1 | 2/2019 | Pellegrino |
| 2019/0090933 A1 | 3/2019 | Pellegrino et al. |

(56) References Cited

U.S. PATENT DOCUMENTS

| | | | |
|---|---|---|---|
| 2019/0110833 A1 | 4/2019 | Pellegrino et al. | |
| 2019/0118003 A1 | 4/2019 | Diederich et al. | |
| 2019/0118004 A1 | 4/2019 | Diederich et al. | |
| 2019/0118005 A1 | 4/2019 | Diederich et al. | |
| 2019/0175252 A1 | 6/2019 | Heggeness | |
| 2019/0216486 A1 | 7/2019 | Weitzman | |
| 2019/0282268 A1 | 9/2019 | Pellegrino et al. | |
| 2019/0290296 A1 | 9/2019 | Patel et al. | |
| 2019/0298392 A1 | 10/2019 | Capote et al. | |
| 2019/0365416 A1 | 12/2019 | Brockman et al. | |
| 2020/0000480 A1 | 1/2020 | Alambeigi et al. | |
| 2020/0022709 A1 | 1/2020 | Burger et al. | |
| 2020/0022749 A1 | 1/2020 | Malkevich et al. | |
| 2020/0030601 A1 | 1/2020 | Molnar et al. | |
| 2020/0060695 A1 | 2/2020 | Purdy et al. | |
| 2020/0060747 A1 | 2/2020 | Edidin | |
| 2020/0069920 A1 | 3/2020 | Goshayeshgar | |
| 2020/0078083 A1 | 3/2020 | Sprinkle et al. | |
| 2020/0138454 A1 | 5/2020 | Patel et al. | |
| 2020/0146743 A1 | 5/2020 | Defosset et al. | |
| 2020/0146744 A1 | 5/2020 | Defosset et al. | |
| 2020/0179033 A1 | 6/2020 | Banamou et al. | |
| 2020/0214762 A1 | 7/2020 | Pellegrino et al. | |
| 2020/0281646 A1 | 9/2020 | Pellegrino et al. | |
| 2020/0390493 A1 | 12/2020 | Orczy-Timko et al. | |
| 2020/0405499 A1 | 12/2020 | Gerbec et al. | |
| 2021/0022814 A1 | 1/2021 | Crawford et al. | |
| 2021/0077170 A1 | 3/2021 | Wiersdorf et al. | |
| 2021/0093373 A1 | 4/2021 | Dastjerdi et al. | |
| 2021/0113238 A1 | 4/2021 | Donovan et al. | |
| 2021/0145416 A1 | 5/2021 | Godara et al. | |
| 2021/0177502 A1 | 6/2021 | Wright et al. | |
| 2021/0290254 A1 | 9/2021 | Serrahima Tornel et al. | |
| 2021/0361350 A1 | 11/2021 | Pellegrino et al. | |
| 2021/0361351 A1 | 11/2021 | Pellegrino et al. | |
| 2021/0369323 A1 | 12/2021 | Edidin | |
| 2021/0386491 A1 | 12/2021 | Shmayahu et al. | |
| 2021/0401496 A1 | 12/2021 | Purdy et al. | |
| 2022/0022930 A1 | 1/2022 | Brockman et al. | |
| 2022/0031390 A1 | 2/2022 | Ebersole et al. | |
| 2022/0096143 A1 | 3/2022 | Godara et al. | |
| 2022/0110639 A1 | 4/2022 | Brockman et al. | |
| 2022/0125386 A1* | 4/2022 | Marras | A61B 5/1114 |
| 2022/0192702 A1 | 6/2022 | Donovan et al. | |
| 2022/0192722 A1 | 6/2022 | Harshman et al. | |
| 2022/0202471 A1 | 6/2022 | Schepis et al. | |
| 2022/0218411 A1 | 7/2022 | Druma et al. | |
| 2022/0218434 A1 | 7/2022 | Druma | |
| 2022/0240916 A1 | 8/2022 | Jung et al. | |
| 2022/0296255 A1 | 9/2022 | Patel et al. | |
| 2022/0401114 A1 | 12/2022 | Marino et al. | |
| 2023/0046328 A1 | 2/2023 | Weitzman et al. | |
| 2023/0138303 A1 | 5/2023 | Pellegrino et al. | |
| 2023/0172656 A1 | 6/2023 | Druma | |
| 2023/0255676 A1 | 8/2023 | Donovan et al. | |

FOREIGN PATENT DOCUMENTS

| | | |
|---|---|---|
| EP | 0584959 | 3/1994 |
| EP | 0597463 | 5/1994 |
| EP | 0880938 | 12/1998 |
| EP | 1013228 | 6/2000 |
| EP | 1059067 | 12/2000 |
| EP | 1059087 | 12/2000 |
| EP | 1402821 A2 | 3/2004 |
| EP | 1402838 A1 | 3/2004 |
| EP | 1652486 A1 | 5/2006 |
| EP | 1641406 B1 | 3/2007 |
| EP | 1294323 B1 | 4/2007 |
| EP | 1832244 A2 | 9/2007 |
| EP | 1938765 A1 | 7/2008 |
| EP | 1471836 B1 | 4/2010 |
| EP | 2438876 A1 | 4/2012 |
| EP | 1968472 B1 | 2/2013 |
| EP | 1824424 B1 | 1/2014 |
| EP | 2785260 | 8/2015 |
| EP | 2965782 | 1/2016 |
| EP | 2508225 | 9/2016 |
| EP | 3078395 | 10/2016 |
| EP | 2205313 B1 | 11/2016 |
| EP | 3097946 | 11/2016 |
| EP | 2913081 | 1/2017 |
| EP | 2642931 B1 | 3/2017 |
| EP | 3187132 A1 | 7/2017 |
| EP | 2590579 B1 | 8/2019 |
| EP | 3057517 B1 | 4/2020 |
| EP | 2978373 B1 | 7/2021 |
| EP | 3410961 B1 | 11/2022 |
| JP | 53-139791 | 11/1978 |
| JP | 6-47058 | 2/1994 |
| JP | 10-290806 | 11/1998 |
| JP | 2001-037760 | 2/2001 |
| JP | 2005-169012 | 6/2005 |
| WO | WO96/36289 | 11/1996 |
| WO | WO98/27876 | 7/1998 |
| WO | WO98/34550 | 8/1998 |
| WO | WO99/19025 | 4/1999 |
| WO | WO99/44519 | 9/1999 |
| WO | WO99/48621 | 9/1999 |
| WO | WO00/21448 | 4/2000 |
| WO | WO00/33909 | 6/2000 |
| WO | WO00/49978 | 8/2000 |
| WO | WO00/56237 | 9/2000 |
| WO | WO00/67648 | 11/2000 |
| WO | WO00/67656 | 11/2000 |
| WO | WO01/01877 | 1/2001 |
| WO | WO01/45579 | 6/2001 |
| WO | WO01/57655 | 8/2001 |
| WO | WO 2002/05699 | 1/2002 |
| WO | WO 2002/05897 | 1/2002 |
| WO | WO 2002/026319 | 4/2002 |
| WO | WO 2002/28302 | 4/2002 |
| WO | WO 2002/054941 | 7/2002 |
| WO | WO 2002/067797 | 9/2002 |
| WO | WO 2002/096304 | 12/2002 |
| WO | WO 2006/044794 | 4/2006 |
| WO | WO 2007/001981 | 1/2007 |
| WO | WO2007/008954 | 1/2007 |
| WO | WO 2007/031264 | 3/2007 |
| WO | WO 2008/001385 | 1/2008 |
| WO | WO 2008/008522 | 1/2008 |
| WO | WO 2008/076330 | 6/2008 |
| WO | WO 2008/076357 | 6/2008 |
| WO | WO 2008/121259 | 10/2008 |
| WO | WO 2008/140519 | 11/2008 |
| WO | WO 2008/141104 | 11/2008 |
| WO | WO2008/144709 | 11/2008 |
| WO | WO 2009/042172 | 4/2009 |
| WO | WO 2009/076461 | 6/2009 |
| WO | WO 2009/124192 | 10/2009 |
| WO | WO 2009/155319 | 12/2009 |
| WO | WO 2010/036865 | 4/2010 |
| WO | WO 2010/111246 | 9/2010 |
| WO | WO 2010/135606 | 11/2010 |
| WO | WO 2011/041038 | 4/2011 |
| WO | WO 2012/024162 | 2/2012 |
| WO | WO 2012/065753 | 3/2012 |
| WO | WO 2012/074932 | 6/2012 |
| WO | WO 2013/009516 | 1/2013 |
| WO | WO 2013/134452 | 9/2013 |
| WO | WO 2013/168006 | 11/2013 |
| WO | WO 2013/180947 | 12/2013 |
| WO | WO 2014/004051 | 1/2014 |
| WO | WO 2014/130231 | 8/2014 |
| WO | WO 2014/141207 | 9/2014 |
| WO | WO 2014/165194 | 10/2014 |
| WO | WO 2014/176141 | 10/2014 |
| WO | WO 2015/038317 | 3/2015 |
| WO | WO 2015/047817 | 4/2015 |
| WO | WO 2015/066295 | 5/2015 |
| WO | WO 2015/066303 | 5/2015 |
| WO | WO 2015/079319 | 6/2015 |
| WO | WO 2015/148105 | 10/2015 |
| WO | WO 2014/145222 | 1/2016 |

(56) References Cited

FOREIGN PATENT DOCUMENTS

| WO | WO 2014/145659 | | 1/2016 |
|----|----|----|----|
| WO | WO 2014/146029 | | 1/2016 |
| WO | WO 2016/033380 | | 3/2016 |
| WO | WO 2016/048965 | | 3/2016 |
| WO | WO 2014/197596 | | 4/2016 |
| WO | WO 2014/210373 | | 5/2016 |
| WO | WO 2016/069157 | | 5/2016 |
| WO | WO 2016/075544 | | 5/2016 |
| WO | WO 2015/024013 | | 6/2016 |
| WO | WO 2016/090420 | | 6/2016 |
| WO | WO 2016/105448 | | 6/2016 |
| WO | WO 2016/105449 | | 6/2016 |
| WO | WO 2015/044945 | | 8/2016 |
| WO | WO 2015/057696 | | 8/2016 |
| WO | WO 2015/060927 | | 8/2016 |
| WO | WO 2016/127130 | | 8/2016 |
| WO | WO 2016/130686 | | 8/2016 |
| WO | WO 2016/134273 | | 8/2016 |
| WO | WO 2011/157714 | | 9/2016 |
| WO | WO 2016/148954 | | 9/2016 |
| WO | WO 2016/154091 | | 9/2016 |
| WO | WO 2016/168381 | | 10/2016 |
| WO | WO 2016/209682 | | 12/2016 |
| WO | WO 2017/009472 | | 1/2017 |
| WO | WO2017/010930 | | 1/2017 |
| WO | WO 2017/019863 | | 2/2017 |
| WO | WO 2017/027703 | | 2/2017 |
| WO | WO 2017/027809 | | 2/2017 |
| WO | WO 2018/116273 | | 6/2018 |
| WO | WO 2020/198150 | | 10/2020 |
| WO | WO 2021/016699 | A1 | 2/2021 |
| WO | WO 2022/066743 | A2 | 3/2022 |
| WO | WO 2022/125875 | A1 | 6/2022 |
| WO | WO 2022/191978 | A1 | 9/2022 |
| WO | WO 2022/207105 | A1 | 10/2022 |
| WO | WO 2023/009697 | A1 | 2/2023 |

OTHER PUBLICATIONS

Antonacci M. Darryl et al.; Innervation of the Human Vertebral Body: A Histologic Study; Journal of Spinal Disorder vol. 11 No. 6 pp. 526-531 1998 Lippincott Williams & Wilkins Philadelphia.

Arnoldi Carl C.; Intraosseous Hypertension—A Possible Cause of Low Back Pain?; Clinical Orthopedics and Related Research No. 115 Mar.-Apr. 1976.

Bailey, Jeannie F., "Innervation Patterns of PGP 9.5-Positive Nerve Fibers within the Human Lumbar Vertebra," Journal of Anatomy, (2011) 218, pp. 263-270, San Francisco, California.

Becker, Stephan, et al., "Ablation of the basivertebral nerve for treatment of back pain: a clinical study," The Spine Journal, vol. 17, pp. 218-223 (Feb. 2017).

Bergeron et al. "Fluoroscopic-guided radiofrequency ablation of the basivertebral nerve: application and analysis with multiple imaging modalities in an ovine model" Thermal Treatment of Tissue: Energy Delivery and Assessment III edited by Thomas P. Ryan Proceedings of SPIE vol. 5698 (SPIE Bellingham WA 2005) pp. 156-167.

Bogduk N. The anatomy of the lumbar intervertebral disc syndrome Med J. Aust. 1976 vol. 1 No. 23 pp. 878-881.

Bogduk Nikolai et al.; Technical Limitations to the efficacy of Radiofrequency Neurotomy for Spinal Pain; Neurosurgery vol. 20 No. 4 1987.

Caragee, EG et al.; "Discographic, MRI and psychosocial determinants of low back pain disability andremission: A prospective study in subjects with benign persistent back pain", The Spine Journal: The Official Journal of the North American Spine Society, vol. 5(1), pp. 24-35 (2005).

Choy Daniel SS.J. et al.; Percutaneous Laser Disc Decompression A New Therapeutic Modality; Spine vol. 17 No. 8 1992.

Cosman E.R. et al. Theoretical Aspects of Radiofrequency Lesions in the Dorsal Root Entry Zone. Neurosurgery vol. 1 No. 6 1984 pp. 945-950.

Deardorff Dana L. et al.; Ultrasound applicators with internal cooling for interstitial thermal therapy; SPIE vol. 3594 1999.

Deramond H. et al. Temperature Elevation Caused by Bone Cement Polymerization During Vertebroplasty Bone Aug. 1999 pp. 178-21S vol. 25 No. 2 Supplement.

Diederich C. J. et al. "IDTT Therapy in Cadaveric Lumbar Spine: Temperature and thermal dosedistributions Thermal Treatment of Tissue: Energy Delivery and Assessment" Thomas P. Ryan Editor Proceedings of SPIE vol. 4247:104-108 (2001).

Diederich Chris J. et al.; Ultrasound Catheters for Circumferential Cardiac Ablation; SPIE vol. 3594 (1999).

Dupuy D.E. et al. Radiofrequency ablation of spinal tumors: Temperature distribution in the spinal canal AJR vol. 175 pp. 1263-1266 Nov. 2000.

Dupuy Damian E.; Radiofrequency Ablation: An Outpatient Percutaneous Treatment; Medicine and Health/Rhode Island vol. 82 No. Jun. 6, 1999.

Esses Stephen I. et al.; Intraosseous Vertebral Body Pressures; Spine vol. 17 No. 6 Supplement 1992.

FDA Response to 510(k) Submission by Relievant Medsystems Inc. submitted on Sep. 27, 2007 (date stamped on Oct. 5, 2007) and associated documents.

Fields, AJ et al; "Innervation of pathologies in the lumbar vertebral endplate and intervertebral disc",The Spine Journal: Official Journal of the North American Spine Society, vol. 14(3), pp. 513-521 (2014).

Fields, Aaron J. et al.; "Cartilage endplate damage strongly assocates with chronic low back pain, independent of modic changes", Abstract form Oral Presentation at the ISSLS Annual Meeting in Banff, Canada (May 14-18, 2018).

Fischgrund JS, et al.; "Intraosseous Basivertebral Nerve Ablation for the Treatment of Chronic Low Back Pain: 2-Year Results from a Prospective Randomized Double-Blind Sham-Controlled Multicenter Study", International Journal of Spine Surgery, vol. 13 (2), pp. 110-119 (2019).

Fras M.D., Christian et al., "Substance P-containing Nerves within the Human Vertebral Body: An Immunohistochemical Study of the Basivertebral Nerve", The Spine Journal 3, 2003, pp. 63-67.

Gehl J. "Electroporation: theory and methods perspectives for drug delivery gene therapy and research" Acta Physiol. Scand. vol. 177 pp. 437-447 (2003).

Goldberg S.N. et al. Tissue ablation with radiofrequency: Effect of probe size gauge duration and temperature on lesion volume Acad. Radiol. vol. 2 pp. 399-404 (1995).

Gornet, Matthew G et al.; "Magnetic resonance spectroscopy (MRS) can identify painful lumbar discsand may facilitate improved clinical outcomes of lumbar surgeries for discogenic pain", European Spine Journal, vol. 28, pp. 674-687 (2019).

Hanai Kenji et al.; Simultaneous Measurement of Intraosseous and Cerebrospinal Fluid Pressures in the Lumbar Region; Spine vol. 10 No. 1 1985.

Heggeness Michael H. et al. The Trabecular Anatomy of Thoracolumbar Vertebrae: Implications for Burst Fractures Journal of Anatomy 1997 pp. 309-312 vol. 191 Great Britain.

Heggeness Michael H. et al. Discography Causes End Plate Deflection; Spine vol. 18 No. 8 pp. 1050-1053 1993 J.B. Lippincott Company.

Heggeness, M. et al.Ablation of the Basivertebral Nerve for the Treatment of Back Pain: A Pilot Clinical Study; The Spine Journal, 2011, vol. 11, Issue 10, Supplement, pp. S65-S66, ISSN 1529-9430.

Hoopes et al. "Radiofrequency Ablation of The Basivertebral Nerve as a Potential Treatment of Back Pain: Pathologic Assessment in an Ovine Model" Thermal Treatment of Tissue: Energy Delivery and Assessment III edited by Thomas P. Ryan Proceedings of SPIE vol. 5698 (SPIE Bellingham WA 2005) pp. 168-180.

Houpt Jonathan C. et al.; Experimental Study of Temperature Distributions and Thermal TransportDuring Radiofrequency Current Therapy of the Intervertebral Disc; Spine vol. 21 No. 15 pp. 1808-1813 1996 Lippincott-Raven Publishers.

Jourabchi, Natanel et al.; "Irreversible electroporation (NanoKnife) in cancer treatment," Gastrointestinal Intervention, vol. 3, pp. 8-18 (2014).

(56)                        References Cited

OTHER PUBLICATIONS

Khalil, J et al.; "A Prospective, Randomized, Multi-Center Study of Intraosseous Basivertebral Nerve Ablation for the Treatment of Chronic Low Back Pain", The Spine Journal (2019), avilable at https://doi.org/10.1016/jspinee.2019.05.598.

Kleinstueck Frank S. et al.; Acute Biomechanical and Histological Effects of Intradiscal Electrothermal Therapy on Human Lumbar Discs; Spine vol. 26 No. 20 pp. 2198-2207; 2001 Lippincott Williams & Wilkins Inc.

Kopecky Kenyon K. et al. "Side-Exiting Coaxial Needle for Aspiration Biopsy"—AJR—1996; 167 pp. 661-662.

Kuisma M et al.; "Modic changes in endplates of lumbar vertebral bodies: Prevalence and associationwith low back and sciatic pain among middle-aged male workers", Spine, vol. 32(10), pp. 1116-1122 (2007).

Lehmann Justus F. et al.; Selective Heating Effects of Ultrasound in Human Beings; Archives of Physical Medicine & Rehabilitation Jun. 1966.

Letcher Frank S. et al.; The Effect of Radiofrequency Current and Heat on Peripheral Nerve Action Potential in the Cat; U.S. Naval Hospital Philadelphia PA. (1968).

Lotz JC, et al.; "The Role of the Vertebral End Plate in Low Back Pain", Global Spine Journal, vol. 3, pp. 153-164 (2013).

Lundskog Jan; Heat and Bone Tissue-/an experimental investigation of the thermal properties of bone tissue and threshold levels for thermal injury; Scandinavian Journal of Plastic and Reconstructive Surgery Supplemental 9 From the Laboratory of Experimental Biology Department of anatomy University of Gothenburg Gothenburg Sweden Goteborg 1972.

Martin J.B. et al. Vertebroplasty: Clinical Experience and Follow-up Results Bone Aug. 1999 pp. 11S-15S vol. 25 No. 2 Supplement.

Massad Malek M.D. et al.; Endoscopic Thoracic Sympathectomy: Evaluation of Pulsatile Laser Non-Pulsatile Laser and Radiofrequency-Generated Thermocoagulation; Lasers in Surgery and Medicine; 1991; pp. 18-25.

Mehta Mark et al.; The treatment of chronic back pain; Anaesthesia 1979 vol. 34 pp. 768-775.

Modic MT et al.; "Degenerative disk disease: assessment of changes in vertebral body marrow with MR imaging" Radiology vol. 166 pp. 193-199 (1988).

Mok, Florence et al.; "Modic changes of the lumbar spine: Prevalence, risk factors, and associationwith disc degeneration and low back pain in a large-scale population-based cohort", The Spine Journal: Official Journal of the North American Spine Society, vol. 16(1), pp. 32-41 (2016).

Nau William H. Ultrasound interstitial thermal therapy (USITT) in the prostate; SPIE vol. 3594 Jan. 1999.

Osteocool Pain Management Brochure, Baylis Medical, copyright 2011.

Pang, Henry et al,; The UTE Disc Sign on MRI; A Novel Imaging Biomarker Associated With Degenerative Spine Changes, Low Back Pain, and Disability, Spine, vol. 42 (Aug. 2017).

Radiological Society of North America. "Pulsed radiofrequency relieves acute back pain and sciatica."ScienceDaily. ScienceDaily, Nov. 27, 2018. <www.sciencedaily.com/releases/2018/11/181127092604.htm>.

Rashbaum Ralph F.; Radiofrequency Facet Denervation A Treatment alternative in Refractory Low Back Pain with or without Leg Pain; Orthopedic Clinics of North America—vol. 14 No. Jul. 3, 1983.

Rosenthal D.I. Seminars in Musculoskeletal Radiology vol. 1 No. 2. pp. 265-272 (1997).

Ryan et al. "Three-Dimensional Finite Element Simulations of Vertebral Body Thermal Treatment"Thermal Treatment of Tissue: Energy Delivery and Assessment III edited by Thomas P. Ryan Proceedings of SPIE vol. 5698 (SPIE Bellingham WA 2005) pp. 137-155.

Shealy C. Norman; Percutaneous radiofrequency denervation of spinal facets Treatment for chronic back pain and sciatica; Journal of Neurosurgery/vol. 43/Oct. 1975.

Sherman Mary S.; The Nerves of Bone The Journal of Bone and Joint Surgery Apr. 1963 pp. 522-528 vol. 45-A No. 3.

Solbiati L. et al. Hepatic metastases: Percutaneous radio-frequency ablation with cooled-tip electrodes. Interventional Radiology vol. 205 No. 2 pp. 367-373 (1997).

Stanton Terry "Can Nerve Ablation Reduce Chronic Back Pain?" AAOS Now Jan. 2012.

The AVAmax System—Cardinal Health Special Procedures Lit. No. 25P0459-01—www.cardinal.com (copyright 2007).

Tillotson L. et al. Controlled thermal injury of bone: Report of a percutaneous technique using radiofrequency electrode and generator. Investigative Radiology Nov. 1989 pp. 888-892.

Troussier B. et al.; Percutaneous Intradiscal Radio-Frequency Thermocoagulation A Cadaveric Study; SPINE vol. 20 No. 15 pp. 1713-1718 1995 Lippincott-Raven Publishers.

Ullrich Jr. Peter F. "Lumbar Spinal Fusion Surgery" Jan. 9, 2013 Spine-Health (available viawayback machine Internet archive at http://web.archive.org/web/20130109095419/http://www/spine-health.com/treatment/spinal-fusion/lumbar-spinal-fusion-surgery).

Weishaupt, D et al,; "Painful Lumbar Disk Derangement: Relevance of Endplate Abnormalities at MR Imaging", Radiology, vol. 218(2), pp. 420-427 (2001).

YouTube Video, "DFINE-STAR Procedure Animation," dated Sep. 30, 2013, can be viewed at https://www.youtube.com/watch?v=YxtKNyc2e-0.

Kim et al., Transforaminal epiduroscopic basivertebral nerve laser ablation for chronic low back pain associated with modic changes: A preliminary open-label study. Pain Research and Management 2018; https://pubmed.ncbi.nlm.nih.gov/30186540.

Rahme et al., The modic vertebral endplate and marrow changes: pathologic significance and relationto low back pain and segmental instability of the lumbar spine. American Journal of Neuroradiology 29.5 (2008): 838-842; http://www.ajnr.org/content/29/5/838.

Macadaeg et al, A prospective single arm study of intraosseous basivertebral nerve ablation for thetreatment of chronic low back pain: 12-month results. North American Spine Society Journal; May 27, 2020, 8 pages.

Vadala et al., "Robotic Spine Surgery and Augmented Reality Systems: A State of the Art", Neurospine Epub Mar. 31, 2020; revised: Feb. 22, 2020; accepted: Feb. 24, 2020; retrieved on [Oct. 6, 2022]. Retrieved from the internet URL:https://www.ncbi.nlm.nih.gov/pmc/articles/PMC7136092/pdf/ns-2040060-030.pdf entire document.

International Search Report and Written Opinion; PCT/US2021/072125; dated Feb. 24, 2022.

U.S. Appl. No. 14/136,763 U.S. Pat. No. 9,023,038, filed Dec. 20, 2013, Denervation Methods.

U.S. Appl. No. 14/174,024 U.S. Pat. No. 9,017,325, filed Jan. 3, 2014, Nerve Modulation Systems.

U.S. Appl. No. 14/153,922 U.S. Pat. No. 9,173,676, filed Jan. 13, 2014, Nerve Modulation Methods.

U.S. Appl. No. 14/695,330 U.S. Pat. No. 9,421,064, filed Apr. 24, 2015, Nerve Modulation Systems.

U.S. Appl. No. 14/701,908, filed May 1, 2015, Denervation Methods.

U.S. Appl. No. 14/928,037 U.S. Pat. No. 10,028,753, filed Oct. 30, 2015, Spine Treatment Kits.

U.S. Appl. No. 15/241,523 U.S. Pat. No. 9,724,107, filed Aug. 19, 2016, Nerve Modulation Systems.

U.S. Appl. No. 15/669,399 U.S. Pat. No. 10,905,440, filed Aug. 4, 2017, Nerve Modulation Systems.

U.S. Appl. No. 16/152,834 U.S. Appl. No. 14/471,171, filed Oct. 5, 2018, Bipolar Radiofrequency Ablation Systems For Treatment Within Bone.

U.S. Appl. No. 16/156,850, filed Oct. 10, 2018, Systems For Treating Nerves Within Bone Using Steam.

U.S. Appl. No. 16/747,830, filed Jan. 21, 2020, Denervation Methods.

U.S. Appl. No. 13/612,541 U.S. Pat. No. 8,361,067 filed Sep. 12, 2012, Methods of Therapeutically Heating a Vertebral Body to Treat Back Pain.

U.S. Appl. No. 13/615,001 U.S. Pat. No. 8,419,731, filed Sep. 13, 2012, Methods of Treating Back Pain.

(56) References Cited

OTHER PUBLICATIONS

U.S. Appl. No. 13/615,300, filed Sep. 13, 2012, System For Heating a Vertebral Body to Treat Back Pain.
U.S. Appl. No. 13/862,317 U.S. Pat. No. 8,992,522, filed Apr. 12, 2013, Back Pain Treatment Methods.
U.S. Appl. No. 13/923,798 U.S. Pat. No. 8,992,523, filed Jun. 12, 2013, Vertebral Treatment.
U.S. Appl. No. 14/673,172 U.S. Pat. No. 9,486,279, filed Mar. 30, 2015, Intraosseous Nerve Treatment.
U.S. Appl. No. 15/344,284 U.S. Pat. No. 10,111,704, filed Nov. 4, 2016, Intraosseous Nerve Treatment.
U.S. Appl. No. 16/153,234 U.S. Pat. No. 10,478,246, filed Oct. 5, 2018, Ablation Of Tissue Within Vertebral Body Involving Internal Cooling.
U.S. Appl. No. 16/153,242 U.S. Pat. No. 10,588,691, filed Oct. 5, 2018, Radiofrequency Ablation Of Tissue Within A Vertebral Body.
Hong Kong, 19124269.2, May 24, 2019, Systems And Methods For Navigation An Instrument Through Bone.
Japan, 2011-529245 5688022, Sep. 25, 2009, Systems And Methods For Navigation An Instrument Through Bone.
Japan, 2015-010950 6027151, Sep. 25, 2009, Systems And Methods For Navigation An Instrument Through Bone.
Japan, 2016-201503 6338253, Sep. 25, 2009, Systems And Methods For Navigation An Instrument Through Bone.
Japan, 2018-088547, May 2, 2018, Systems And Methods For Navigation An Instrument Through Bone.
Australia, 2011204278 2011204278, Jan. 7, 2011, Systems And Methods For Navigation An Instrument Through Bone.
Canada, 2,785,207 2,785,207, Jan. 7, 2011, Systems And Methods For Navigation An Instrument Through Bone.
Europe, 11732213.1 2521501, Jan. 7, 2011, Systems And Methods For Navigation An Instrument Through Bone.
Europe, 20161054.0, Mar. 4, 2020, Systems And Methods For Navigation An Instrument Throught Bone.
Hong Kong, 13105656.9, Jan. 7, 2011, Systems and Methods for Navigation an Instrument Through Bone.
Israel, 220747 220747, Jan. 7, 2011, Systems And Methods For Navigation An Instrument Through Bone.
Israel, 245665 245665, Jan. 7, 2011, Systems And Methods For Navigation An Instrument Through Bones.
Japan, 2012-548169 5179682, Jan. 7, 2011, Systems And Methods For Navigating An Instrument Through Bone.
Japan, 2013-1951, Jan. 7, 2011, Systems And Methods For Navigation An Instrument Through Bone.
WO, PCT/US2011/020535, Jan. 7, 2011, Systems And Methods For Navigation An Instrument Through Bone.
U.S. Pat. No. 10/103,439, U.S. Pat. No. 6,736,835, filed Mar. 21, 2002, Novel Early Intervention Spinal Treatment Methods and Devices for Use Therein.
South Korea, 2003-0017897 10-957458, Mar. 21, 2003, Early Intervention Spinal Treatment And Devices For Use Therein.
Australia, 2019201705 2019201705, Mar. 13, 2019, Systems and Methods for Treating Back Pain.
WO, PCT/US2012/071465, Dec. 21, 2012, Systems and Methods for Treating Back Pain.
U.S. Appl. No. 14/369,661 U.S. Pat. No. 10,369,661, filed Jun. 27, 2014, Systems and Methods for Treating Back Pain.
U.S. Appl. No. 16/205,050 U.S. Pat. No. 11,471,210, filed Nov. 29, 2018, Methods of Denervating Vertebral Body Using External Energy Source.
U.S. Appl. No. 18/047,164, filed Oct. 17, 2022, Methods of Denervating Vertebral Body Using External Energy Source.
WO, PCT/US2013/068012, Nov. 1, 2013, Systems and Methods for Creating Curved Paths Through Bone and Modulating Nerves Within The Bone.
Australia, 2013337680 2013337680, Nov. 1, 2013, Systems and Methods for Creating Curved Paths Through Bone and Modulating Nerves Within The Bone.
Australia, 2019206037 2019206037, Jul. 17, 2019, Systems and Methods for Creating Curved Paths Through Bone and Modulating Nerves Within The Bone.
Australia, 2021200382, Jan. 21, 2021, Systems and Methods for Creating Curved Paths Through Bone and Modulating Nerves Within The Bone.
Canada, 2889478 2889478, Nov. 1, 2013, Systems and Methods for Creating Curved Paths Through Bone and Modulating Nerves Within The Bone.
Canada, 3093398, Sep. 17, 2020, Systems and Methods for Creating Curved Paths Through Bone and Modulating Nerves Within The Bone.
Europe, 13852217.2 2914186, Nov. 1, 2013, Systems and Methods for Creating Curved Paths Through Bone and Modulating Nerves Within The Bone.
Europe, 19162385.9, Mar. 12, 2019, Systems and Methods for Creating Curved Paths Through Bone and Modulating Nerves Within The Bone.
Hong Kong, 16100183.9 HK1212186, Nov. 1, 2013, Systems and Methods for Creating Curved Paths Through Bone and Modulating Nerves Within The Bone.
Israel, 238516 238516, Nov. 1, 2013, Systems and Methods for Creating Curved Paths Through Bone and Modulating Nerves Within The Bone.
Japan, 2015-540810 6195625, Nov. 1, 2013, Systems and Methods for Creating Curved Paths Through Bone and Modulating Nerves Within The Bone.
Japan, 2017-156808 6453397, Nov. 1, 2013, Systems and Methods for Creating Curved Paths Through Bone and Modulating Nerves Within The Bone.
Japan, 2018-232891 6852844, Dec. 12, 2018, Systems and Methods for Creating Curved Paths Through Bone and Modulating Nerves Within The Bone.
U.S. Appl. No. 14/440,050 U.S. Pat. No. 9,775,627, filed Apr. 30, 2015, Systems and Methods for Creating Curved Paths Through Bone and Modulating Nerves Within The Bone.
U.S. Appl. No. 15/722,392 U.S. Pat. No. 10,357,258, filed Oct. 2, 2017, Systems and Methods for Creating Curved Paths Through Bone and Modulating Nerves Within The Bone.
U.S. Appl. No. 16/370,264 U.S. Pat. No. 10,517,611, filed Mar. 29, 2019, Systems For Navigation and Treatment Within a Vertebral Body.
U.S. Appl. No. 16/717,985 U.S. Pat. No. 11,160,563, filed Dec. 17, 2019, Systems For Navigation and Treatment Within a Vertebral Body.
U.S. Appl. No. 17/488,116 U.S. Pat. No. 11,234,764, filed Sep. 28, 2021, Systems For Navigation and Treatment Within a Vertebral Body.
U.S. Appl. No. 17/488,111 U.S. Pat. No. 11,291,502, filed Sep. 28, 2021, Systems For Navigation and Treatment Within a Vertebral Body.
U.S. Appl. No. 17/657,864, filed Apr. 26, 2022, Systems For Navigation and Treatment Within a Vertebral Body.
U.S. Appl. No. 14/454,643 U.S. Pat. No. 9,724,151, filed Aug. 7, 2014, Modulating Nerves Within Bone Using Bone Fasteners.
U.S. Appl. No. 15/669,292 U.S. Pat. No. 10,456,187, filed Aug. 4, 2017, Modulating Nerves Within Bone Using Bone Fasteners.
U.S. Appl. No. 16/661,271 U.S. Pat. No. 11,065,046, filed Oct. 23, 2019, Modulating Nerves Within Bone Using Bone Fasteners.
U.S. Appl. No. 17/378,457, filed Jul. 16, 2021, Modulating Nerves Within Bone.
WO, PCT/US2020/050246, Sep. 10, 2020, Systems and Methods for Tissue Modulation.
U.S. Appl. No. 17/138,203 U.S. Pat. No. 11,123,103, filed Dec. 30, 2020, Introducer Systems for Bone Access.
U.S. Appl. No. 17/138,234 U.S. Pat. No. 11,007,010, filed Dec. 30, 2020, Curved Bone Access Systems.
U.S. Appl. No. 17/302,949 U.S. Pat. No. 11,202,655, filed Mar. 17, 2021, Accessing and Treating Tissue Within a Vertical Body.
U.S. Appl. No. 17/303,254 U.S. Pat. No. 11,426,199, filed Mar. 25, 2021, Methods of Treating a Vertebral Body.
U.S. Appl. No. 17/303,267 U.S. Pat. No. 11,207,100, filed Mar. 25, 2021, Methods of Detecting and Treating Back Pain.

(56) References Cited

OTHER PUBLICATIONS

U.S. Appl. No. 17/645,658, filed Dec. 22, 2021, Methods of Detecting and Treating Back Pain.

U.S. Appl. No. 17/822,700, filed Aug. 26, 2022, Methods of Treating a Vertebral Body.

CA, 3150339, Mar. 7, 2022, Systems and Methods for Tissue Modulation.

EP, 20862138.3, Mar. 8, 2022, Systems and Methods for Tissue Modulation.

WO, PCT/US2021/040843, Jul. 8, 2021, Vertebral Denervation in Conjunction With Vertebral Fusion.

AU, 2021306313, Jan. 25, 2023, Vertebral Denervation in Conjunction With Vertebral Fusion.

U.S. Appl. No. 18/003,760, filed Dec. 29, 2022, Vertebral Denervation in Conjunction With Vertebral Fusion.

U.S. Appl. No. 17/449,051, filed Sep. 27, 2021, Introducer Bill.

WO, PCT/US2021/072125, Oct. 29, 2021, Prediction of Candidates for Spinal Neuromodulation.

AU, 2021409967, Jul. 18, 2023, Prediction of Candidates for Spinal Neuromodulation.

CA, 3202650, Jan. 16, 2023, Prediction of Candidates for Spinal Neuromodulation.

EP, 21912257.9, Jul. 10, 2023, Prediction of Candidates for Spinal Neuromodulation.

IL, 303851, Jun. 19, 2023, Prediction of Candidates for Spinal Neuromodulation.

JP0, 2023-537522, Jun. 20, 2023, Prediction of Candidates for Spinal Neuromodulation.

U.S. Appl. No. 18/258,734, filed Jun. 21, 2023, Prediction of Candidates for Spinal Neuromodulation.

U.S. Appl. No. 18/339,007, filed Jun. 21, 2023, Candidate Determination For Spinal Neuromodulation.

WO, PCT/US2022/019954, Mar. 11, 2022, Robotic Spine Systems and Robotic-Assisted Methods for Tissue Modulation.

U.S. Appl. No. 18/053,284, filed Nov. 7, 2022, Impedance Stoppage Mitigation During Radiofrequency Tissue Ablation Procedures.

WO, PCT/US2023/017913, Apr. 7, 2023, Controlled Bone Access And Operator Feedback Features.

U.S. Appl. No. 09/775,137 U.S. Pat. No. 6,699,242, filed Feb. 1, 2001, Methods and Devices For Intraosseous Nerve Ablation.

Australia, 2001033279 774022, Feb. 1, 2001, Methods and Devices For Intraosseous Nerve Ablation.

Canada, 2,397,413 2,397,413, Feb. 1, 2001, Methods and Devices For Intraosseous Nerve Ablation.

Canada, 2,723,071 2,723,071, Feb. 1, 2001, Methods and Devices For Intraosseous Nerve Ablation.

Europe, 1905397.4 1255500, Feb. 1, 2001, Devices For Intraosseous Nerve Ablation.

Europe, 7010394 1844723, Feb. 1, 2001, Methods and Devices For Intraosseous Nerve Ablation.

Europe, 7010581.2 1832244, Feb. 1, 2001, Methods and Devices For Intraosseous Nerve Ablation.

Europe, 16197060.3 3143958, Feb. 1, 2001, Methods and Devices For Intraosseous Nerve Ablation.

Europe, 7010649.7, Feb. 1, 2001, Methods and Devices For Intraosseous Nerve Ablation.

Europe, 10012521, Feb. 1, 2001, Methods and Devices For Intraosseous Nerve Ablation.

Hong Kong, 8103900.5 1109847, Feb. 1, 2001, Methods and Devices For Intraosseous Nerve Ablation.

Hong Kong, 8102841.9 1108617, Feb. 1, 2001, Methods and Devices For Intraosseous Nerve Ablation.

Hong Kong, 17108246.6 1234625, Feb. 1, 2001, Devices For Intraosseous Nerve Ablation.

Japan, 2001-556439 4916635, Feb. 1, 2001, Methods and Devices For Intraosseous Nerve Ablation.

U.S. Appl. No. 10/401,854 7,258,690, filed Mar. 28, 2003, Windowed Thermal Ablation Probe.

U.S. Appl. No. 11/745,446, filed May 7, 2007, Windowed Thermal Ablation Probe.

U.S. Appl. No. 12/643,997, filed Dec. 21, 2009, Windowed Thermal Ablation Probe.

U.S. Appl. No. 13/655,683 U.S. Pat. No. 8,882,764, filed Oct. 19, 2012, Thermal Denervation Devices.

U.S. Appl. No. 14/535,868 U.S. Pat. No. 9,848,944, filed Nov. 7, 2014, Thermal Denervation Devices and Methods.

U.S. Appl. No. 15/845,699, filed Dec. 18, 2017, Thermal Denervation Devices and Methods.

U.S. Appl. No. 16/153,407 U.S. Pat. No. 10,463,423, filed Oct. 5, 2018, Thermal Denervation Devices and Methods.

U.S. Appl. No. 10/260,879 U.S. Pat. No. 6,907,884, filed Sep. 30, 2002, Method of Straddling An Intraosseous Nerve.

U.S. Appl. No. 11/123,766 U.S. Pat. No. 7,749,218, filed May 6, 2005, Method of Straddling An Intraosseous Nerve.

U.S. Appl. No. 12/683,555 U.S. Pat. No. 8,613,744, filed Jan. 7, 2010, Systems and Methods for Navigating an Instrument Throught Bone.

U.S. Appl. No. 13/612,561 U.S. Pat. No. 8,425,507, filed Sep. 12, 2012, Basivertebral Nerve Denervation.

U.S. Appl. No. 13/617,470 U.S. Pat. No. 8,623,014, filed Sep. 14, 2012, Systems For Denervation of Basivertebral Nerves.

U.S. Appl. No. 13/862,306 U.S. Pat. No. 8,628,528, filed Apr. 12, 2013, Vertebral Denervation.

U.S. App. No. 14/136,763 U.S. Pat. No. 9,023,038, filed Dec. 20, 2013, Denervation Methods.

U.S. Appl. No. 14/695,330 U.S. Pat. No. 9,421,064, filed Apr. 24, 2025, Nerve Modulation Systems.

U.S. Appl. No. 14/701,908, filed May 1, 2015, Devervation Methods.

U.S. Appl. No. 16/153,234 U.S. Pat. No. 11,471,171, filed Oct. 5, 2018, Bipolar Radiofrequency Ablation Systems For Treatment Within Bone.

U.S. Appl. No. 18/451,539, filed Aug. 17, 2023, Systems for Treating Nerves Within Bone.

U.S. Appl. No. 13/615,001 U.S. Pat. 8,419,731, filed Sep. 13, 2012, Methods of Treating Back Pain.

U.S. Appl. No. 16/160,155 U.S. Pat. No. 11,596,468, filed Oct. 15, 2018, Intraosseous Nerve Treatment.

U.S. Appl. No. 16/818,092 U.S. Pat. No. 11,737,814, filed Mar. 13, 2020, Radiofrequency Ablation Of Tissue Within A Vertebral Body.

U.S. Appl. No. 17/394,189 U.S. Pat. No. 11,701,168, filed Aug. 4, 2021, Radiofrequency Ablation Of Tissue Within A Vertebral Body.

U.S. Appl. No. 17/394,166 U.S. Pat. No. 11,690,667, filed Aug. 4, 2021, Radiofrequency Ablation Of Tissue Within A Vertebral Body.

U.S. Appl. No. 18/360,724, filed Jul. 27, 2023, Radiofrequency Ablation Of Tissue Within A Vertebral Body.

U.S. Appl. No. 13/541,591 (Reissue of U.S. Pat. No. 7,749,218) RE46356, filed Jul. 3, 2012, Method of Treating an Intraosseous Nerve.

U.S. Appl. No. 15/469,315 (Reissue of U.S. Pat. No. 7,749,218) RE48460, filed Mar. 24, 2017, Method of Treating an Intraosseous Nerve.

U.S. Appl. No. 16/153,598, filed Oct. 5, 2018, Method of Treating an Intraosseous Nerve.

U.S. Appl. No. 16/153,603, filed Oct. 5, 2018, Method of Treating an Intraosseous Nerve.

U.S. Appl. No. 17/193,491, filed Mar. 5, 2021, Method of Treating an Introsseous Nerve.

Australia, 2003248436 2003248436, Sep. 29, 2003, Method Of Straddling An Intraosseous Nerve.

Australia, 2008249202 2008249202, Sep. 29, 2003, Method Of Straddling An Intraosseous Nerve.

Australia, 2011218612 2011218612, Sep. 29, 2003, Method Of Straddling An Intraosseous Nerve.

Canada, 2,443,491 2,433,491, Sep. 29, 2003, Method Of Straddling An Intraosseous Nerve.

Europe, 3256168 1402838, Sep. 29, 2003, Intraosseous Nerve Denervation Device.

Europe, 5021597.9 1611860, Sep. 29, 2003, Intraosseous Nerve Denervation Device.

Europe, 10012523.6, Sep. 29, 2003, Intraosseous Nerve Denervation Device.

(56) References Cited

OTHER PUBLICATIONS

Japan, 2003-341164 4540959, Sep. 29, 2003, Method Of Straddling An Intraosseous Nerve.

Japan, 2009-269652 5203338, Sep. 29, 2003, Method Of Straddling An Intraosseous Nerve.

Japan, 2012-246075 5653986, Sep. 29, 2003, Method Of Straddling An Intraosseous Nerve.

U.S. Appl. No. 12/566,895 U.S. Pat. No. 8,419,730, filed Sep. 25, 2009, Systems and Methods for Navigating an Instrument Through Bone.

U.S. Appl. No. 13/963,767 U.S. Pat. No. 9,039,701, filed Aug. 9, 2013, Channeling Paths Into Bond.

U.S. Appl. No. 13/862,242 U.S. Pat. No. 9,259,241, filed Apr. 12, 2013, Systems for Accessing Nerves Within Bone.

U.S. Appl. No. 15/040,268 U.S. Pat. No. 10,265,099, filed Feb. 10, 2016, Systems for Accessing Nerves Within Bones.

U.S. Appl. No. 16/368,453, filed Mar. 28, 2019, Systems for Accessing Nerves Within Bones.

U.S. Appl. No. 12/868,818 U.S. Pat. No. 8,808,284, filed Aug. 26, 2010, Systems for Navigating an Instrument Through Bone.

U.S. Appl. No. 14/462,371 U.S. Pat. No. 9,265,522, filed Aug. 18, 2014, Methods for Navigating an Instrument Through Bone.

U.S. Appl. No. 13/543,712 U.S. Pat. No. 8,535,309, filed Jul. 6, 2012, Vertebral Bone Channeling Systems.

U.S. Appl. No. 13/543,723 U.S. Pat. No. 8,414,571, filed Jul. 6, 2012, Vertebral Bone Navigation Systems.

U.S. Appl. No. 13/543,721, filed Jul. 6, 2012, Intraosseous Nerve Denervation Methods.

WO, PCT/US2009/058329, Sep. 25, 2009, Systems And Methods For Navigating An Instrument Through Bone.

Australia, 2009296474 2009296474, Sep. 25, 2009, Systems And Methods For Navigating An Instrument Throth Bone.

Australia, 2015234376 2015234376, Sep. 25, 2009, Systems And Methods For Navigating An Instrument Through Bone.

Australia, 2018223007 2018223007, Sep. 25, 2009, Systems and Methods For Navigating An Instrument Through Bone.

Australia, 2020201962, Mar. 18, 2020, Systems and Methods For Navigating An Instrument Through Bone.

Canada, 2,737,374 2,737,374, Sep. 25, 2009 2737374, Systems And Methods For Navigating An Instrument Through Bone.

Canada, 2,957,010 2,957,010, Sep. 25, 2009, Systems And Methods For Navigating An Instrument Through Bone.

Europe, 9816892.5 2,339,972, Sep. 25, 2009, Systems And Methods For Navigating An Instrument Through Bone.

Europe, 18166323.8, Apr. 9, 2018, Systems And Methods For Navigating An Instrument Through Bone.

Hong Kong, 12100034.4 HK 1159454, Sep. 25, 2009, Systems And Methods For Navigating An Instrument Through Bone.

Hong Kong, 19124269.2, May 24, 2019, Systems And Methods For Navigating An Instrument Through Bone.

Japan, 2011-529245 5688022, Sep. 25, 2009, Systems And Methods For Navigating An Instrument Through Bone.

Japan, 2015-010950 6027151, Sep. 25, 2009, Systems And Methods For Navigating An Instrument Through Bone.

Japan, 2016-201503 6338253, Sep. 25, 2009, Systems And Methods For Navigating An Instrument Through Bone.

Japan, 2018-088547, May 2, 2018, Systems And Methods For Navigating An Instrument Through Bone.

Australia, 2011204278 2011204278, Jan. 7, 2011, Systems And Methods For Navigating An Instrument Through Bone.

Canada, 2,785,207 2,785,207, Jan. 7, 2011, Systems And Methods For Navigating An Instrument Through Bone.

Europe, 11732213.1 2521501, Jan. 7, 2011, Systems And Methods For Navigating An Instrument Through Bone.

Europe, 20161054.0, Mar. 4, 2020, Systems And Methods For Navigating An Instrument Through Bone.

Hong Kong, 13105656.9, Jan. 7, 2011, Systems and Methods for Navigating an Instrument Through Bone.

Israel, 220747 220747, Jan. 7, 2011, Systems And Methods For Navigating An Instrument Through Bone.

Israel, 245665 245665, Jan. 7, 2011, Systems And Methods For Navigating An Instrument Through Bones.

Japan, 2013-1951, Jan. 7, 2011, Systems And Methods For Navigating An Instrument Through Bone.

WO, PCT/US2011/020535, Jan. 7, 2011, Systems And Methods For Navigating An Instrument Through Bone.

U.S. Appl. No. 10/103,439 U.S. Pat. No. 6,736,835, filed Mar. 21, 2002, Novel Early Intervention Spinal Treatment Methods and Devices for Use Therein.

Australia, 2012362524 2012362524, Dec. 21, 2012, Systems and Methods for Treating Back Pain.

WO, PCT/U82013/068012, Nov. 1, 2013, Systems and Methods for Creating Curved Paths Through Bone and Modulating Nerves Within The Bone.

Australia, 2021200382 2021200382, Jan. 21, 2021, Systems and Methods for Creating Curved Paths Through Bone and Modulating Nerves Within The Bone.

Australia, 2023204019, Jun. 26, 2023, Systems and Methods for Creating Curved Paths Through Bone and Modulating Nerves Within The Bone.

Canada, 2889478 2889478, Nov. 1, 2013, Systems and Methods for Creating Curved Paths Through Bone and Modulating Nerves Within The Bone.

Canada, 3093398 3093398, Sep. 17, 2020, Systems and Methods for Creating Curved Paths Through Bone and Modulating Nerves Within The Bone.

Japan, 2017-156808 2017-156808, Nov. 1, 2013 Systems and Methods for Creating Curved Paths Through Bone and Modulating Nerves Within The Bone.

Japan, 2021-026929 6982704, Feb. 24, 2021, Systems and Methods for Creating Curved Paths Through Bone and Modulating Nerves Within the Bone.

U.S. Appl. No. 16/370,264 U.S. Pat. No. 11,234,764, filed Mar. 29, 2019, Systems For Navigation and Treatment Within a Vertebral Body.

U.S. Appl. No. 17/488,111 U.S. Pat. No. 11,291,502, filed Sep. 28, 2021, Methods of Navigation and Treatment Within a Vertebral Body.

U.S. Appl. No. 17/657,864, filed Apr. 4, 2022, Methods of Navigation and Treatment Within a Vertebral Body.

WO, PCT/US2020/050249, Sep. 10, 2020, Systems and Methods for Tissue Modulation.

AU, 2020346827, Mar. 11, 2022, Systems and Methods for Tissue Modulation.

U.S. Appl. No. 17/138,203 U.S. Pat. No. 11,123,103, Dec. 30, 2020, Introducer Systems for Bone Access.

U.S. Appl. No. 17/302,949 U.S. Pat. No. 11,202,655, filed Mar. 17, 2021, Accessing and Treating Tissue Within a Vettical Body.

U.S. Appl. No. 17/303,254 U.S. Pat. No. 11,426,199, filed May 25, 2021, Methods of Treating a Vertebral Body.

U.S. Appl. No. 17/303,267 U.S. Pat. No. 11,207,100, filed May 25, 2021, Methods of Detecting and Treating Back Pain.

U.S. Appl. No. 17/449,051, filed Sep. 27, 2021, Introducer Drill.

WO, PCT/US2021/82125, Oct. 29, 2021, Prediction of Candidates for Spinal Neuromodulation.

CA, 3202650, Jun. 16, 2023, Prediction of Candidates for Spin Neuromodulation.

EP, 21912257.9, 107/10/2023, Prediction of Candidates for Spinal Neuromodulation.

JP, 2023-537522, Jun. 20, 2023, Prediction of Candidates for Spinal Neuromodulation.

U.S. Appl. No. 18/339,007, filed Jun. 31, 2023, Prediction of Candidates for Spinal Neuromodulation.

AU, 2022239314, Sep. 12, 2023, Robotic Spine Systems and Robotic-Assisted Methods for Tissue Modulation.

CA, 3211365, Sep. 7, 2023, Robotic Spine Systems and Robotic-Assisted Methods for Tissue Modulation.

EP, 22771962.2, Sep. 16, 2023, Robotic Spine Systems and Robotic-Assisted Methods for Tissue Modulation.

JP, 2023-555601, Sep. 11, 2023, Robotic Spine Systems and Robotic-Assisted Methods for Tissue Modulation.

U.S. Appl. No. 18/550,040, filed Sep. 11, 2023, Robotic Spine Systems and Robotic-Assisted Methods for Tissue Modulation.

(56) References Cited

OTHER PUBLICATIONS

U.S. Appl. No. 18/053,284, filed Nov. 7, 2022, Impedance Stoppage Mitigation During Radiofrequency Tissue Ablatior Procedures.
Azimi, Parisa "Use of artificial neural networks to predict surgical satisfaction in patients with lumbar spinal canal stenosis." J Neurosurg Spine 20. (Year: 2014).
International Preliminary Report on Patentability received for PCT Patent Application No. PCT/US21/72125, mailed on Jul. 6, 2023, 14 pages.

* cited by examiner

200

START

RECEIVE IMAGES OF AT LEAST A PORTION OF A PATIENT SPINE — 202

ANALYZE IMAGES TO IDENTIFY AND QUANTIFY MULTIPLE INDICATORS OF BACK PAIN — 204

GENERATE OBJECTIVE PREDICTION OF LIKELIHOOD OF FAVORABLE RESPONSE TO BASIVERTEBRAL NERVE ABLATION — 206

GENERATE CONFIDENCE LEVEL BASED ON ADDITIONAL INDICATORS — 208

END

300

START

302 — RECEIVE IMAGES OF PATIENT CANDIDATE

304 — APPLY PRE-PROCESSING

306 — EXTRACT FEATURES FROM IMAGES

308 — ANALYZE EXTRACTED FEATURES

310 — DETERMINE WHETHER PATIENT CANDIDATE LIKELY TO RESPOND FAVORABLY TO TREATMENT

312 — POST-PROCESSING REFINEMENT

END

CANDIDATE DETERMINATION FOR SPINAL NEUROMODULATION

RELATED APPLICATIONS

This application is a continuation of International PCT Application No. PCT/US2021/072125, filed Oct. 29, 2021, which claims priority to U.S. Provisional Application No. 63/129,374 filed Dec. 22, 2020, the entire content of each of which is hereby incorporated by reference herein.

FIELD

Described herein are various implementations of systems and methods for identifying patients who may respond favorably to spinal neuromodulation procedures (e.g., ablation of a basivertebral nerve trunk or other intraosseous nerves within a vertebral body, such as nerves innervating vertebral body endplates) to prevent and/or treat back pain (e.g., chronic lower back pain). The systems and methods described herein may incorporate artificial intelligence techniques (e.g., trained algorithms, machine learning or deep learning algorithms, or neural networks). Several embodiments comprise the use of a combination of indicators, or factors, (e.g., characteristics identified from ultra-short time-to-echo ("UTE") magnetic resonance imaging, characteristics identified from conventional T1- or T2-weighted magnetic resonance imaging, characteristics identified from other imaging modalities, multifidus muscle characteristics (e.g., atrophy), disc calcification, bone turnover, and/or other biomarkers) to identify patients likely to have back pain that would result in a favorable response to the spinal neuromodulation procedures (e.g., back pain stemming from one or more vertebral bodies or vertebral endplates).

BACKGROUND

Back pain is a very common health problem worldwide and is a major cause for work-related disability benefits and compensation. At any given time, low back pain impacts nearly 30% of the US population, leading to 62 million annual visits to hospitals, emergency departments, outpatient clinics, and physician offices. Back pain may arise from strained muscles, ligaments, or tendons in the back and/or structural problems with bones or spinal discs. The back pain may be acute or chronic. Existing treatments for chronic back pain vary widely and include physical therapy and exercise, chiropractic treatments, injections, rest, pharmacological therapy such as opioids, pain relievers or anti-inflammatory medications, and surgical intervention such as vertebral fusion, discectomy (e.g., total disc replacement), or disc repair. Existing treatments can be costly, addictive, temporary, ineffective, and/or can increase the pain or require long recovery times. In addition, existing treatments do not provide adequate relief for the majority of patients and only a small percentage are surgically eligible.

SUMMARY

Applicant's existing technology (the Intracept® System and Procedure provided commercially by Relievant Medsystems, Inc.) offers a safe and effective minimally invasive procedure that targets (e.g., ablates) the basivertebral nerve (and/or other intraosseous nerves or nerves innervating a vertebral endplate) for the relief of chronic low back pain. As disclosed herein, several embodiments provide systems and methods for determining (e.g., via an automated computer-implemented method) whether patients have back pain (e.g., chronic low back pain) originating from one or more vertebral bodies or vertebral endplates, and thus are likely to respond favorably to basivertebral nerve ablation (such as provided by Applicant's existing Intracept® Procedure) or other spinal neuromodulation procedures.

The determination may be based on a combination (e.g., weighted combination) of indicators, or factors. For example, a method may involve generating (e.g., calculating, determining) an objective or quantitative score or other output (e.g., percentage value, numerical value on a scale, binary YES/NO output) based on identification and analysis of the combination of indicators, or factors, indicative of a likelihood of a favorable response (e.g., pain prevention or pain relief) to a particular spinal neuromodulation procedure (e.g., basivertebral nerve ablation treatment within one or more vertebral bodies of the patient). In other words, the method provides an objective or quantitative prediction or assessment (as opposed to a subjective or qualitative prediction or assessment) as to whether the particular spinal neuromodulation procedure is likely to be successful in treating the back pain (e.g., chronic low back pain whose source is in one or more vertebral bodies or vertebral endplates). A clinical professional may decide whether or not to perform the particular spinal neuromodulation procedure based on the objective or quantitative prediction or assessment (e.g., score). For example, if the objective or quantitative prediction or assessment is above a predetermined threshold, a treatment recommendation or treatment protocols may be provided and a clinician may decide to provide treatment or adjust treatment based on the recommendation or protocols.

In accordance with several embodiments, the quantitative score, value, or other output may be generated based on execution of one or more computer-implemented algorithms stored (e.g., on non-transitory computer-readable storage media) and executed by one or more processors (e.g., one or more hardware processors of a server). The quantitative score, value, or other output may be based on a combination (e.g., weighted) combination of multiple indicators. Some indicators may be weighted more, or deemed more important to the quantitative prediction or assessment, than others. For example, the algorithms may generate the quantitative score, value, or other output based on identification and analysis of one or more indicators (e.g., higher-tier or first-tier indicators) that have been deemed through clinical studies or past experience to have a strong correlation with, and/or are more reliable for predicting, the type of back pain that would be successfully treated by the particular spinal neuromodulation procedure (e.g., basivertebral nerve ablation procedure). In some implementations, vertebrae having a quantitative score (e.g., quantitative endplate score) above a threshold may be deemed as potential candidates for treatment (e.g., basivertebral nerve ablation). The quantitative score may comprise a quantitative endplate score based on severity, extent, and/or quantity of identified indicators (e.g., indicators of pain originating from one or more vertebral endplates).

The algorithms (e.g., program instructions stored on non-transitory computer-readable storage media and executed by one or more hardware processors) may also verify, or provide additional confidence in, the quantitative score or other output based on identification and analysis of one or more additional indicators (e.g., lower-tier or second-tier indicators) that may correlate with, and/or be reliable for predicting, the type of back pain (e.g., chronic low back pain) that would be successfully treated by the particular spinal neuromodulation procedure (e.g., basivertebral nerve ablation procedure). The verification or confidence check may advantageously help to reduce false positives or false negatives. Any one factor, or indicator, may not be completely reliable or accurate in predicting likelihood of a successful treatment. In addition, making subjective predictions based on visualization and/or subjective feedback or pain scores from a patient alone may also not be reliably accurate. Identifying indicators and/or generating objective scores based on trained algorithms that have been trained based on former patient data or other reference data can generate more reliable objective scores and treatment recommendations or treatment protocols, thereby resulting in higher patient satisfaction and reducing unnecessary treatments that are likely to be ineffective or providing more specifically tailored treatment protocols.

The type of back pain desired to be treated by the particular spinal neuromodulation procedure (e.g., basivertebral nerve ablation procedure) may be pain originating from one or more vertebral bodies or vertebral endplates (e.g., pain originating from a basivertebral nerve trunk or other intraosseous nerves within a vertebral body or nerves innervating a vertebral endplate). In one embodiment, the type of back pain desired to be treated is not discogenic back pain originating from one or more intervertebral discs. However, in some embodiments, discogenic back pain may be additionally treated even if not the focus or target of the treatment or procedure. The indicators, or factors, may include indicators of pain originating from one or more intervertebral discs.

The algorithms may involve application of artificial intelligence techniques or trained algorithms (e.g., machine learning or deep learning models and algorithms implemented by trained artificial neural networks). Portions of the algorithms may be applied to trained neural networks to facilitate identification of indicators and/or to facilitate calculation of the objective scores. The indicators, or factors, may be identified from, for example, various images obtained using one or more imaging modalities or techniques (e.g., magnetic resonance imaging ("MRI") images such as conventional T1- and/or T2-weighted MRI imaging, fat suppression MRI imaging, ultrashort time-to-echo ("UTE") MRI sequenced imaging, Iterative Decomposition of water and fat with Echo Asymmetry and Least-squares estimation ("IDEAL") MRI sequenced imaging, fast spin echo MRI sequenced imaging, computed tomography ("CT") imaging including single-photon emission computed tomography ("SPECT") imaging, positron emission tomography ("PET") bone imaging, X-ray imaging, fluoroscopy, and/or other imaging modalities or techniques).

The images may include images of a particular patient and may also include images of other patients or subjects (e.g., for comparison and/or for training of neural networks for artificial intelligence implementations). The indicators, or factors, may include an identification of one or more characteristics based on the images (e.g., tissue characteristics such as amount of atrophy of paraspinal muscles surrounding a particular vertebral body or a spine in general, vertebral endplate defects or degradation, bone marrow intensity changes such as Modic changes or pre-Modic change characteristics, vertebral fat fraction, shifts in ratio of water to fat in bone marrow, active bone turnover, intervertebral disc calcification, etc.). Modic changes may include, for example, Type 1 Modic changes or Type 2 Modic changes. The one or more indicators, or factors, determined from the images may include edema, inflammation, and/or tissue changes (e.g., tissue lesions, fibrosis, fissures, or other changes in tissue type or characteristics) of bone, bone marrow, and/or endplate lining, contour or profile. Vertebral endplate defects may include, for example, focal defects, erosive defects, rim defects, and corner defects of a vertebral endplate of the vertebral body. The indicators, or factors, may include an identification of particular spinal anatomical characteristics or conditions (e.g., scoliosis, slipped discs, herniated discs, joint dysfunction, spondylosis, osteoarthritis, spinal stenosis, kyphosis, spondylolisthesis, etc.).

The indicators, or factors, may also include assessment of one or more biomarkers (e.g., biomarkers associated with pain, inflammation, or neurotransmission). Biomarkers may also be used to assess whether a particular subject is likely to be a candidate for nerve ablation treatment for treatment of back pain. For example, the biomarkers may be indicative of pre-Modic changes or symptoms likely to result in Modic changes or endplate damage (e.g., inflammation, edema, bone marrow lesions or fibrosis). The assessment of biomarker levels may indicate which vertebral bodies of a particular subject are candidates for treatment to prevent (or reduce the likelihood of) back pain from developing or worsening or to treat existing back pain. The pre-procedure biomarker assessment may also be combined with pre-procedure imaging. The biomarkers may include one or more of: an inflammatory cytokine (e.g., interleukins, interferons, tumor necrosis factors, prostaglandins, and chemokines), pain indicators (e.g., substance P, calcitonin gene-related peptides (CGRPs)), an edema factor, and/or other inflammatory factor. The biomarkers may be obtained, for example, from one or more blood serum samples (e.g., blood plasma). The biomarkers may be obtained over an extended period of time (e.g., a period of days, weeks, or months) or at a single instance in time. Biomarkers may also be identified in the images themselves and may be the tissue characteristics, bone marrow intensity changes, etc. described above.

The indicators, or factors, may also include patient parameters, information, or risk factors such as age, gender, body mass index, bone mineral density measurements, back pain history, indication of prior spine treatments (such as spinal fusion or discectomy procedures), patient-reported outcomes or quality-of-life measures, and/or other known risk factors for vertebral endplate degeneration or defects (such as smoking, occupational or recreational physical demands or situations) in identifying candidate patients and/or candidate vertebral bodies for treatment (e.g., basivertebral nerve ablation).

In accordance with several embodiments, a method of quantitatively predicting likelihood that a particular subject (e.g., human) would respond favorably to basivertebral nerve ablation to treat back pain (e.g., the INTRACEPT® nerve ablation procedure performed using the commercial technology of Relievant Medsystems, Inc.) is provided. The method includes identifying a plurality of indicators of back pain (e.g., chronic low back pain) based on one or more images of at least a portion of the particular subject's spine (e.g., lumbosacral region of the spine). The method may further include quantifying the identified plurality of indicators and calculating an objective score indicative of a likelihood that the particular subject would respond favorably to basivertebral nerve ablation based on the quantifying of the identified plurality of indicators. The entire method or portions of the method may be fully computer-implemented and automated.

The images may be obtained, for example, from one or more of the following imaging modalities: MRI imaging, T1-weighted MRI imaging, T2-weighted MRI imaging, fat suppression MRI imaging, UTE MRI sequenced imaging, IDEAL MRI sequenced imaging, fast spin echo MRI sequenced imaging, CT imaging, PET bone imaging, X-ray imaging, and fluoroscopy. The images may include images of a particular patient and may also include images of other patients or subjects (e.g., for comparison and/or for training of neural networks for artificial intelligence implementations).

Identifying the plurality of indicators includes identifying one or more bone marrow intensity changes and/or identifying one or more vertebral endplate defects or characteristics of vertebral endplate degeneration. The plurality of indicators may each fall within only one of these two categories in some embodiments. For example, there may be multiple identified indicators (e.g., different spatial locations, different types, different subgroups or sub-sets within the same category or classification) within the overall category or classification of bone marrow intensity changes or within the overall category or classification of vertebral endplate degeneration or defects. The plurality of indicators may be classified as both bone marrow intensity changes and vertebral endplate defects or characteristics of vertebral endplate degeneration.

Identifying one or more bone marrow intensity changes may include identifying the one or more bone marrow intensity changes as either a Type 1 Modic change or a Type 2 Modic change (or optionally a Type 3 Modic change). Identifying one or more vertebral endplate defects or characteristics of vertebral endplate degeneration may include identifying irregularities or deviations to a normal continuous lining of the vertebral endplate, identifying deviations from a normal contour profile of a vertebral endplate, identifying fat fraction changes, and/or identifying one or more phenotype subtypes of vertebral endplate defects.

Quantifying the identified plurality of indicators may include determining a quantity of the bone marrow intensity changes and/or vertebral endplate defects, determining a level of extent (e.g., spatial distribution, prevalence) of the bone marrow intensity changes and/or vertebral endplate defects, and/or quantifying identified fat fraction changes.

The method may further include determining a confidence level in the objective score based on one or more additional indicators of back pain, such as changes in multifidus muscle characteristics, bone turnover identified in SPECT images, and/or a pain score obtained for the particular subject (e.g., Oswestry Disability Index scores, Visual Analogue pain scores). In other implementations, these additional indicators are used in determining the objective score and not in determining a separate confidence level in the objective score. The method may further include displaying an output of the objective score on a display. The output may be a numerical score on a scale, a binary YES or NO output, a percentage score, and/or the like.

In accordance with several embodiments, a method (e.g., computer-implemented method executed by one or more hardware processors) of quantitatively predicting likelihood that a particular subject would respond favorably to basivertebral nerve ablation to treat back pain includes receiving one or more images (e.g., MRI images) of at least a portion of a spine of the particular subject, applying pre-processing imaging techniques to the one or more images, extracting features from the one or more images to identify a plurality of indicators of back pain, and determining an objective score indicative of a likelihood that the particular subject would respond favorably to basivertebral nerve ablation based on the extracting. The plurality of indicators may include (i) bone marrow intensity changes and/or (ii) vertebral endplate defects or characteristics of vertebral endplate degeneration. Extracting the features from the one or more images may include applying a trained neural network to the one or more images to automatically identify the plurality of indicators of back pain. Determining the objective score may also include applying a trained neural network to the extracted features. In some embodiments, the plurality of indicators may also include additional indicators in addition to bone marrow intensity changes and/or vertebral endplate defects or characteristics of vertebral endplate degeneration.

The method may further include applying one or more rules on the extracted features to generate a confidence level. The one or more rules may be based on one or more additional indicators, such as the additional indicators described herein. The additional indicators, for example, may be an indicator in the other of the two categories (either bone marrow intensity changes or vertebral endplate defects or vertebral endplate degeneration). Determining an objective score may include quantifying the plurality of indicators. The quantifying may be based on an extent (e.g., quantity of indicators, severity of indicators (e.g., size or volume) and/or spatial assessment (prevalence in different locations or regions of a vertebral body or endplate or other location). The method may further include displaying an output of the objective score on a display (e.g., monitor of a desktop or portable computing device).

In accordance with several embodiments, a method (e.g., computer-implemented method comprising stored program instructions executed by one or more hardware processors) of quantitatively predicting likelihood that a particular subject would respond favorably to basivertebral nerve ablation to treat chronic low back pain includes receiving one or more magnetic resonance images (MRIs) of at least a lumbosacral region of a spine of the particular subject, applying pre-processing imaging techniques to the one or more MRIs in order to provide uniformity of the one or more MRIs for feature detection, detecting features from the one or more MRIs to identify a plurality of indicators of chronic low back pain, quantifying the identified plurality of indicators based on an extent of the plurality of indicators, wherein the extent may comprise a quantity, a severity, and/or a spatial assessment, and determining an objective score indicative of a likelihood that the particular subject would respond favorably to a basivertebral nerve ablation procedure based on said quantifying. The plurality of indicators can include both bone marrow intensity changes and vertebral endplate defects or characteristics of vertebral endplate degeneration or multiple indicators (e.g., subgroups or subsets) within only one of these categories or classifications.

In accordance with several embodiments, a computer-implemented method (e.g., executed of stored program instructions by one or more hardware processors) of training a neural network for determining whether or not a particular subject is a likely candidate for a successful basivertebral nerve ablation procedure includes collecting a set of digital images from a database. For example, each digital image may comprise a digital image of at least a portion of a spine of a subject having at least one indicator of back pain (e.g., chronic low back pain stemming from one or more vertebral endplates or vertebral bodies and/or stemming from one or more intervertebral discs). The method further includes applying one or more transformations to each digital image to create a modified set of digital images. The method also includes creating a first training set comprising the collected set of digital images, the modified set of digital images, and a set of digital images of at least a portion of a spine of one or more subjects without any indicators of chronic low back pain (e.g., healthy subjects). The method further includes training the neural network in a first stage using the first training set, creating a second training set for a second stage of training comprising the first training set and digital images of at least a portion of a spine of one or more subjects without any indicators of chronic low back pain that are incorrectly determined as having at least one indicator of chronic low back pain, and training the neural network in a second stage using the second training set.

The digital images may comprise magnetic resonance images, computed tomography images, X-ray images, or other types of images described herein. The digital images may alternatively be analog images in some embodiments.

Applying one or more transformations may include pre-processing the collected set of magnetic resonance images in order to make the magnetic resonance images more uniform for training. The pre-processing may include rotating, cropping, enlarging, reducing, removing noise, segmenting, smoothing, contrast or color enhancing, and/or other image processing techniques. The pre-processing may also include spatial orientation identification, vertebral level identification, general anatomical feature identification, and/or the like. In some embodiments, the pre-processing may be performed by running the images through a previously-trained neural network trained to clean up, enhance, reconstruct, or otherwise improve the quality of images, such as noisy MRI images.

The method may also include identifying indicators of back pain that is likely to be successfully treated by the basivertebral nerve ablation procedure in at least some of the collected set of magnetic resonance images. The method may include identifying images of the collected set of magnetic resonance images for which the subjects were successfully treated by the basivertebral nerve ablation procedure. In some embodiments, the collected set of magnetic resonance images comprises magnetic resonance images of subjects that previously received a spinal fusion or a discectomy procedure, or other procedure that may have resulted in indicators or factors of chronic low back pain (e.g., irritated vertebral endplates or vertebral endplate degeneration or defects or bone marrow intensity changes or multifidus muscle atrophy).

The systems and methods described herein may also be applied to identification of pain other than back pain. For example, the systems and methods may be applied to peripheral nerve pain. In accordance with several embodiments, a method of quantitatively predicting likelihood that a particular subject would respond favorably or unfavorably to neuromodulation includes identifying a plurality of indicators of back and/or peripheral nerve pain, quantifying the identified plurality of indicators, and calculating an objective score indicative of a likelihood that the particular subject would respond favorably or unfavorably to said neuromodulation based on the quantifying. Identifying the plurality of indicators may include identifying one or more bone marrow intensity changes and/or identifying one or more vertebral endplate defects or characteristics of vertebral endplate degeneration. However, other indicators may alternatively or additionally be identified (e.g., for peripheral nerve pain or for back pain other than chronic low back pain).

The plurality of indicators may be identified based on imaging data (such as magnetic resonance imaging data). The plurality of indicators may be identified based on scanned data. The plurality of indicators may be identified based on acoustic data. The data may be stored and retrieved from memory or may be received in real-time from an imaging device (e.g., MRI scanner) The plurality of indicators may be automatically identified by computer processing techniques and algorithms (e.g., trained algorithms or trained neural networks) or may be identified by a human and input by the human using a user input device (e.g., keyboard, touchscreen graphical user interface, computer mouse, trackpad, etc.).

The neuromodulation may include denervation or neurostimulation. The neuromodulation may include denervation or ablation of a basivertebral nerve, other intraosseous nerve, or a peripheral nerve.

In some embodiments, an unfavorable response would exclude subjects from certain treatment protocols (e.g., basivertebral nerve ablation procedure, discectomy, spinal fusion, facet denervation, peripheral neuromodulation). In some embodiments, a favorable response would qualify subjects for certain treatment protocols.

The method may further include categorizing multiple subjects based on objective scores calculated for the subjects. The categorizing could include identifying subjects likely to have a successful outcome from a particular treatment procedure and those subject likely not to have a successful outcome based on the objective scores. Subject-specific data (e.g., age, lifestyle factors, pain scores, images) could be used to facilitate the categorizing of subjects and to facilitate recommendation of any treatment protocols. The method may also include recommending treatment protocols based on the objective score. The method may further include treating the particular subject (e.g., if the calculated objective score is over a predetermined threshold).

At least a portion of any of the methods described above or elsewhere herein may be wherein at least a portion of the method is performed by application of artificial intelligence technology and techniques (e.g., trained machine learning or deep learning algorithms).

In accordance with several embodiments, a method of training a neural network to be used in determining whether or not a particular subject is a likely candidate for a basivertebral nerve ablation procedure is provided.

The method may include pre-processing a plurality of MRI images of at least a portion of a spine of a plurality of patients in order to make the MRI images more uniform for training. The method may also include identifying indicators of back pain that is likely to be successfully treated by the basivertebral nerve ablation procedure in at least some of the plurality of MRI images. The method may also include identifying images of the plurality of MRI images for which the patients were successfully treated by the basivertebral nerve ablation procedure. In some embodiments, the method may include comparing images prior to and after the basivertebral nerve ablation procedure treatment.

In accordance with several embodiments, a system for quantitatively predicting likelihood that a particular subject would respond favorably to basivertebral nerve ablation to treat chronic low back pain includes a server or computing system comprising one or more hardware processors configured to, upon execution of instructions stored on a non-transitory computer-readable storage medium: receive one or more images (e.g., MRIs) of at least a portion (e.g., lumbosacral region) of a spine of the particular subject, apply pre-processing imaging techniques to the one or more images in order to provide uniformity of the one or more images for feature detection, detect features from the one or more images to identify a plurality of indicators of back pain (e.g., chronic low back pain), quantify the identified plurality of indicators based on an extent of the plurality of indicators, and determine an objective score indicative of a likelihood that the particular subject would respond favorably to a basivertebral nerve ablation procedure based on the quantification of the plurality of indicators. The plurality of indicators may include, for example, bone marrow intensity changes and/or vertebral endplate defects or characteristics of vertebral endplate degeneration. The extent of the plurality of indicators may comprise a quantity, a severity, and/or a spatial assessment of the indicators.

In some embodiments, the one or more hardware processors are further configured to detect features from the one or more images (e.g., MRIs) to identify the plurality of indicators of back pain (e.g., chronic low back pain) by applying a trained neural network to the one or more images to automatically identify the plurality of indicators of back pain and/or to determine the objective score based on the identified plurality of indicators.

In some embodiments, the system includes an imaging scanner or system (such as an MRI scanner) from which the images can be retrieved and stored.

A non-transitory physical computer storage medium comprising computer-executable instructions stored thereon that, when executed by one or more processors, may be configured to implement a process including receiving one or more images (e.g., MRIs) of at least a portion of a spine of the particular subject, applying pre-processing imaging techniques to the one or more images, extracting features from the one or more images to identify a plurality of indicators of back pain (e.g., chronic low back pain), and determining an objective score indicative of a likelihood that the particular subject would respond favorably to basivertebral nerve ablation based on said extracting. The plurality of indicators include at least one of: (i) bone marrow intensity changes and (ii) vertebral endplate defects or characteristics of vertebral endplate degeneration.

The process may further include quantifying the identified plurality of indicators of back pain. Quantifying the identified plurality of indicators may include one or more of: determining a quantity of the bone marrow intensity changes and/or vertebral endplate defects, determining a level of extent of the bone marrow intensity changes and/or vertebral endplate defects, and quantifying identified fat fraction changes.

In some embodiments, extracting features comprises applying a trained neural network to the one or more images to automatically identify the plurality of indicators of back pain. In some embodiments, determining the objective score comprises applying a trained neural network to the one or more images to automatically calculate the objective score based on the extracting of features.

In accordance with several embodiments, a method of detecting and treating back pain of a subject includes identifying a candidate vertebral body for treatment based on a determination that the vertebral body exhibits one or more symptoms or defects associated with vertebral endplate degeneration and ablating a basivertebral nerve within the identified candidate vertebral body by applying a thermal treatment dose to a location within the vertebral body of at least 240 cumulative equivalent minutes ("CEM") using a CEM at 43 degrees Celsius model or a comparable thermal treatment dose using another model, such as an Arrhenius model. The one or more symptoms associated with vertebral endplate degeneration or defects include pre-Modic change characteristics.

In some embodiments, the determination is based on images of the candidate vertebral body (e.g., MRI images, CT images, X-ray images, fluoroscopic images, ultrasound images). In some embodiments, the determination is based on obtaining biomarkers from the subject. The biomarkers may be obtained, for example, from one or more blood serum samples (e.g., blood plasma). The biomarkers may be obtained over an extended period of time (e.g., a period of days, weeks, or months) or at a single instance in time.

In accordance with several implementations, target, or candidate, vertebrae for treatment can be identified prior to treatment. The target, or candidate, vertebrae may be identified based on identification of various types of, or factors associated with, endplate degeneration and/or defects (e.g., focal defects, erosive defects, rim defects, corner defects, all of which may be considered pre-Modic change characteristics). For example, one or more imaging modalities (e.g., MRI, CT, X-ray, fluoroscopic imaging) may be used to determine whether a vertebral body or vertebral endplate exhibits active Modic characteristics or "pre-Modic change" characteristics (e.g., characteristics likely to result in Modic changes, such as Type 1 Modic changes that include findings of inflammation and edema or type 2 Modic changes that include changes in bone marrow (e.g., fibrosis) and increased visceral fat content). For example, images obtained via MRI (e.g., IDEAL MRI) may be used to identify (e.g., via application of one or more filters) initial indications or precursors of edema or inflammation at a vertebral endplate prior to a formal characterization or diagnosis as a Type 1 Modic change. Examples of pre-Modic change characteristics could include mechanical characteristics (e.g., loss of soft nuclear material in an adjacent intervertebral disc of the vertebral body, reduced disc height, reduced hydrostatic pressure, microfractures, focal endplate defects, erosive endplate defects, rim endplate defects, corner endplate defects, osteitis, spondylodiscitis, Schmorl's nodes) or bacterial characteristics (e.g., detection of bacteria that have entered an intervertebral disc adjacent to a vertebral body, a disc herniation or annulus tear which may have allowed bacteria to enter the intervertebral disc, inflammation or new capilarisation that may be caused by bacteria) or other pathogenetic mechanisms that provide initial indications or precursors of potential Modic changes or vertebral endplate degeneration or defects.

Accordingly, vertebral bodies may be identified as target candidates for treatment before Modic changes occur (or before painful symptoms manifest themselves to the patient) so that the patients can be proactively treated to prevent, or reduce the likelihood of, chronic low back pain before it occurs. In this manner, the patients will not have to suffer from debilitating lower back pain for a period of time prior to treatment. Modic changes may or may not be correlated with endplate defects and may or may not be used in candidate selection or screening. In accordance with several embodiments, Modic changes are not evaluated and only vertebral endplate degeneration and/or defects (e.g., pre-Modic change characteristics prior to onset or prior to the ability to identify Modic changes) are identified. Rostral and/or caudal endplates may be evaluated for pre-Modic changes (e.g., endplate defects that manifest before Modic changes that may affect subchondral and vertebral bone marrow adjacent to a vertebral body endplate).

In some implementations, a level of biomarker(s) (e.g., substance P, cytokines, high-sensitivity C-reactive protein, or other compounds associated with inflammatory processes and/or pain and/or that correlate with pathophysiological processes associated with vertebral endplate degeneration or defects (e.g., pre-Modic changes) or Modic changes such as disc resorption, Type III and Type IV collagen degradation and formation, or bone marrow fibrosis) may be obtained from a patient (e.g., through a blood draw (e.g., blood serum) or through a sample of cerebrospinal fluid) to determine whether the patient is a candidate for basivertebral nerve ablation treatment (e.g., whether they have one or more candidate vertebral bodies exhibiting factors or symptoms associated with endplate degeneration or defects (e.g., pre-Modic change characteristics)). Cytokine biomarker samples (e.g., pro-angiogenic serum cytokines such as vascular endothelial growth factor (VEGF)-C, VEGF-D, tyrosine-protein kinase receptor 2, VEGF receptor 1, intercellular adhesion molecule 1, vascular cell adhesion molecule 1) may be obtained from multiple different discs or vertebral bodies or foramina of the patient and compared with each other in order to determine the vertebral bodies to target for treatment. Other biomarkers may be assessed as well, such as neo-epitopes of type III and type IV pro-collagen (e.g., PRO-C3, PRO-C4) and type III and type IV collagen degradation neo-epitopes (e.g., C3M, C4M).

In some implementations, samples are obtained over a period of time and compared to determine changes in levels over time. For example, biomarkers may be measured weekly, bi-monthly, monthly, every 3 months, or every 6 months for a period of time and compared to analyze trends or changes over time. If significant changes are noted between the biomarker levels (e.g., changes indicative of endplate degeneration or defects (e.g., pre-Modic change characteristics) or Modic changes, as described above), treatment may be recommended and performed to prevent or treat back pain. Biomarker levels (e.g., substance P, cytokine protein levels, PRO-C3, PRO-C4, C3M, C4M levels) may be measured using various in vivo or in vitro kits, systems, and techniques (e.g., radio-immunoassay kits/methods, enzyme-linked immunosorbent assay kits, immunohisto-chemistry techniques, array-based systems, bioassay kits, in vivo injection of an anticytokine immunoglobulin, multi-plexed fluorescent microsphere immune-assays, homogeneous time-resolved fluorescence assays, bead-based techniques, interferometers, flow cytometry, etc.). Cytokine proteins may be measured directly or indirectly, such as by measuring mRNA transcripts.

The identification of pre-Modic change characteristics may involve determining a quantitative or qualitative endplate score based on severity, extent, and/or quantity of the identified pre-Modic change characteristics (e.g., vertebral endplate defects) and vertebrae having a quantitative endplate score above a threshold may be deemed as potential candidates for treatment (e.g., basivertebral nerve ablation). The pre-Modic change characteristics may be combined with age, gender, body mass index, bone mineral density measurements, back pain history, and/or other known risk factors for vertebral endplate degeneration or defects (such as smoking, occupational or recreational physical demands or situations) in identifying candidate patients and/or candidate vertebral bodies for treatment (e.g., basivertebral nerve ablation).

In accordance with several embodiments, a method of detecting and treating back pain of a subject includes obtaining images of a vertebral body of the subject and analyzing the images to determine whether the vertebral body exhibits one or more symptoms associated with a pre-Modic change. The method also includes modulating (e.g., ablating, denervating, stimulating) an intraosseous nerve (e.g., basivertebral nerve) within the vertebral body if it is determined that the vertebral body exhibits one or more symptoms associated with a pre-Modic change.

The images may be obtained, for example, using an MRI imaging modality, a CT imaging modality, an X-ray imaging modality, an ultrasound imaging modality, or fluoroscopy. The one or more symptoms associated with a pre-Modic change may comprise characteristics likely to result in Modic changes (e.g., Type 1 Modic changes, Type 2 Modic changes). The one or more symptoms associated with a pre-Modic change may comprise initial indications or precursors of edema or inflammation at a vertebral endplate prior to a formal characterization or diagnosis as a Modic change. The one or more symptoms may include edema, inflammation, and/or tissue change within the vertebral body or along a portion of a vertebral endplate of the vertebral body. Tissue changes may include tissue lesions or changes in tissue type or characteristics of an endplate of the vertebral body and/or tissue lesions or changes in tissue type or characteristics of bone marrow of the vertebral body. The one or more symptoms may include focal defects, erosive defects, rim defects, and corner defects of a vertebral endplate of the vertebral body.

Spinal treatment procedures may include modulation of nerves within or surrounding bones of the spine (e.g., vertebral bodies). The terms "modulation" or "neuromodulation", as used herein, shall be given their ordinary meaning and shall also include ablation, permanent denervation, temporary denervation, disruption, blocking, inhibition, electroporation, therapeutic stimulation, diagnostic stimulation, inhibition, necrosis, desensitization, or other effect on tissue. Neuromodulation shall refer to modulation of a nerve (structurally and/or functionally) and/or neurotransmission. Modulation is not necessarily limited to nerves and may include effects on other tissue, such as tumors or other soft tissue.

The particular spinal neuromodulation procedure to be performed may include denervating (e.g., ablating) the basivertebral nerve within the vertebral body may include applying energy (e.g., radiofrequency energy, ultrasound energy, microwave energy) to a target treatment region within the vertebral body sufficient to denervate (e.g., ablate, electroporate, molecularly dissociate, necrose) the basivertebral nerve using a radiofrequency energy delivery device. The denervating may alternatively or additionally include applying an ablative fluid (e.g., steam, chemical, cryoablative fluid) to a target treatment region within the vertebral body.

Any of the method steps described herein may be performed by one or more hardware processors (e.g., of a server) by executing program instructions stored on a non-transitory computer-readable medium.

Several embodiments of the invention have one or more of the following advantages: (i) increased treatment accuracy; (ii) increased efficacy results; (iii) increased efficiency; (iv) increased patient satisfaction; (v) increased number of people receiving the particular back pain treatment procedure that would not have been previously identified; and/or (vi) reduction in patients treated in which the particular back pain treatment procedure would not be successful due to the back pain originating from other sources.

For purposes of summarizing the disclosure, certain aspects, advantages, and novel features of embodiments of the disclosure have been described herein. It is to be understood that not necessarily all such advantages may be achieved in accordance with any particular embodiment of the disclosure provided herein. Thus, the embodiments disclosed herein may be embodied or carried out in a manner that achieves or optimizes one advantage or group of advantages as taught or suggested herein without necessarily achieving other advantages as may be taught or suggested herein.

The methods summarized above and set forth in further detail below describe certain actions taken by a practitioner; however, it should be understood that they can also include the instruction of those actions by another party. Thus, actions such as, for example, "applying thermal energy" include "instructing the applying of thermal energy." Further aspects of embodiments of the disclosure will be discussed in the following portions of the specification. With respect to the drawings, elements from one figure may be combined with elements from the other figures.

BRIEF DESCRIPTION OF THE DRAWINGS

Several embodiments of the disclosure will be more fully understood by reference to the following drawings which are for illustrative purposes only.

DETAILED DESCRIPTION

Introduction

Figure 1:
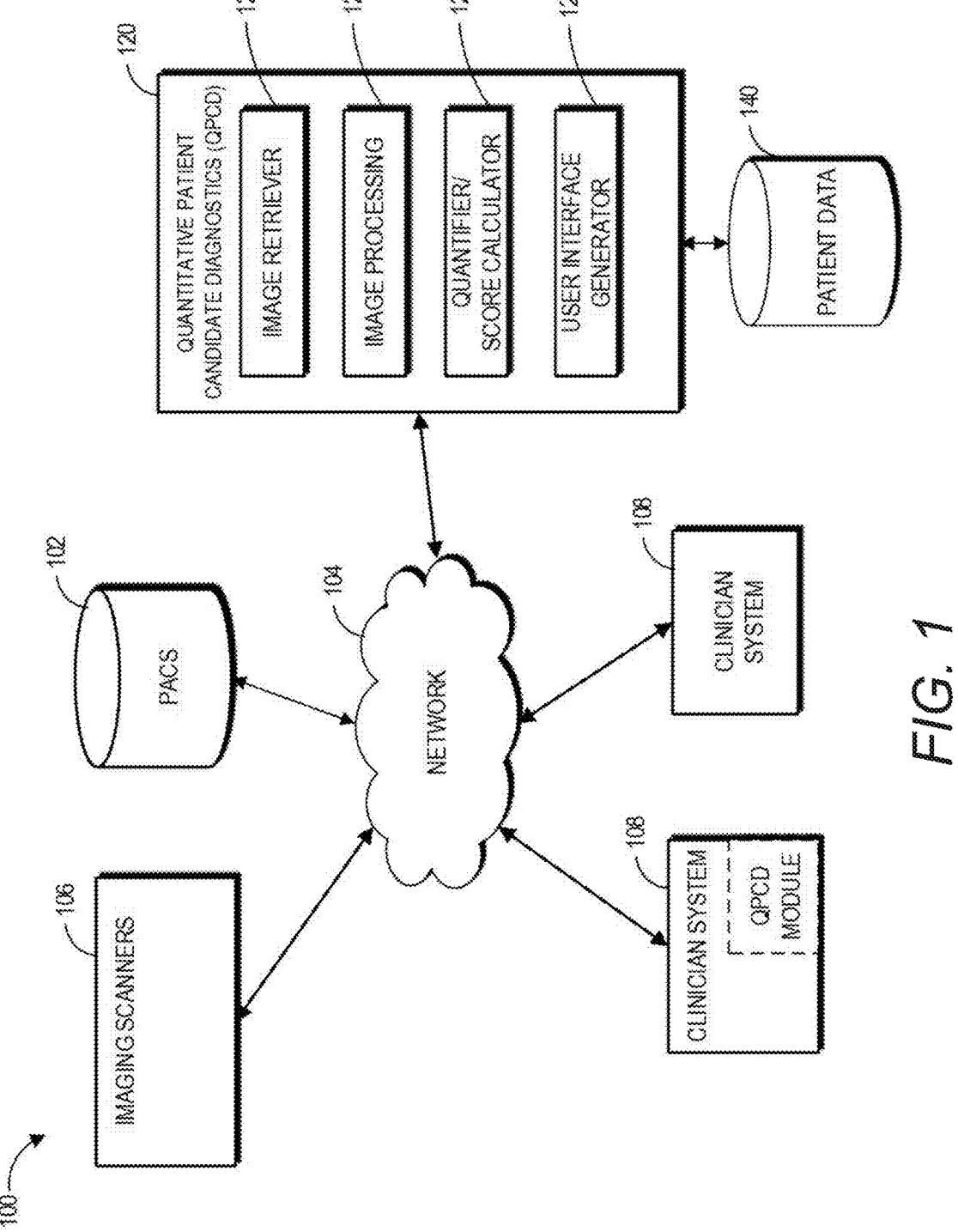
FIG. 1 illustrates an embodiment of a computing environment including a quantitative patient candidate diagnostics (QPCD) system that can enable clinicians to quantitatively analyze patient candidates for a basivertebral nerve ablation procedure.

Back pain (e.g., chronic low back pain) may be caused by many sources, including vertebral endplate defects or degeneration, bone marrow intensity changes such as Modic changes, ligament sprains, facet joint pain, muscle strain, muscle atrophy, spinal tendon injury, spinal nerve compression, herniated discs, slipped discs, degenerative disc disease, sacroiliac joint dysfunction, bacterial or fungal infection, vertebral fractures, osteoporosis, and/or spinal tumors. It can be difficult for clinicians to identify an exact source of the back pain with confidence and reliable accuracy simply by visually inspecting images obtained from one or more imaging modalities and/or by reviewing subjective patient pain scores (e.g., Oswestry Disability Index ("ODI") scores or Visual Analog Score ("VAS") pain scores, quality of life measures, patient reported outcome measures). As a result, sometimes patients with back pain (e.g., chronic low back pain) are treated using a particular procedure that does not successfully reduce the back pain of the patient because the particular procedure does not effectively treat the actual source of the back pain, or does not treat all the actual sources of the back pain.

For example, the particular back pain treatment procedure may be a basivertebral nerve ablation procedure designed to treat back pain (e.g., chronic low back pain) originating from one or more vertebral bodies or vertebral endplates and the actual source of pain may be, or also include, discogenic pain originating from one or more intervertebral discs that may not be effectively treated by the basivertebral nerve ablation procedure. As another example, patients may receive a back pain treatment procedure intended to treat discogenic pain or pain originating from sources other than from one or more vertebral bodies or vertebral endplates when the actual source of pain originates from one or more vertebral bodies or vertebral endplates. Accordingly, clinicians may perform procedures that are not effective, or not successful, and patients may experience ongoing pain and reduced satisfaction that may result in poor feedback or patient reviews for the particular clinician or hospital or treatment center or company providing the technology used for the procedure.

In accordance with several embodiments, systems and methods disclosed herein provide a more reliable prediction of a particular source or type of back pain (e.g., chronic low back pain) that may be effectively treated by a particular back pain treatment procedure (e.g., basivertebral nerve ablation procedure). The systems and methods disclosed herein may also advantageously provide an increase in the number of patients identified as likely candidates for the particular back pain treatment procedure (e.g., basivertebral nerve ablation procedure) that may not have been identified previously based on image visualization by clinicians or subjective or qualitative factors or input from patients. The prediction may involve generation (e.g., fully or partially-automated automated calculation) of an objective or quantitative score, value, or other output based on a combination (e.g., weighted combination) of indicators of the particular source of the type of back pain that may be effectively treated by a particular back pain treatment procedure (e.g., basivertebral nerve ablation procedure). Basing the prediction on multiple indicators may provide enhanced accuracy, reliability and confidence and reduce false positives and false negatives. In addition, the percentage of successful treatments for the particular back pain treatment procedure (e.g., basivertebral nerve ablation procedure) may advantageously be increased, resulting in increased patient satisfaction and reduced costs. The systems and methods disclosed herein may also enable clinicians to tailor or adjust parameters (e.g., positioning, duration, targets) of the particular back pain treatment procedure (e.g., basivertebral nerve ablation procedure) to more effectively treat the actual source of the back pain (e.g., chronic low back pain).

Example QPCD System

FIG. 1 illustrates an embodiment of a computing environment 100 for providing clinicians with access to a QPCD system 120 to determine patient candidates likely to have pain stemming from one or more vertebral bodies or vertebral endplates and thus likely to respond favorably to a spinal neuromodulation procedure (e.g., basivertebral nerve ablation procedure, such as the Intracept® basivertebral nerve ablation procedure provided commercially by Relievant Medsystems, Inc.) that targets that particular source of back pain (e.g., chronic low back pain). In an embodiment, the QPCD system 120 determines a quantitative assessment (e.g., score, value, or other output) of a patient's likelihood of responding favorably to the spinal neuromodulation procedure (e.g., basivertebral nerve ablation procedure) based, at least in part, on analyzing a plurality of indicators identified from images of at least a portion of the patient's spine obtained using one or more imaging modalities (e.g., MRI, CT, SPECT, X-ray, etc.). The computing environment 100 can include clinician systems 108 that can access the QPCD system 120, which may include one or more modules to determine the patient's likelihood of back pain originating from a particular source (e.g., one or more vertebral end-plates or vertebral bodies) and thus likelihood of the patient responding favorably to a particular spinal neuromodulation procedure (e.g., basivertebral nerve ablation procedure).

The QPCD system 120 can include an image retriever module 122 that can retrieve images corresponding to scans of at least a portion of a spine (e.g. lumbar region, sacral region, thoracic region, cervical region, or combinations of two or more of these spinal regions) of a particular patient or multiple subjects. In an embodiment, the image retriever 122 can receive raw images directly from an imaging scanner 106 (e.g., MRI scanner). In other embodiments, the image retriever 122 can receive images from a PACS (Picture Archiving and Communication System) repository 102. The image retriever module 122 can also receive images from a storage medium such as a compact disc (CD), a portable hard drive, cloud storage, servers, or other storage database or storage medium, etc. The PACS repository 102 may store images, for example, in a DICOM (Digital Imaging and Communication in Medicine) format. The PACS repository 102 may also include other non-image data regarding patients (e.g., age, gender, body mass index, bone mineral density measurements, pain scores, quality of life measures, patient-reported outcomes, whether the patients received spinal neuromodulation therapy or not, and whether or not the therapy was successful). The image retriever module 122 can also receive images of different formats (e.g. jpeg, png, pdf, bmp, CT scanner raw files, MRI raw files, PET raw files, x-ray raw files, etc.). In an embodiment, the image retriever module 122 retrieves images from the PACS repository 102 or imaging scanners wirelessly over a network 104. In another embodiment, the image retriever module 122 retrieves images through a local wired or integrated connection. The image retriever module 122 may receive the images from the PACS repository 102 in response to an input from the clinician system 108.

Figure 5:
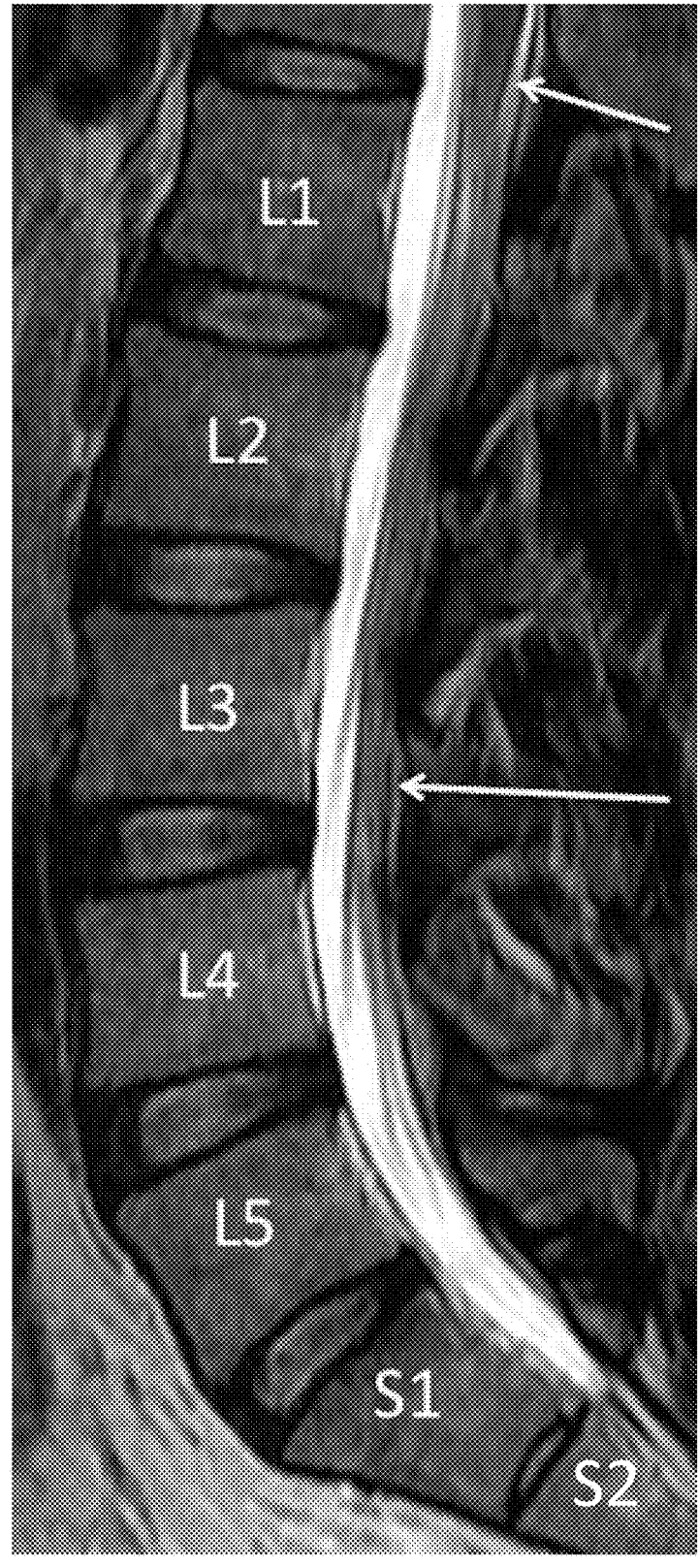
FIGS. 5, 6A-6D and 7 illustrate examples of pre-processing and/or feature extraction steps to facilitate identification and quantitative assessment of a plurality of indicators of back pain.

The QPCD system 120 can include an image processing module 124 to perform pre-processing and/or analysis (e.g., feature extraction, or detection) of the images retrieved by the image retriever module 122. The image processing module 124 can process the images and identify one or more indicators of back pain stemming from one or more vertebral bodies or vertebral endplates from the images as described in more detail below. The indicators can include one or more of bone marrow intensity changes, vertebral endplate defects or degeneration, paraspinal muscle tissue characteristics (e.g., multifidus muscle atrophy), bone turnover, interverte-bral disc calcification indicators, etc. The image processing module 124 can pre-process received images (e.g., by performing rotation, sizing changes, contrast changes, image quality enhancement, or other image processing and clean-up techniques) to prepare the images for feature extraction, or feature detection to identify the indicators. The image processing module 124 can also perform feature extraction, or feature detection, to identify the one or more indicators of back pain arising from one or more vertebral bodies or vertebral endplates from the images. The feature extraction may include an identification (e.g., alphanumeric text label) of each vertebral level shown in the image (such as shown in FIG. 5). The image processing module 124 may use information obtained from one image to process another image for the same patient or future patients. The image processing module 124 may incorporate previously-trained neural networks to perform pre-processing and/or feature extraction on the images.

The QPCD system 120 may also include a quantifier/score calculator module 126 to quantify the plurality of indicators identified by the image processing module 124 and to generate an objective or quantitative score, value, or other output indicative of likelihood that the patient would favorably respond to a particular spinal neuromodulation procedure (e.g., basivertebral nerve ablation procedure) that targets a source of back pain correlated with the plurality of indicators based on the objective or quantitative score, value, or other output. In some embodiments, the quantifier/score calculator module 126 may generate a binary output indicating a Yes or No output or recommendation to proceed with the particular spinal neuromodulation procedure (e.g., basivertebral nerve ablation procedure) based on the objective or quantitative score or other value. The quantifier/score calculator module 126 may also include post-processing checks intended to provide increased confidence in the score or value, or in the binary Yes/No output (e.g., to reduce false positives or false negatives). For example, the objective or quantitative score, value, or other output may be based on analysis of a combination (e.g., weighted combination) of one or more indicators (e.g., first-tier indicators such as bone marrow intensity changes and/or vertebral endplate defects or degeneration) and the post-processing checks may be based on analysis of one or more additional indicators (e.g., second-tier indicators such as paraspinal muscle character-istics, bone turnover determined from SPECT imaging). The quantitative scores or other values and/or the binary output can be stored in the patient data repository 140 or in the PACS repository 102 along with other data for the patient. The scores or other quantitative values and/or the binary output can also be transmitted over a wired or wireless network to a clinician system 108. The quantifier/score calculator module 126 may also apply previously-trained algorithms or neural networks.

The image processing module 124 may store analyzed images in a patient data repository 140 or transmit it back to the PACS repository 102. In some embodiments, the image processing module 124 may include internal checks to ensure that the images correspond to a spine or portion of a spine. The user interface module 128 can interact with one or more other modules of the QPCD system 120 to generate one or more graphical user interfaces. In some embodi-ments, the graphical user interfaces can be one or more web pages or electronic documents. The user interface module 128 can also receive data such as patient information from the clinician system(s) 108. In some instances, the user interface module 128 may receive commands from the clinician system(s) 108 to initiate one or more functionalities of the QPCD system 120.

The QPCD system 120 can be implemented in computer hardware and/or software. The QPCD system 120 can execute on one or more computing devices, such as one or more physical server computers. In implementations where the QPCD system 120 is implemented on multiple servers, these servers can be co-located or can be geographically separate (such as in separate data centers). In addition, the QPCD system 120 can be implemented in one or more virtual machines that execute on a physical server or group of servers. Further, the QPCD system 120 can be hosted in a cloud computing environment, such as in the Amazon Web Services (AWS) Elastic Compute Cloud (EC2) or the Microsoft® Windows® Azure Platform. The QPCD system 120 can also be integrated with scanners 106 through software or hardware plug-in or an API (application pro-gramming interface). In some embodiments, the clinician systems 108 may implement some or all of the modules of the QPCD system 120. For instance, the clinician systems 108 may implement the user interface generator module

128, while the rest of the modules are implemented remotely on a server. In other embodiments, a plugin to the QPCD system 120 may be installed on a third party tool. The QPCD system 200 can include multiple engines or modules for performing the processes and functions described herein, such as the modules described above. The engines or modules can include programmed instructions for performing processes as discussed herein. The programming instructions can be stored in a memory. The programming instructions can be implemented in C, C++, JAVA, or any other suitable programming languages. In some embodiments, some or all of the portions of the QPCD system 120 including the engines or modules can be implemented in application specific circuitry such as ASICs and FPGAs. While shown as separate engines or modules, the functionality of the engines or modules as discussed herein is not necessarily required to be separated.

The clinician systems 108 can remotely access the QPCD system 120 on these servers through the network 104. The clinician systems 108 can include thick or thin client software that can access the QPCD system 120 on the one or more servers through the network 104. The network may be a local area network (LAN), a wide area network (WAN), such as the Internet, combinations of the same, or the like. For example, the network 104 can include a hospital or other institution's private intranet, the public Internet, or a combination of the same. In some embodiments, the user software on the clinician system 108 can be a browser software or other application software. The clinician system 108 can access the QPCD system 120 through the browser software or other application software.

In general, the clinician systems 108 can include any type of computing device capable of executing one or more applications and/or accessing network resources. For example, the clinician systems 108 can be desktops, laptops, netbooks, tablet computers, smartphones, smartwatches, augmented reality wear, PDAs (personal digital assistants), servers, e-book readers, video game platforms, television set-top boxes (or simply a television with computing capability), a kiosk, combinations of the same, or the like. The clinician systems 108 include software and/or hardware for accessing the QPCD system 120, such as a browser or other client software.

Example Quantitative Prediction Processes

Figure 2:
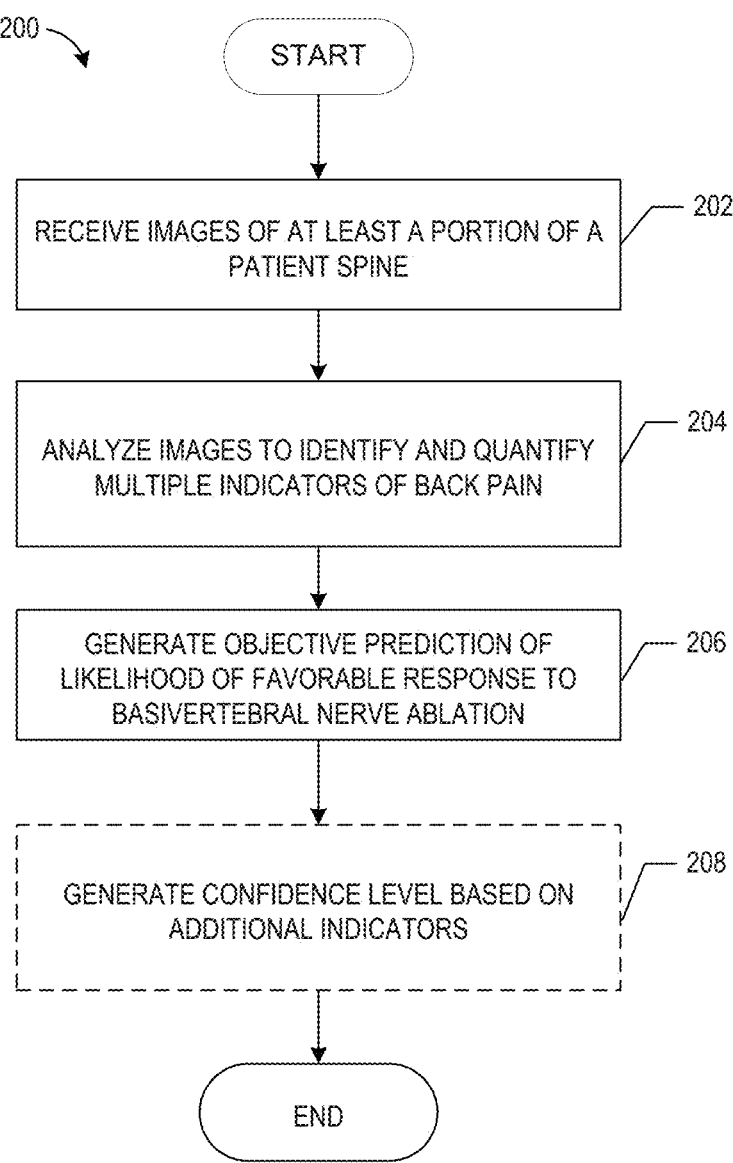
FIGS. 2-4 illustrate embodiments of a process for generating an objective or quantitative prediction of likelihood that a patient candidate will respond favorably to a basivertebral nerve ablation procedure or other treatment.

FIG. 2 illustrates an embodiment of a process 200 for generating an objective or quantitative prediction of likelihood that a patient candidate will respond favorably to a particular spinal neuromodulation procedure (e.g., a basivertebral nerve ablation procedure) intended to target a particular source of back pain (e.g., back pain originating from one or more vertebral bodies or vertebral endplates). The objective or quantitative prediction can be a numerical, graphical, or textual indicator (or combination of the same). For example, the objective or quantitative prediction can include a percentage, a score on a scale, a binary Yes or No, and/or a color. The quantitative prediction process 200 can be implemented by the QPCD system 120 described above. For illustrative purposes, the quantitative prediction process 200 will be described as being implemented by components of the computing environment 100 of FIG. 1. The entire process 200 or portions of the process 200 may be automated by execution of stored program instructions stored on a non-transitory computer-readable medium by one or more hardware processors.

The quantitative prediction process 200 beings at block 202 with receiving images of a patient candidate (e.g., from the PACS 102 or from imaging scanners 106). The image retriever module 122 can receive image data corresponding to MRI, CT, SPECT, PET, X-ray or other imaging scans of at least portions of the patient's spine. The MRI image data may include T1-weighted MRI images, T2-weighted MRI images, fat-suppression MRI images, UTE MRI sequenced images, IDEAL MRI sequenced images, fast spin echo MRI images, T1ρ-weighted images, and/or other MRI images obtained using other MRI sequences, pulsing, weighting, or techniques. The received images may include one or more regions of the patient's spine (e.g. lumbar region, sacral region, thoracic region, cervical region, or combinations of two or more of these spinal regions). The images may comprise sequential images over a period of time or images at a single point in time.

At Block 204, the QPCD system 120 can analyze the received images to identify and quantify one indicator or multiple indicators of back pain (e.g., vertebral endplate defects or degeneration, bone marrow intensity changes, paraspinal muscle tissue characteristics (e.g., multifidus muscle atrophy), active bone turnover, intervertebral disc calcification indicators, vertebral fat fraction) in or from the images. The indicators of back pain may be indicators correlated to back pain stemming from one or more vertebral bodies or vertebral endplates and/or from one or more adjacent intervertebral discs. For example, the image processing module 124 can perform image processing technique to automatically identify, or detect, the one or more indicators (e.g., through feature extraction) and the quantifier/score calculator module 126 can analyze (e.g., quantify) the identified one or more indicators. The quantifier/score calculator module 126 can then generate an objective prediction (e.g., quantitative score) of likelihood that the patient has pain stemming from one or more vertebral bodies or vertebral endplates and will respond favorably to a spinal neuromodulation procedure (e.g., basivertebral nerve ablation procedure) at Block 206.

In some embodiments, only indicators of back pain known to correlate with pain stemming from one or more vertebral bodies or vertebral endplates are identified and assessed and indicators of discogenic back pain (pain originating from the intervertebral disc) or other pain sources are not identified or assessed. The indicators may be identified or determined and/or objective scores may be generated or calculated by application of trained algorithms or trained neural networks.

The QPCD system 120 may optionally generate a confidence level or perform an additional verification step at Block 208 to reduce false positives or negatives in the objective prediction (e.g., quantitative score or binary YES/NO output). The verification or confidence level generation step may involve identification and/or quantification of one or more additional indicators (e.g., indicators known to have a strong correlation or sensitivity with) of a particular source of back pain (e.g., chronic low back pain stemming from one or more vertebral bodies or vertebral endplates) not used in the previous steps. For example, the multiple indicators identified and quantified in the previous steps may include vertebral endplate defects or degeneration and/or bone marrow intensity changes, whereas the one or more indicators used in the verification or confidence level generation step at Block 208 may include paraspinal muscle tissue characteristics (e.g., multifidus muscle characteristics), active bone turnover, intervertebral disc calcification, or other indicators.

In some embodiments, the indicators used at Blocks 204 and 206 may be considered first-tier or more reliable/accurate indicators of the particular source of back pain and the indicators used at Block 208 may be considered second-tier indicators correlated to the particular source of back pain. In other embodiments, the indicators used to determine the quantitative score or other output may be more well accepted at the time by clinicians as correlating to the particular source of back pain (e.g., chronic low back pain originating from one or more vertebral bodies or vertebral endplates). The indicators identified and quantified at Block 208 may be identified based on the same images as in Blocks 204 and 206 or based on different images (e.g., SPECT images, CT images, different MRI images). In an embodiment, the images used at Blocks 204 and 206 are only MRI images but may constitute different types of MRI images (e.g., T1-weighted images, T2-weighted images, fat-suppressed images, UTE images, IDEAL images). In some embodiments, the first-tier and second-tier indicators are both used to determine the quantitative score or other output.

Figure 3:
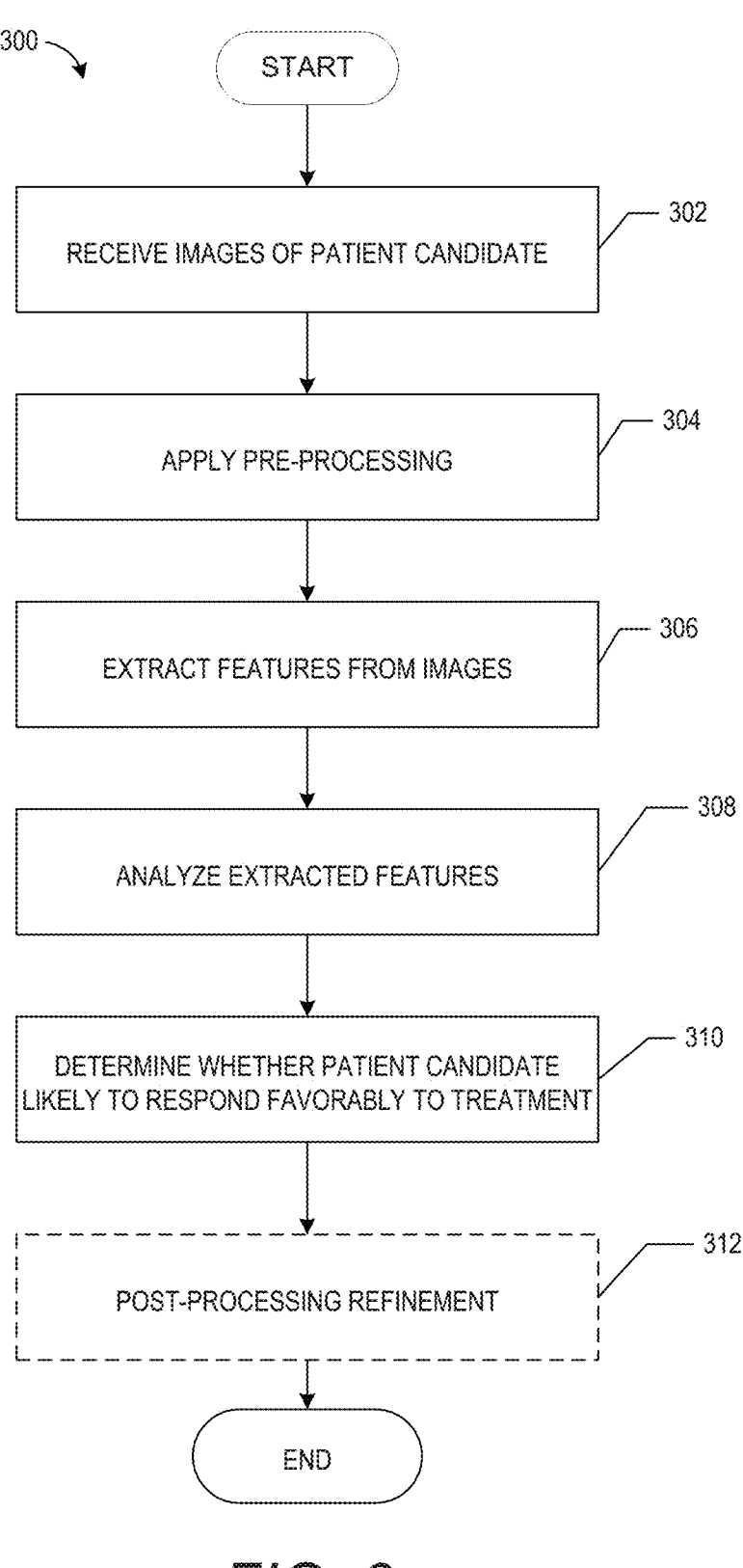

FIG. 3 illustrates another embodiment of a process 300 for generating an objective or quantitative prediction of likelihood that a patient candidate will respond favorably to a spinal neuromodulation procedure (e.g., a basivertebral nerve ablation procedure). As with quantitative prediction process 200, the quantitative prediction process 300 can be implemented by the QPCD system 120 described above. For illustrative purposes, the quantitative prediction process 300 will be described as being implemented by components of the computing environment 100 of FIG. 1. The entire process 300 or portions of the process 300 may be automated by execution of stored program instructions stored on a non-transitory computer-readable medium by one or more hardware processors. Any of the steps of the process 300 may include application of trained algorithms or trained neural networks.

At Block 302, the QPCD system 120 (e.g., image retriever module 122) receives images of a patient candidate for a spinal neuromodulation procedure (e.g., basivertebral nerve ablation procedure). The images may correspond to MRI, CT, SPECT, PET, X-ray or other imaging scans of the patient's spine. The MRI images may include T1-weighted MRI images, T2-weighted MRI images, fat-suppressed MRI images, UTE MRI images, and/or IDEAL MRI images. The received images may include one or more regions of the patient's spine (e.g. lumbar region, sacral region, thoracic region, cervical region, or combinations of two or more of these spinal regions). The images may comprise sequential images over a period of time or images at a single point in time.

At Block 304, the image processing module 124 may apply pre-processing to the images. The pre-processing may involve analog or digital image processing techniques. The pre-processing may include rotating, cropping, enlarging, reducing, removing noise, segmenting, smoothing, contrast or color enhancing, and/or other image processing techniques. The pre-processing may also include spatial orientation identification, vertebral level identification, general anatomical feature identification, and/or the like. In some embodiments, the pre-processing may be performed by running the images through a previously-trained neural network trained to clean up, enhance, reconstruct, or otherwise improve the quality of images, such as noisy MRI images.

At Block 306, the image processing module 124 may perform feature extraction on the pre-processed images. Feature extraction may include spatial orientation identification, vertebral level identification, general anatomical feature identification, and/or the like if not performed in the pre-processing. Feature extraction may also include identification of indicators of back pain in the images (e.g., vertebral endplate defects or degeneration, bone marrow intensity changes, paraspinal muscle tissue characteristics (e.g., multifidus muscle atrophy), bone turnover, vertebral bone marrow fat fraction, intervertebral disc calcification, etc.).

The QPCD system 120 may then analyze the extracted features at Block 308. The analysis may include applying one or more rules to the extracted features to assess (e.g., quantify) identified indicators of back pain and the likelihood that the patient with the identified indicators would respond favorably to a particular spinal neuromodulation procedure (e.g., basivertebral nerve ablation procedure).

The analysis of vertebral endplate defects or degeneration may include spatial and quantification analyses. The spatial analysis may include, for example, identification of the location(s) or position(s) along the vertebral endplate where the defects or degeneration occur. The analysis of vertebral endplate defects or degeneration may include, for example, identifying various subclassifications of defects (e.g., focal defects, erosive defects, rim defects, corner defects), identifying defects to a normal continuous lining of a vertebral endplate, identifying irregularities in the endplate lining, assessing an amount, or quantity, of defects, assessing an extent or severity of the defects (e.g., width, depth, total area or volume, percentage of whole), evaluating contour profiles of vertebral endplates (e.g., jaggedness, depth), identifying the defects as being a particular phenotype subtype of vertebral endplate defect. Contour profiles may be developed, for example, through hypo- and hyper-signal identification on T1-weighted or T2-weighted images.

The analysis of bone marrow intensity changes may include a classification of the changes as Type 1 or Type 2 Modic changes based on conventional Modic change classification schemes. The analysis of bone marrow intensity changes may also include a spatial and/or extent or severity of change analysis. For example, the analysis may identify locations where the bone marrow intensity changes occur within a vertebral body and/or an extent (height, volume, position) of the bone marrow intensity changes. Annular-nuclear border bone marrow intensity changes may be more significant than bone marrow intensity changes in a center of a vertebral body, for example, or vice-versa. In some embodiments, the Modic changes may be classified using T1-weighted, T2-weighted, or fat-suppression MRI images. For example, Type 1 Modic changes may be identified as white swelling or inflammation on T2-weighted MRI images and less bright spots on T1-weighted MRI images. Type 2 Modic changes may be identified as light spots on both T1- and T2-weighted MRI images. In some embodiments, the analysis of bone marrow intensity changes may incorporate use of UTE MRI sequences or IDEAL sequences.

In some embodiments, the analysis of bone marrow intensity changes may include assessment of vertebral fat fraction. Vertebral fat fraction (e.g. conversion of water to fat in bone marrow) may comprise analysis of IDEAL MRI images. Bone marrow intensity changes may be identified in both the vertebral body and in one or more adjacent vertebral endplates. Bone marrow intensity changes may include, for example, bone marrow edema, bone marrow inflammation, bone marrow lesions, and/or conversion of normal red haemopoietic bone marrow into yellow fatty marrow, which can be identified from the received images.

Bone marrow intensity changes may also comprise pre-Modic change characteristics that provide initial indications or precursors of edema or inflammation at a vertebral endplate prior to a formal characterization or diagnosis as a Type 1 Modic change. Examples of pre-Modic change characteristics could include mechanical characteristics (e.g., loss of soft nuclear material in an adjacent intervertebral disc of the vertebral body, reduced disc height, reduced hydrostatic pressure, microfractures, fissures, spondylodiscitis, Schmorl's nodes, osteitis) or bacterial characteristics (e.g., detection of bacteria that have entered an intervertebral disc adjacent to a vertebral body, a disc herniation or annulus tear which may have allowed bacteria to enter the intervertebral disc, inflammation or new capilarisation that may be caused by bacteria) or other pathogenetic mechanisms that provide initial indications or precursors of potential Modic changes. Rostral and/or caudal endplates may be evaluated for pre-Modic changes (e.g., endplate defects that manifest before Modic changes that may affect subchondral and vertebral bone marrow adjacent to a vertebral body endplate).

After the analysis of extracted features at Block 308, the QPCD system 120 (e.g., quantifier/score calculator module 126) may generate an objective prediction (e.g., quantitative score or other output) of likelihood that the patient will respond favorably to a spinal neuromodulation procedure (e.g., basivertebral nerve ablation procedure) based on the analysis of the extracted features, similar as described in connection with Block 206 of quantitative prediction process 200. The output generated may be a binary YES or NO output as to whether the patient is likely to respond favorably to the spinal neuromodulation procedure (e.g., basivertebral nerve ablation procedure). The output may be based on analysis of a combination (e.g., weighted combination) of two, three, four, or more than four indicators, which may include only first-tier indicators or both first-tier indicators and second-tier indicators.

The quantitative prediction process 300 may optionally include post-processing refinement at Block 312. The post-processing refinement may function, for example, as a check to reduce false positives or false negatives or to provide increased confidence in the quantitative prediction. The post-processing refinement may include identification and analysis of one or more additional indicators of back pain, as described in connection with Block 208 of quantitative prediction process 200. The post-processing refinement may provide an additional level of confidence in the determination at Block 310. In some embodiments, the post-processing refinement is not performed. For example, the post-processing refinement may not be performed if the quantitative score or other value is above a certain predetermined threshold so as to increase processing time if post-processing refinement is not needed or desired.

As described above in connection with Block 208 of quantitative prediction process 200, the additional indicators identified and analyzed in the post-processing refinement at Block 312 may include paraspinal muscle tissue characteristics (e.g., multifidus muscle atrophy) may include analysis of a cross-sectional area (diameter, size) of the atrophy based on images and/or an analysis of fat fraction within the muscle tissue (e.g., percentage or ratio). The paraspinal muscle tissue characteristics may be identified, for example, in T1-weighted MRI images and/or T2-weighted fast spin-echo MRI images. The analysis and quantification of paraspinal muscle tissue characteristics may include spatial analysis (e.g., position or location of fatty atrophic changes in muscle composition). For example, fatty atrophic changes in muscle composition of paraspinal muscle tissue (e.g., multifidus muscle tissue) may be identified as high intensity areas medial and/or deep along a multifidus muscle myofascial sheath. The analysis and quantification of paraspinal muscle tissue characteristics may include quantification of an extent or severity of the changes in muscle tissue characteristics (e.g., extent of fatty infiltration measured as a percentage of a total cross-sectional area of muscle tissue).

The additional indicators identified and analyzed in the post-processing refinement at Block 312 may also include detection of active bone turnover (inflammatory response) based on SPECT images. For example, inflamed bone turns over faster than normal bone and may be identified and quantified. Patient candidates having vertebral bodies with active bone turnover may be more likely to respond favorably to a particular spinal neuromodulation procedure (e.g., basivertebral nerve procedure).

In some embodiments, the additional indicators (e.g., second-tier indicators) could include indicators of discogenic pain stemming from one or more vertebral discs (e.g., disc calcification, biochemical composition (e.g., proteoglycan and collagen content) or morphology of the disc, annular tears, Pfirrman grade scores, and/or the like). Such additional indicators may be used, for example, if the particular spinal neuromodulation procedure (e.g., basivertebral nerve procedure) is likely to be effective in treating discogenic back pain in addition to pain originating from one or more vertebral bodies or vertebral endplates. However, in some embodiments, indicators of discogenic pain (or at least only of discogenic pain) are not identified or analyzed.

In some embodiments, the additional indicators could include indicators (e.g., biomarkers) that may not be identified from images. The biomarkers may comprise, for example, substance P, cytokines, high-sensitivity C-reactive protein, or other compounds associated with inflammatory processes and/or pain and/or that correlate with pathophysiological processes associated with vertebral endplate degeneration or defects (e.g., pre-Modic changes) or Modic changes such as disc resorption, Type III and Type IV collagen degradation and formation, or bone marrow fibrosis). The biomarkers may be obtained from a patient (e.g., through a blood draw (e.g., blood serum) or through a sample of cerebrospinal fluid). Cytokine biomarker samples (e.g., pro-angiogenic serum cytokines such as vascular endothelial growth factor (VEGF)-C, VEGF-D, tyrosine-protein kinase receptor 2, VEGF receptor 1, intercellular adhesion molecule 1, vascular cell adhesion molecule 1) may be obtained from multiple different discs or vertebral bodies or foramina of the patient and compared with each other in order to determine the vertebral bodies to target for treatment. Other biomarkers may be assessed as well, such as neo-epitopes of type III and type IV pro-collagen (e.g., PRO-C3, PRO-C4) and type III and type IV collagen degradation neo-epitopes (e.g., C3M, C4M).

Biomarkers may include genetic markers, products of gene expression, autoantibodies, cytokine/growth factors, proteins or enzymes (such as heat shock proteins), and/or acute phase reactants. Biomarkers may include compounds correlated to back pain, such as inflammatory cytokines, Interleukin-1-beta (IL-1-beta), interleukin-1-alpha (IL-1-alpha), interleukin-6 (IL-6), IL-8, IL-10, IL-12, tumor necrosis factor-alpha (TNF-alpha), granulocyte-macrophage colony stimulating factor (GM-CSF), interferon gamma (INF-gamma), and prostaglandin E2 (PGE2). Biomarkers may also be indicative of presence of tumor cells or tissue if tumor tissue is being targeted by the particular procedure. Biomarkers may be found in blood serum/plasma, urine, synovial fluid, tissue biopsy, foramina, intervertebral discs, cerebrospinal fluid, or cells from blood, fluid, lymph node, and/or tissue. In some embodiments, the biomarkers can be indicators identified from images.

Figure 4:
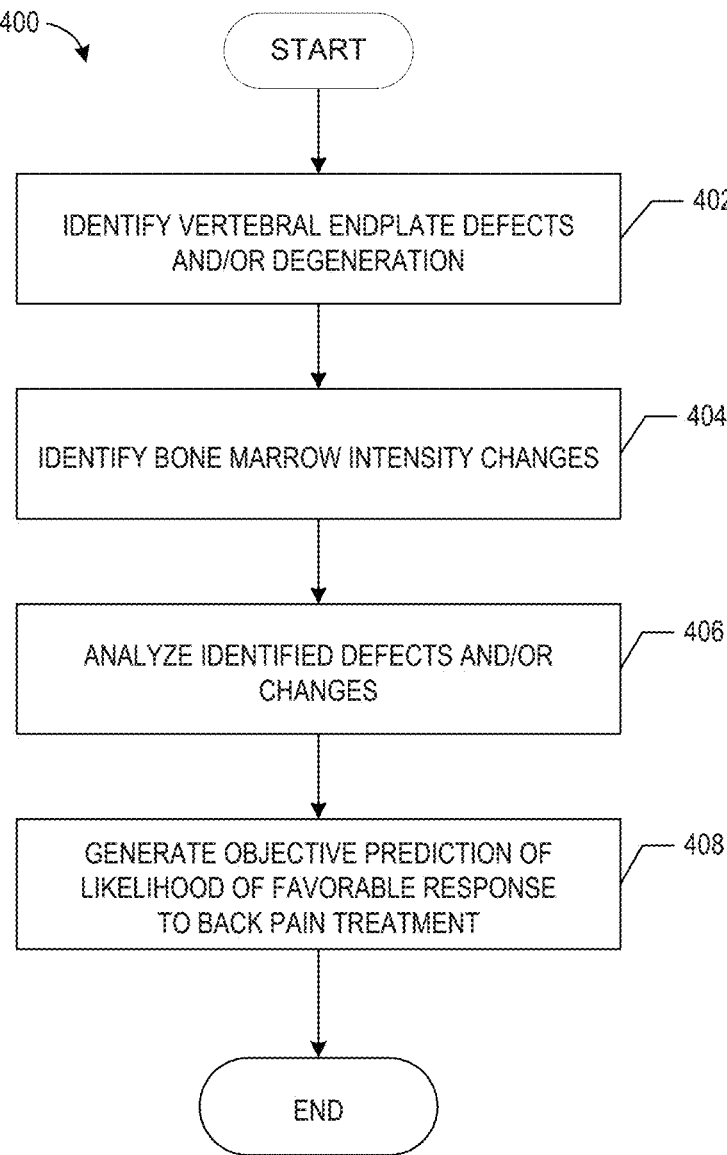

FIG. 4 illustrates an embodiment of a specific implementation of a process 400 for generating an objective or quantitative prediction of likelihood that a patient candidate has back pain arising from one or more vertebral bodies or vertebral endplates and thus will likely respond favorably to a particular spinal neuromodulation procedure (e.g., a basivertebral nerve ablation procedure). The entire process 400 or portions of the process 400 may be automated by execution of stored program instructions stored on a non-transitory computer-readable medium by one or more hardware processors. Any of the steps of the process 300 may include application of trained algorithms or trained neural networks. The quantitative prediction process 400 first includes identifying vertebral endplate defects and/or degeneration at Block 402. The quantitative prediction process 400 then includes identifying bone marrow intensity changes at Block 404. It should be appreciated that these two steps may be performed in the opposite order. The identifying steps at Blocks 402 and 404 may be performed, for example, by the image processing module 124 by applying pre-processing and feature extraction techniques, such as described above in connection with FIGS. 2 and 3. Turning to Block 406, the quantitative prediction process 400 then includes analyzing the defects and/or changes identified at Blocks 402 and 406. At Block 408, the quantitative prediction process 400 includes generating an objective prediction of likelihood that a particular patient candidate would have a favorable response to a particular spinal neuromodulation procedure (e.g., a basivertebral nerve ablation procedure). The analyzing and generating steps of Blocks 406 and 408 may be performed, for example, by the quantifier/score calculator module 126, such as described above in connection with FIGS. 2 and 3.

Any of the quantitative prediction processes 200, 300, 400 may further include displaying the quantitative score, value or other output (e.g., binary YES/NO output) on a display to be visible by a clinician (e.g., display on a clinician system 108). The display of the output may be executed or carried out by the user interface module 128 of the QPCD system 120. A clinician may decide whether or not to move forward with a procedure on a particular patient based on the output. Treatment protocols may also be adjusted based on the output.

Figure 6B:
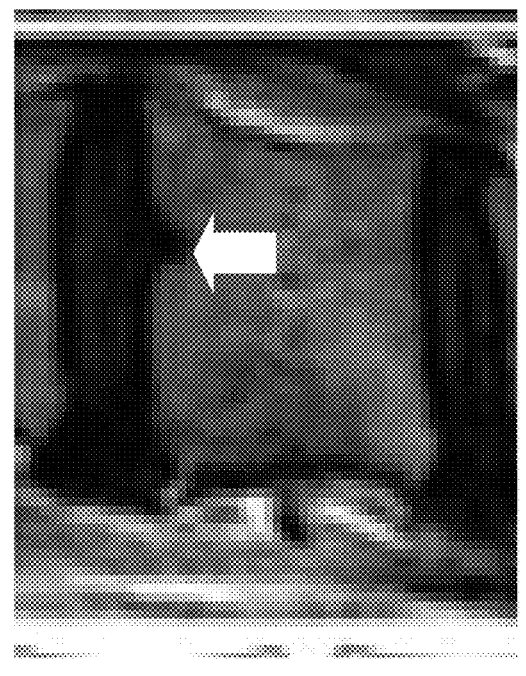
Figure 6D:
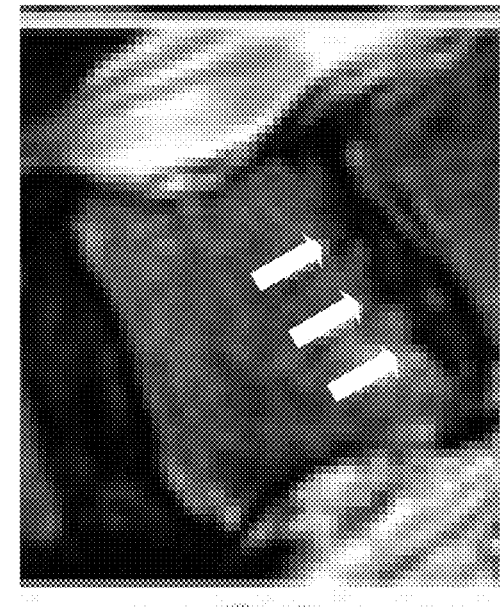
Figure 6A:
Figure 6C:
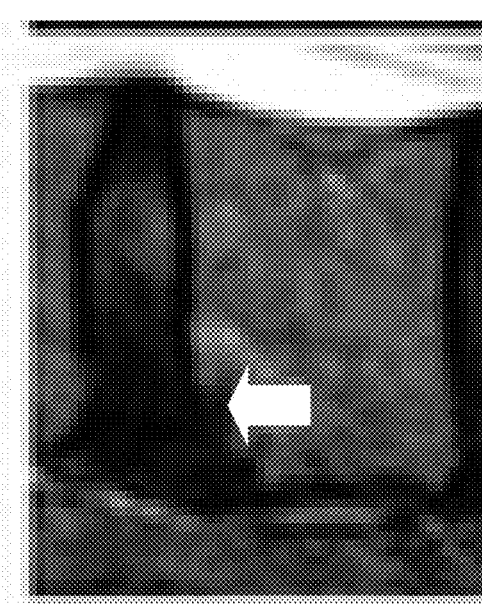
Figure 7:
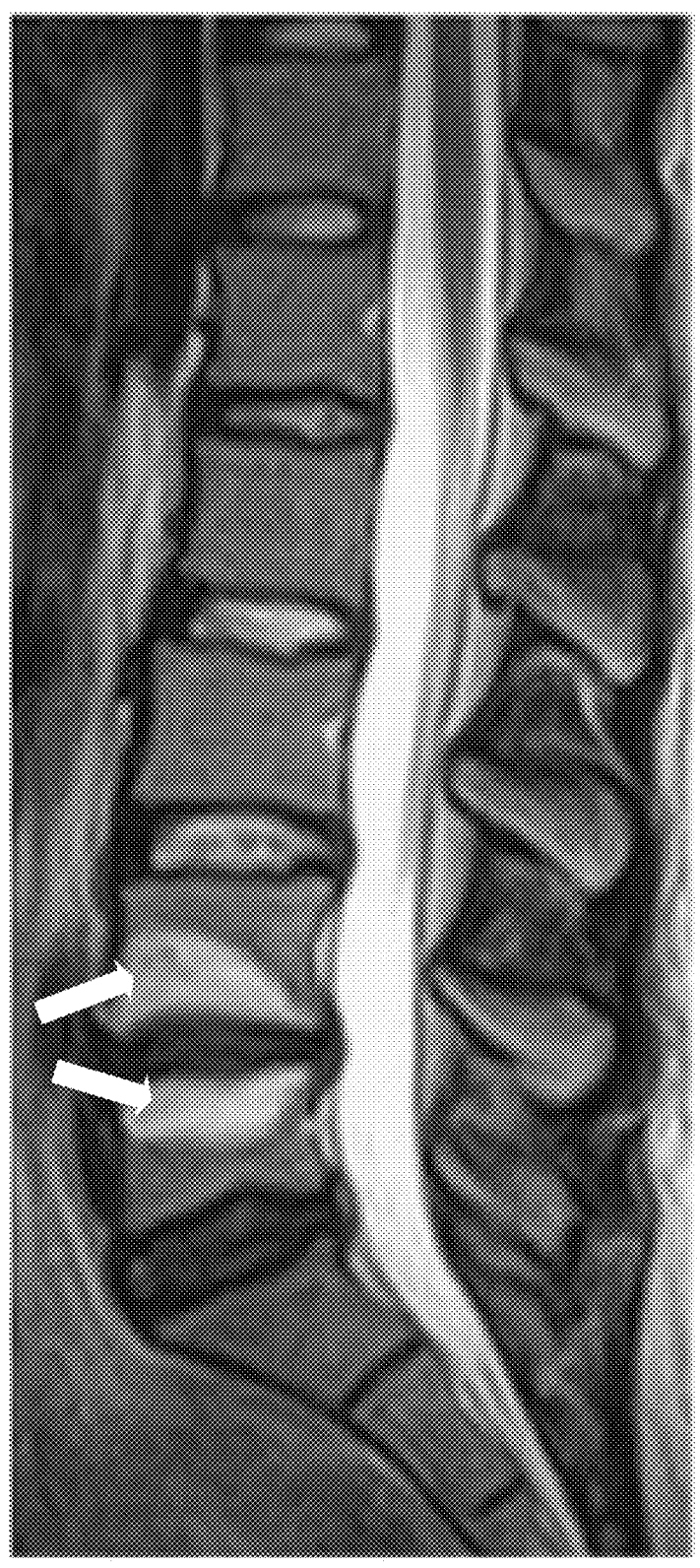

FIGS. 5, 6A-6D and 7 illustrate examples of pre-processing and/or feature extraction steps that may be performed by the QPCD system 120 to facilitate identification and quantitative assessment of a plurality of indicators of back pain. FIG. 5 shows an example of identification of vertebral levels on an MRI image of a lumbosacral region of a patient's spine (L1-S2 levels identified). The identification may include, for example, alphanumeric textual labels, as shown in FIG. 5. FIGS. 6A-6D show examples of identification of vertebral endplate defects or degeneration on various MRI images. The white arrows overlaid on the images identify the vertebral endplate defects. FIG. 6A is a normal healthy body and so no indicators are identified. FIG. 6B identifies a focal defect of a vertebral endplate. FIG. 6C identifies a corner defect of a vertebral endplate. FIG. 6D identifies erosive defects of a vertebral endplate. FIG. 7 shows an example of bone marrow intensity changes on an MRI image. The bone marrow intensity changes are identified by the white arrows overlaid on the images. Bone marrow intensity changes may appear as hyperintense tissue regions and/or hypointense tissue regions depending on types of relaxation or MRI signals and sequencing used (e.g., T1-weighted or T2-weighted MRI signals).

The vertebral endplate defects and/or bone marrow intensity changes may be identified by the image processing module 124 of the QPCD system 120 as described above. For example, the vertebral endplate defects and/or bone marrow intensity changes may be identified and extracted as features to be analyzed using image processing and feature extraction, or feature detection, techniques. The vertebral endplate defects and/or bone marrow intensity changes may be identified for example, by pixel/voxel color value comparison techniques, pixel/voxel signal intensity comparison, cluster analysis techniques, image comparison techniques by comparing with an image of a normal healthy patient without back pain indicators, etc.

Training of Neural Networks

In accordance with several embodiments, one or more steps of the processes described herein can be performed using machine learning techniques (e.g., using a trained artificial neural network that involves deep learning algorithms). The machine learning or deep learning algorithms may be trained using supervised or unsupervised training. The processes disclosed herein can employ machine learning modeling along with signal processing techniques to analyze images to identify indicators of back pain and determine quantitative predictions or scores, such as discussed above. Use of machine learning may advantageously increase reliability or accuracy of predictions, may reduce the time to identify patients likely to favorably respond to a particular spinal neuromodulation procedure (e.g., basivertebral nerve ablation procedure), and reduce false positive predictions based on human error. In accordance with several embodiments, by applying machine learning algorithms to large quantities of images of healthy subjects without back pain and images of patients having back pain, reliably accurate and extremely quick identification of patient candidates likely to respond favorably to a particular quantitative prediction of likelihood spinal neuromodulation procedure (e.g., basivertebral nerve ablation procedure) may be possible.

Machine learning modeling and signal processing techniques include but are not limited to supervised and unsupervised algorithms for regression and classification. Specific classes of algorithms include, for example, Artificial Neural Networks (Perceptron, Back-Propagation, Convolutional Neural Networks (e.g., fast-region convolutional neural networks), Recurrent Neural networks, Long Short-Term Memory Networks, Deep Belief Networks), Bayesian (Naive Bayes, Multinomial Bayes and Bayesian Networks), clustering (k-means, Expectation Maximization and Hierarchical Clustering), ensemble methods (Classification and Regression Tree variants and Boosting), single or multiple linear regression, wavelet analysis, fast Fourier transforms, instance-based (k-Nearest Neighbor, Self-Organizing Maps and Support Vector Machines), regularization (Elastic Net, Ridge Regression and Least Absolute Shrinkage Selection Operator), and dimensionality reduction (Principal Component Analysis variants, Multidimensional Scaling, Discriminant Analysis variants and Factor Analysis). In some embodiments, any number of the foregoing algorithms are not included. In several embodiments, the TensorFlow open-source software library may be used to perform machine learning algorithms. Neural networks may be trained, stored, and implemented on the QPCD system 120 e.g., the image processing module 124 and/or quantifier/score calculator module 126).

Figure 8:
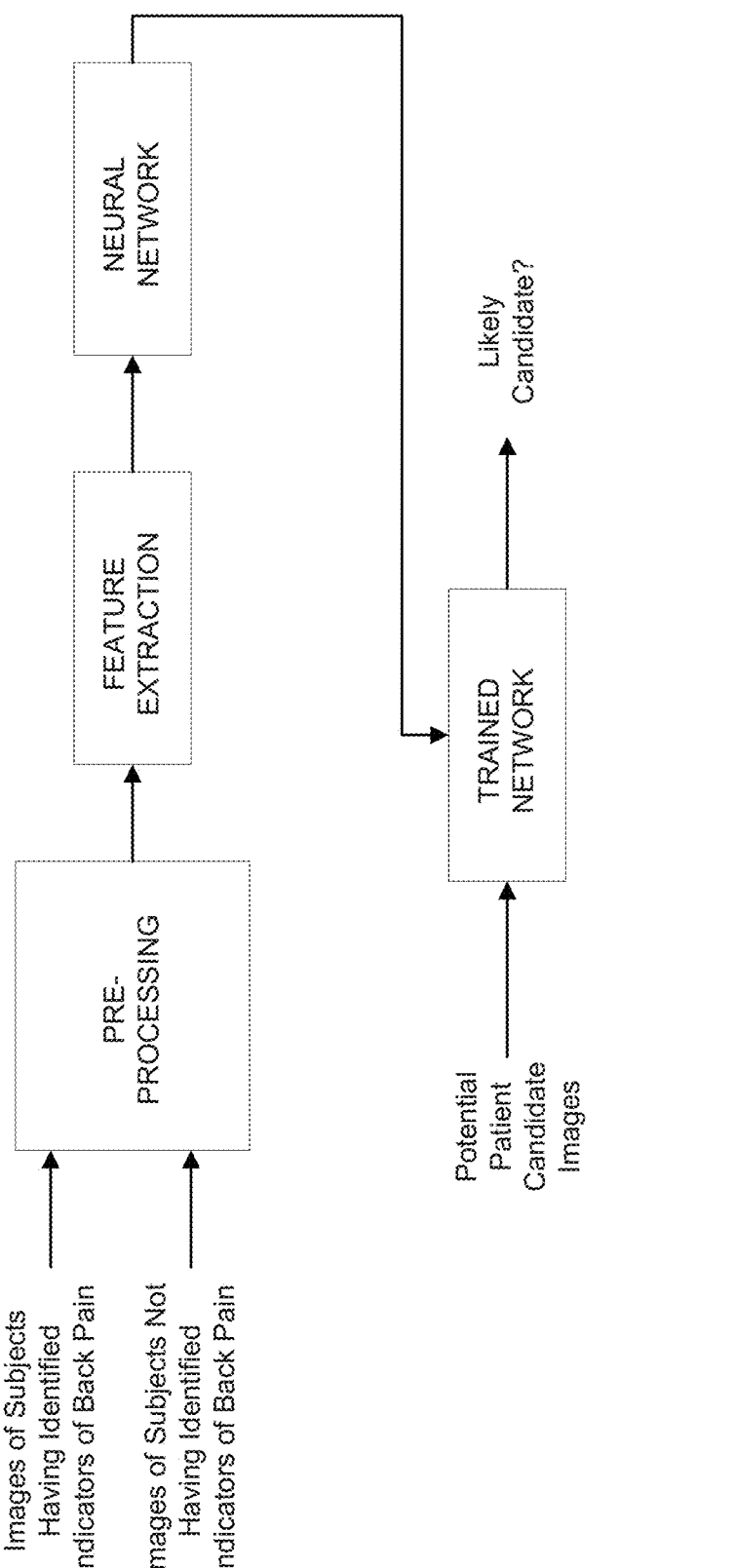
FIG. 8 illustrates a schematic flow diagram of an embodiment of training a neural network and then using the neural network to perform the quantitative prediction of likelihood that a patient candidate will respond favorably to a basivertebral nerve ablation procedure or other treatment.

FIG. 8 illustrates a schematic flow diagram of an embodiment of training a neural network for use and then using the neural network in performing one or more of the steps of the processes described herein (e.g., identifying and quantifying indicators and determining quantitative scores or other output). The neural network may be trained using spinal images of hundreds or thousands of subjects. The images may be from databases of stored images accessible by the QPCD system 120 over the network 104. The spinal images may comprise images of all or portions of a spinal anatomy (e.g., one or more regions of a vertebral column or spine, such as a lumbosacral region).

The spinal images may comprise images from past patients who had visually or manually identified indicators of back pain (e.g., a particular source or type of back pain, such as chronic low back pain) and that were treated by a particular spinal neuromodulation procedure (e.g., basivertebral nerve ablation procedure such as the INTRACEPT® Procedure offered commercially by Relievant Medsystems, Inc.), either successfully or unsuccessfully. The spinal images for training may also include images from patients who have been treated by spinal procedures for treatment of back pain other than basivertebral nerve ablation procedures (such as fusion, vertebral tumor ablation, vertebral fracture treatment, intervertebral disc ablation, or discectomy). In some instances, these other spinal procedures may also involve irritation of vertebral endplates that can result in biomarkers or other indicators of back pain (e.g., chronic low back pain), such as the biomarkers or indicators described herein. The images may also comprise images from healthy (e.g., pristine) subjects that do not have identified indicators of back pain (e.g., a particular source or type of back pain). In some embodiments, the images are MRI images (e.g., T1-weighted MRI images, T2-weighted MRI images, fat-suppression MRI images, UTE MRI images, IDEAL MRI images). In some embodiments, the images may also include images obtained by other modalities (e.g., CT, SPECT, PET, X-ray, and/or others). The images for each subject may comprise sequential images over a period of time or images at a single point in time. The training may involve comparison of images of patients taken before and after a spinal procedure (e.g., before and after a basivertebral nerve ablation procedure) to provide training on variables that may change pre- and post-treatment.

The training may involve applying pre-processing techniques to the images to facilitate feature extraction or detection. MRI images, for example, can be grainy, noisy, blurry, in at least some portions (e.g., due to artifacts caused by patient movement or metallic elements, differences in setup parameters within MRI sequences, differences in Tesla magnetic field strength, poor spatial resolution or image contrast, poor signal to noise ratio or contrast to noise ratio, improper signal weighting, truncation artifacts, aliasing, chemical shift artifacts, cross-talk, etc.). The pre-processing techniques may include, for example, rotating, aligning, re-sizing, cropping, denoising (e.g., removing artifacts, noise, grain), segmenting, smoothing, contrast or color enhancing, making intensity levels more uniform or consistent, applying filters, cleaning up, image reconstruction, and/or other image processing techniques. Rotation and alignment may be performed on the MRI images because the images may depend on patient orientation within the MRI machine, as well as other factors. Re-sizing may be needed to zoom in on the areas of the images were indicators are most likely to occur and to crop out the areas of the images that are irrelevant to the indicators. Pre-processing may also involve dividing the images into a grid of nodes or areas that can be numbered and that are uniform between each training image so as to facilitate feature extraction and comparison of images. The pre-processing may also include spatial orientation identification, vertebral level identification, general anatomical feature identification, and/or the like. In accordance with several embodiments, the pre-processing techniques advantageously result in more uniform images so as to improve training speed and accuracy of the neural network.

In some embodiments, the pre-processing may be targeted to only portions of the images that are deemed to be of interest (e.g., portions of the vertebral anatomy likely to exhibit indicators of back pain that may be effectively treated by the particular spinal neuromodulation procedure). In accordance with several embodiments, if pre-processing is not performed on the images (e.g., MRI images), the output may be less accurate due to poor image quality that results in less-than-ideal feature extraction or detection.

Training may further include performing automated feature extraction, or detection, techniques. Training may involve performing object detection tasks to recognize an object and object localization tasks to evaluate coordinates of a bounding box in which the object is situated in the image. For example, the feature extraction may include pixel/voxel color value comparison techniques, pixel/voxel signal intensity comparison techniques, analysis of variance techniques, cluster analysis techniques, image comparison techniques by comparing with an image of a normal healthy patient without back pain indicators, and/or other feature detection techniques. In some embodiments, feature extraction or detection may be partially or completely performed manually by one or more users (e.g., drawing boundaries of a bounding box surrounding particular features in the images or labelling features using a pen mouse or other user interface or user input tool). In some embodiments, training images may be provided with annotation data or tags (e.g., in a comma-separated values (CSV) file) with information about vertebral level identification, presence of indicators of back pain (e.g., vertebral endplate defects or degeneration, bone marrow intensity changes, or other indicators describe herein), location of indicators, orientation of indicators, extent of indicators, patient-reported outcomes before or after treatment (e.g., VAS scores, ODI scores, quality of life measures such as QoL or EQ scores, patient reported outcome measures, etc. In some embodiments, the annotation data may include tags that identify what the output for that particular image should be (e.g., the quantitative or objective score, value or other output indicative of whether the particular spinal neuromodulation procedure is likely to be successful). The annotation data may also include tags that identify a binary classification output of YES or NO as to whether the particular spinal neuromodulation procedure was effective, or successful, for the patient associated with the image(s). The annotation data may be provided by more than one clinician so as to generate more reliable scores.

An unsupervised neural network may be used to identify patterns to classify or extract features. For example, the neural network may involve use of classification algorithms that include clustering (k-means, Expectation Maximization and Hierarchical Clustering), ensemble methods (Classification and Regression Tree variants and Boosting), instance-based (k-Nearest Neighbor, Self-Organizing Maps and Support Vector Machines), regularization (Elastic Net, Ridge Regression and Least Absolute Shrinkage Selection Operator), and dimensionality reduction (Principal Component Analysis variants, Multidimensional Scaling, Discriminant Analysis variants and Factor Analysis) to classify or extract features that may correlate to indicators of back pain (e.g., a particular type or source of back pain). The neural network may also use TensorFlow software code modules. Although described primarily in connection with back pain (e.g., chronic low back pain), the training of neural networks and quantitative prediction techniques described herein may also be applied to other types of back pain (e.g., middle or upper back pain), neck pain, shoulder pain, peripheral nerve pain (e.g., pain in the wrists, arms, elbows, legs, knees, ankles). The images processed would include images of the respective anatomical portions and the indicators would be identified that correspond to the respective bones involved.

Spinal Neuromodulation Procedure

Any of the processes described herein may also comprise treating a patient by performing the particular spinal neuromodulation procedure (e.g., basivertebral nerve ablation procedure). The treatment devices (e.g., treatment probes) used to perform the particular spinal neuromodulation procedure (e.g., basivertebral nerve ablation procedure) may be any device capable of modulating tissue (e.g., nerves, tumors, bone tissue). Any energy delivery device capable of delivering energy can be used (e.g., radiofrequency energy delivery devices, microwave energy delivery devices, laser devices, infrared energy devices, resistive heating devices, other electromagnetic energy delivery devices, ultrasound energy delivery devices, and the like). The treatment device may be an RF energy delivery device. The RF energy delivery device may include a bipolar pair of electrodes at a distal end portion of the device. The bipolar pair of electrodes may include an active tip electrode and a return ring electrode spaced apart from the active tip electrode. The RF energy delivery device may include one or more temperature sensors (e.g., thermocouples, thermistors) positioned on an external surface of, or embedded within, a shaft of the energy delivery device. The RF energy delivery device may not employ internally circulating cooling, in accordance with several implementations.

In some implementations, water jet cutting devices may be used to modulate (e.g., denervate) nerves. In some implementations, a chemical neuromodulation tool injected into a vertebral body or at an endplate may be used to ablate or otherwise modulate nerves or other tissue. For example, the chemical neuromodulation tool may be configured to selectively bind to a nerve or endplate. In some implementations, a local anesthetic (e.g., liposomal local anesthetic) may be used inside or outside a vertebral body or other bone to denervate or block nerves. In some implementations, brachytherapy may be used to place radioactive material or implants within the vertebral body to deliver radiation therapy sufficient to ablate or otherwise denervate the vertebral body. Phototherapy may be used to ablate or otherwise modulate nerves after a chemical or targeting agent is bound to specific nerves or to a vertebral endplate.

In accordance with several implementations, thermal energy may be applied within a cancellous bone portion (e.g., by one or more radiofrequency (RF) energy delivery instruments coupled to one or more RF generators) of a vertebral body. The thermal energy may be conducted by heat transfer to the surrounding cancellous bone, thereby heating up the cancellous bone portion. In accordance with several implementations, the thermal energy is applied within a specific frequency range and having a sufficient temperature and over a sufficient duration of time to heat the cancellous bone such that the basivertebral nerve extending through the cancellous bone of the vertebral body is modulated. In several implementations, modulation comprises permanent ablation or denervation or cellular poration (e.g., electroporation). In some implementations, modulation comprises temporary denervation or inhibition. In some implementations, modulation comprises stimulation or denervation without necrosis of tissue.

For thermal energy, temperatures of the thermal energy may range from about 60 to about 115 degrees Celsius (e.g., from about 60 to about 80 degrees Celsius, from about 70 to about 90 degrees Celsius, from about 75 to about 90 degrees Celsius, from about 65 to about 75 degrees Celsius, from about 68 to about 78 degrees Celsius, from about 83 to about 87 degrees Celsius, from about 80 to about 100 degrees Celsius, from about 85 to about 95 degrees Celsius, from about 90 to about 110 degrees Celsius, from about 95 to about 115 degrees Celsius, from about 70 to about 115 degree Celsius, or overlapping ranges thereof). The temperature ramp may range from 0.1-5 degrees Celsius/second (e.g., 0.1-1.0 degrees Celsius/second, 0.25 to 2.5 degrees Celsius/second, 0.5-2.0 degrees Celsius/second, 1.0-3.0 degrees Celsius/second, 1.5-4.0 degree Celsius/second, 2.0-5.0 degrees Celsius/second). The time of treatment may range from about 10 seconds to about 1 hour (e.g., from 10 seconds to 1 minute, 1 minute to 5 minutes, from 5 minutes to 10 minutes, from 5 minutes to 20 minutes, from 8 minutes to 15 minutes, from 10 minutes to 20 minutes, from 15 minutes to 30 minutes, from 20 minutes to 40 minutes, from 30 minutes to 1 hour, from 45 minutes to 1 hour, or overlapping ranges thereof). Pulsed energy may be delivered as an alternative to or in sequence with continuous energy. For radiofrequency energy, the energy applied may range from 350 kHz to 650 kHz (e.g., from 400 kHz to 600 kHz, from 350 kHz to 500 kHz, from 450 kHz to 550 kHz, from 500 kHz to 650 kHz, overlapping ranges thereof, or any value within the recited ranges, such as 450 kHz±5 kHz, 475 kHz±5 kHz, 487 kHz±5 kHz). A power of the radiofrequency energy may range from 5 W to 100 W (e.g., from 5 W to 15 W, from 5 W to 20 W, from 5 W to 30 W, from 8 W to 12 W, from 10 W to 25 W, from 15 W to 25 W, from 20 W to 30 W, from 8 W to 24 W, from 5 W to 50 W, from 10 W to 20 W, from 20 W to 50 W, from 25 W to 75 W, from 50 W to 100 W, and overlapping ranges thereof, or any value within the recited ranges).

In accordance with several implementations, a thermal treatment dose (e.g., using a cumulative equivalent minutes (CEM) 43 degrees Celsius thermal dose calculation metric model) is between 200 and 300 CEM (e.g., between 200 and 240 CEM, between 230 CEM and 260 CEM, between 240 CEM and 280 CEM, between 235 CEM and 245 CEM, between 260 CEM and 300 CEM) or greater than a predetermined threshold (e.g., greater than 240 CEM), or a thermal treatment dose equivalent using an Arrhenius model. The CEM number may represent an average thermal cumulative dose value at a target treatment region or location and may represent a number that expresses a desired dose for a specific biological end point. Thermal damage may occur through necrosis or apoptosis.

Cooling may optionally be provided to prevent surrounding tissues from being heated during the nerve modulation procedure. The cooling fluid may be internally circulated through the delivery device from and to a fluid reservoir in a closed circuit manner (e.g., using an inflow lumen and an outflow lumen). The cooling fluid may comprise pure water or a saline solution having a temperature sufficient to cool electrodes (e.g., 2-70 degrees Celsius, 2-10 degrees Celsius, 5-10 degrees Celsius, 5-15 degrees Celsius, 20-50 degrees Celsius, 40-70 degree Celsius, overlapping ranges thereof, or any value within the recited ranges). Cooling may be provided by the same instrument used to deliver thermal energy (e.g., heat) or a separate instrument. In some implementations, cooling is delivered to the region (e.g., the cooling fluid exits the fluid delivery instrument). In accordance with several implementations, cooling is not used.

In some implementations, ablative cooling may be applied to the nerves or bone tissue instead of heat (e.g., for cryoneurolysis or cryoablation applications). The temperature and duration of the cooling may be sufficient to modulate intraosseous nerves (e.g., ablation, or localized freezing, due to excessive cooling). The cold temperatures may destroy the myelin coating or sheath surrounding the nerves. The cold temperatures may also advantageously reduce the sensation of pain. The cooling may be delivered using a hollow needle under fluoroscopy or other imaging modality.

In some implementations, one or more fluids or agents may be delivered to a target treatment site to modulate a nerve. The agents may comprise bone morphogenetic proteins, for example. In some implementations, the fluids or agents may comprise chemicals for modulating nerves (e.g., chemoablative agents, alcohols, phenols, nerve-inhibiting agents, or nerve stimulating agents). The fluids or agents may be delivered using a hollow needle or injection device under fluoroscopy or other imaging modality. Although spinal neuromodulation procedures are specifically discussed herein, other neuromodulation (e.g., peripheral neuromodulation procedures) may be performed.

Terminology

In some implementations, the system comprises various features that are present as single features (as opposed to multiple features). For example, in one embodiment, the system includes a single radiofrequency generator, a single introducer cannula with a single stylet, a single radiofrequency energy delivery device or probe, and a single bipolar pair of electrodes. A single thermocouple (or other means for measuring temperature) may also be included. Multiple features or components are provided in alternate embodiments.

In some implementations, the system comprises one or more of the following: means for quantitatively predicting a scored indicative of likelihood of a patient responding favorably to treatment, means for tissue modulation (e.g., an ablation or other type of modulation catheter or delivery device), means for imaging (e.g., MRI, CT, fluoroscopy), means for accessing (e.g., introducer assembly, curved cannulas, drills, curettes), etc.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "70" is disclosed, then "about 70" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. The section headings used herein are merely provided to enhance readability and are not intended to limit the scope of the embodiments disclosed in a particular section to the features or elements disclosed in that section. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. The term "embodiment" should not be limited to an interpretation as the "invention" and can mean a non-limiting example, implementation or aspect.

What is claimed is:

1. A computer-implemented method of quantitatively predicting likelihood that a particular subject would respond favorably to basivertebral nerve ablation to treat back pain, the method comprising:

receiving one or more images of at least a portion of a spine of the particular subject;

applying pre-processing imaging techniques to the one or more images using a trained neural network;

extracting, using the trained neural network, features from the one or more images to identify a plurality of indicators of back pain by analyzing pixel values and spatial relationships within the one or more images;

determining, using the trained neural network, an objective score indicative of a likelihood that the particular subject would respond favorably to basivertebral nerve ablation based on said extracting; and initiating, a treatment recommendation for basivertebral nerve ablation if the objective score exceeds a predetermined threshold.

2. The computer-implemented method of claim 1, wherein the plurality of indicators comprises at least one of: (i) bone marrow intensity changes and (ii) vertebral endplate defects or characteristics of vertebral endplate degeneration.

3. The computer-implemented method of claim 1, wherein the plurality of indicators comprises both (i) bone marrow intensity changes and (ii) vertebral endplate defects or characteristics of vertebral endplate degeneration.

4. The computer-implemented method of claim 1, wherein the extracting features from the one or more images to identify the plurality of indicators of back pain comprises applying a trained neural network to the one or more images to automatically identify the plurality of indicators of back pain.

5. The computer-implemented method of claim 1, wherein the one or more images comprise images obtained from ultrashort time-to-echo ("UTE") MRI sequenced imaging.

6. The computer-implemented method of claim 1, wherein the one or more images comprise images obtained from Iterative Decomposition of water and fat with Echo Asymmetry and Least-squares estimation ("IDEAL") MRI sequenced imaging.

7. The computer-implemented method of claim 1, wherein the one or more images comprise images obtained from fast spin echo MRI sequenced imaging.

8. The computer-implemented method of claim 1, wherein the one or more images comprise images obtained from computed tomography ("CT") imaging.

9. The computer-implemented method of claim 1, wherein the one or more images comprise images obtained from positron emission tomography ("PET") bone imaging.

10. The computer-implemented method of claim 1, wherein the one or more images comprises images obtained from X-ray imaging.

11. The computer-implemented method of claim 1, wherein determining an objective score comprises quantifying the plurality of indicators based on an extent of the plurality of indicators.

12. The computer-implemented method of claim 11, wherein the extent may comprise a quantity, a severity, and/or a spatial assessment.

13. The computer-implemented method of claim 1, wherein the plurality of indicators further include one or more of the following:

changes in multifidus muscle characteristics;

bone turnover in SPECT images; and a pain score obtained for the particular subject.

14. The computer-implemented method of claim 1, wherein at least a portion of the method is performed by application of machine learning algorithms.

15. The computer-implemented method of claim 1, further comprising displaying an output of the objective score on a display.

16. A computer-implemented method of quantitatively predicting likelihood that a particular subject would respond favorably to basivertebral nerve ablation to treat chronic low back pain, the method comprising:

receiving one or more magnetic resonance images (MRIs) of at least a lumbosacral region of a spine of the particular subject;

applying pre-processing imaging techniques to the one or more MRIs in order to provide uniformity of the one or more MRIs for feature detection using a trained neural network;

detecting, using the trained neural network, features from the one or more MRIs to identify a plurality of indicators of chronic low back pain by analyzing pixel values and spatial relationships within the one or more MRIs, wherein the plurality of indicators comprises bone marrow intensity changes and vertebral endplate defects or characteristics of vertebral endplate degeneration;

quantifying the identified plurality of indicators based on an extent of the plurality of indicators, wherein the extent may comprise a quantity, a severity, or a spatial assessment;

determining, using the trained neural network, an objective score indicative of a likelihood that the particular subject would respond favorably to a basivertebral nerve ablation procedure based on said quantifying; and initiating a treatment recommendation for basivertebral nerve ablation if the objective score exceeds a predetermined threshold.

17. The computer-implemented method of claim 16, wherein the detecting features from the one or more MRIs to identify the plurality of indicators of chronic low back pain comprises applying a trained neural network to the one or more images to automatically identify the plurality of indicators of chronic low back pain.

18. The computer-implemented method of claim 16, wherein the spatial assessment comprises quantifying prevalence of the plurality of indicators in different locations or regions of a vertebral body or endplate of the lumbosacral region of the spine.

19. The computer-implemented method of claim 16, wherein the severity comprises size or volume of the plurality of indicators.

\*   \*   \*   \*   \*